US006977153B2

(12) United States Patent  
Kumar et al.

(10) Patent No.: US 6,977,153 B2  
(45) Date of Patent: Dec. 20, 2005

(54) ROLLING CIRCLE AMPLIFICATION OF RNA

(75) Inventors: Gyanendra Kumar, Guilford, CT (US); Patricio Abarzúa, West Caldwell, NJ (US)

(73) Assignee: Qiagen GmbH (DE)

( * ) Notice: Subject to any disclaimer, the term of this patent is extended or adjusted under 35 U.S.C. 154(b) by 68 days.

(21) Appl. No.: 10/335,573

(22) Filed: Dec. 31, 2002

(65) Prior Publication Data

US 2004/0126770 A1 Jul. 1, 2004

(51) Int. Cl.[7] .............................. C12Q 1/68; C12P 19/34
(52) U.S. Cl. ......................... 435/6; 435/91.2; 435/91.1
(58) Field of Search ........................ 435/6, 91.2, 91.1

(56) References Cited

U.S. PATENT DOCUMENTS

| | | |
|---|---|---|
| 2,264,423 A | 12/1941 | Wingenroth |
| 3,687,808 A | 8/1972 | Merigan et al. |
| 4,469,863 A | 9/1984 | Ts'o |
| 4,476,301 A | 10/1984 | Imbach et al. |
| 4,748,111 A | 5/1988 | Dattagupat et al. |
| 4,845,205 A | 7/1989 | Huynh Dinh et al. |
| 4,883,750 A | 11/1989 | Whiteley et al. |
| 4,965,188 A | 10/1990 | Mullis et al. |
| 4,981,957 A | 1/1991 | Lebleu et al. |
| 4,984,957 A | 1/1991 | Noguchi et al. |
| 4,994,373 A | 2/1991 | Stavrianopoulos et al. |
| 5,001,050 A | 3/1991 | Blanco et al. |
| 5,023,243 A | 6/1991 | Tullis |
| 5,034,506 A | 7/1991 | Summerton et al. |
| 5,043,272 A | 8/1991 | Hartley |
| 5,118,800 A | 6/1992 | Smith et al. |
| 5,130,238 A | 7/1992 | Malek et al. |
| 5,130,302 A | 7/1992 | Spielvogel et al. |
| 5,134,066 A | 7/1992 | Rogers et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,198,543 A | 3/1993 | Blanco et al. |
| 5,214,134 A | 5/1993 | Weis et al. |
| 5,216,141 A | 6/1993 | Benner |
| 5,235,033 A | 8/1993 | Summerton et al. |
| 5,242,794 A | 9/1993 | Whiteley et al. |
| 5,264,423 A | 11/1993 | Cohen et al. |
| 5,264,562 A | 11/1993 | Matteucci |
| 5,264,564 A | 11/1993 | Matteucci |
| 5,264,567 A | 11/1993 | Numata et al. |
| 5,273,638 A | 12/1993 | Konrad et al. |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,328,824 A | 7/1994 | Ward et al. |
| 5,354,668 A | 10/1994 | Auerbach |
| 5,359,044 A | 10/1994 | Cook et al. |
| 5,367,066 A | 11/1994 | Urdea et al. |
| 5,367,069 A | 11/1994 | Beck et al. |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,409,818 A | 4/1995 | Davey et al. |
| 5,412,087 A | 5/1995 | McGall et al. |
| 5,427,930 A | 6/1995 | Birkenmeyer et al. |
| 5,429,807 A | 7/1995 | Matson et al. |
| 5,432,272 A | 7/1995 | Benner |
| 5,434,257 A | 7/1995 | Matteucci et al. |
| 5,446,137 A | 8/1995 | Maag et al. |
| 5,451,067 A | 9/1995 | Pieper |
| 5,451,203 A | 9/1995 | Lamb |
| 5,453,496 A | 9/1995 | Caruthers et al. |
| 5,455,166 A | 10/1995 | Walker |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,427 A | 12/1995 | Fujima |

(Continued)

FOREIGN PATENT DOCUMENTS

| | | |
|---|---|---|
| AU | 84173/91 | 2/1992 |
| EP | 0 070 685 | 7/1982 |

(Continued)

OTHER PUBLICATIONS

Ørum et al. Single base pair mutation analysis by PNA directed PCR clamping. *Nucl. Acids Res.* 21(23):5332–5336 (1993).

(Continued)

*Primary Examiner*—Kenneth R. Horlick  
*Assistant Examiner*—Joyce Tung  
(74) *Attorney, Agent, or Firm*—Needle & Rosenberg, P.C.

(57) ABSTRACT

Disclosed are compositions and methods for amplification of RNA molecules. The disclosed method involves synthesizing first strand cDNA molecules from RNA molecules, circularizing the first strand cDNA molecules and replicating the circularized first strand cDNA molecules using rolling circle replication. The method can be aided by the use of specialized primers for cDNA synthesis and specialized probes for circularizing the first strand cDNA molecules. The method can be used to replicate and amplify multiple RNA molecules, such as all RNA molecules in a sample or all mRNA molecules in a sample, or be used to replicate and amplify specific RNA molecules. Rolling circle replication of the circularized first strand cDNA molecules results in long DNA strands containing tandem repeats of the cDNA sequence. The tandem sequence DNA can be used directly (for detection of sequences, for example), further amplified, or used any other purpose. Double-stranded tandem sequence DNA can be used to produce unit lengths of the cDNA sequence. Tandem sequence DNA can also be transcribed to produce transcripts having sequence complementary to or matching the sequence of RNA molecules.

179 Claims, 6 Drawing Sheets

U.S. PATENT DOCUMENTS

| | | | |
|---|---|---|---|
| 5,476,925 A | 12/1995 | Letsinger et al. |
| 5,484,908 A | 1/1996 | Froehler et al. |
| 5,489,667 A | 2/1996 | Knipf et al. |
| 5,502,177 A | 3/1996 | Matteucci et al. |
| 5,510,270 A | 4/1996 | Fodor et al. |
| 5,514,785 A | 5/1996 | Van Ness et al. |
| 5,516,134 A | 5/1996 | Crawford et al. |
| 5,519,126 A | 5/1996 | Hécht |
| 5,519,134 A | 5/1996 | Acevedo et al. |
| 5,521,065 A | 5/1996 | Whiteley et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,547,843 A | 8/1996 | Studier et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,037 A | 10/1996 | Sutherland et al. |
| 5,563,253 A | 10/1996 | Agrawal et al. |
| 5,563,912 A | 10/1996 | Yasunaga et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,609 A | 1/1997 | Auerbach |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer et al. |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,389 A | 3/1997 | Auerbach |
| 5,614,390 A | 3/1997 | McCaslin et al. |
| 5,614,617 A | 3/1997 | Cook et al. |
| 5,618,704 A | 4/1997 | Sanghui et al. |
| 5,623,070 A | 4/1997 | Cook et al. |
| 5,625,050 A | 4/1997 | Beaton et al. |
| 5,627,053 A | 5/1997 | Usman et al. |
| 5,629,158 A | 5/1997 | Uhlen |
| 5,629,179 A | 5/1997 | Mierendorf et al. |
| 5,633,360 A | 5/1997 | Bischofberger et al. |
| 5,639,873 A | 6/1997 | Barascut et al. |
| 5,646,265 A | 7/1997 | McGee |
| 5,648,245 A * | 7/1997 | Fire et al. .................. 435/91.1 |
| 5,658,873 A | 8/1997 | Bentsch-Frank et al. |
| 5,663,312 A | 9/1997 | Chatuvedula |
| 5,670,633 A | 9/1997 | Cook et al. |
| 5,677,437 A | 10/1997 | Teng et al. |
| 5,677,439 A | 10/1997 | Wies et al. |
| 5,681,941 A | 10/1997 | Cook et al. |
| 5,700,920 A | 12/1997 | Altmann et al. |
| 5,714,320 A | 2/1998 | Kool |
| 5,714,331 A | 2/1998 | Buchardt et al. |
| 5,719,262 A | 2/1998 | Buchardt et al. |
| 5,733,733 A | 3/1998 | Auerbach |
| 5,821,084 A | 10/1998 | Olmsted et al. |
| 5,854,053 A | 12/1998 | Lizardi |
| 5,866,336 A | 2/1999 | Nazarenko et al. |
| 5,874,260 A | 2/1999 | Cleuziat et al. |
| 5,876,924 A | 3/1999 | Zhang et al. |
| 5,886,329 A | 3/1999 | Demetriou |
| 5,925,517 A | 7/1999 | Tyagi et al. |
| 5,942,391 A | 8/1999 | Zhang et al. |
| 6,017,703 A | 1/2000 | Kinders et al. |
| 6,057,105 A | 5/2000 | Hoon et al. |
| 6,096,880 A | 8/2000 | Kool |
| 6,117,635 A | 9/2000 | Nazarenko et al. |
| 6,124,120 A | 9/2000 | Lizardi |
| 6,132,728 A | 10/2000 | Beachy et al. |
| 6,143,495 A | 11/2000 | Lizardi et al. |
| 6,183,960 B1 | 2/2001 | Lizardi |
| 6,203,984 B1 * | 3/2001 | Hu et al. ...................... 435/6 |
| 6,210,884 B1 | 4/2001 | Lizardi |
| 6,214,587 B1 | 4/2001 | Dattagupta et al. |
| 6,221,603 B1 | 4/2001 | Mahtani |
| 6,248,535 B1 | 6/2001 | Dandenberg et al. |
| 6,277,607 B1 | 8/2001 | Tyagi et al. |
| 6,280,949 B1 | 8/2001 | Lizardi |
| 6,287,768 B1 | 9/2001 | Chenchik et al. |
| 6,287,776 B1 | 9/2001 | Hefti |
| 6,287,824 B1 | 9/2001 | Lizardi |
| 6,288,220 B1 | 9/2001 | Kambara et al. |
| 6,291,187 B1 | 9/2001 | Kingsmore et al. |
| 6,291,193 B1 | 9/2001 | Khodadoust |
| 6,291,669 B1 | 9/2001 | Kwiatkowski et al. |
| 6,294,664 B1 | 9/2001 | Ravikumar et al. |
| 6,297,006 B1 | 10/2001 | Drmanac et al. |
| 6,312,902 B1 | 11/2001 | Shultz et al. |
| 6,316,229 B1 | 11/2001 | Lizardi et al. |
| 6,323,009 B1 | 11/2001 | Lasken et al. |
| 6,329,150 B1 | 12/2001 | Lizardi et al. |
| 6,344,329 B1 | 2/2002 | Lizardi |
| 6,440,707 B1 | 8/2002 | Kwok et al. |
| 6,458,544 B1 | 10/2002 | Miller |
| 6,472,185 B2 | 10/2002 | McCasky-Feazel et al. |
| 6,479,242 B1 | 11/2002 | Guo et al. |
| 6,479,244 B1 | 11/2002 | Belouci et al. |
| 6,573,051 B2 | 6/2003 | Alsmadi et al. |
| 6,617,137 B2 | 9/2003 | Dean et al. |
| 2002/0192649 A1 | 12/2002 | Lizardi |
| 2003/0022167 A1 | 1/2003 | Alsamadi et al. |
| 2003/0032024 A1 | 2/2003 | Lizardi |

FOREIGN PATENT DOCUMENTS

| | | |
|---|---|---|
| EP | 0 128 332 | 12/1984 |
| EP | 0 356 021 | 2/1990 |
| EP | 0 379 369 | 7/1990 |
| EP | 0 439 182 | 7/1991 |
| EP | 0 466 520 | 1/1992 |
| EP | 0 505 012 | 9/1992 |
| EP | 0 667 393 | 8/1995 |
| EP | 0 678 582 | 10/1995 |
| EP | 0 745 690 | 12/1996 |
| GB | 2332516 | 6/1999 |
| JP | 4262799 | 9/1992 |
| JP | 4304900 | 10/1992 |
| WO | WO 91/80307 | 6/1991 |
| WO | WO 92/01813 | 2/1992 |
| WO | WO 94/16108 | 7/1994 |
| WO | WO 94/24312 | 10/1994 |
| WO | WO 95/03430 | 2/1995 |
| WO | WO 95/03432 | 2/1995 |
| WO | WO 95/25180 | 9/1995 |
| WO | WO 95/22623 | 11/1995 |
| WO | WO 95/35390 | 12/1995 |
| WO | WO 96/33207 | 10/1996 |
| WO | WO 97/17076 | 5/1997 |
| WO | WO 97/17471 | 5/1997 |
| WO | WO 97/19193 | 5/1997 |
| WO | WO 97/20948 | 6/1997 |
| WO | WO 97/42346 | 11/1997 |
| WO | WO 98/04746 | 2/1998 |
| WO | WO 99/31276 | 6/1999 |
| WO | WO 00/71562 | 11/2000 |

OTHER PUBLICATIONS

AAAI Board of Directors. Measurement of specific and nonspecific IgG$_4$ levels as diagnositc and prognostic tests for clinical allergy. *J. Allergy. Clin. Immunol.* 95(3):652–654 (1995).

Abravaya et al. Detection of point mutations with a modified ligase chain reaction (Gap–LCR). *Nucl. Acids Res.* 23(4):675–682 (1995).

Aliotta et al. Thermostable Bst DNA polymerase I lacks a 3'→5' Proofreading exonuclease activity. *Gen. Anal.* 12:185–195 (1996).

Alves et al. Dot blot detection of point mutations with adjacently hybridising synthetic oligonucleotide probes. *Nucl. Acids Res.* 16(17):8723 (1988).

Anderson et al. A comparison of selected mRNA and protein abundances in human liver. *Electrophoresis* 18:533–537 (1997).

Arnold et al. Assay Formats Involving Acridinium–Ester–Labeled DNA Probes. *Clin. Chem.* 35(8):1588–1594 (1989).

Baner et al. Signal amplification of padlock probes by rolling circle replication. *Nucl. Acid Res.* 26(22):5073–5078 (1998).

Barany. Genetic disease detection and DNA amplification using cloned thermostable ligase. *Proc. Natl. Acad. Sci. USA* 88:189–193 (Jan. 1991).

Beaucage et al. Deoxynucleoside phosphoramidites—a new class of key intermediates for deoxypolynucleotide synthesis. *Tetrahedron Lett.* 22(20):1859–1862(1981).

Bertina et al. Mutation in blood coagulation factor V associated with resistance to activated protein C. *Nature* 369:64–67 (May 5, 1994).

Birkenmeyer et al. DNA probe amplification methods. *J. Virol. Meth.* 35:117–126 (1991).

Blanco et al. Characterization and purification of a phage Ø29–encoded DNA polymerase required for the initiation of replication. *Proc. Natl. Acad. Sci. USA* 81:5325–5329 (Sep. 1984).

Blanco et al. Highly Efficient DNA Synthesis by the Phage Ø29 DNA Polymerase. *J. Biol. Chem.* 264(15):8935–8940 (May 25, 1989).

Blanco et al. Terminal protein–primed DNA amplification. *Proc. Natl. Acad. Sci. USA* 91:12198–12202 (Dec. 1994).

Boehmer et al. Herpes Simplex Virus Type 1 ICP8: Helix–Destabilizing Properties. *J. Virol.* 67(2):711–715 (Feb. 1993).

Bonnet et al. Thermodynamic basis of the enhanced specificity of structured DNA probes. *Proc. Natl. Acad. Sci. USA*, 96(11):6171–6176 (May 1999).

Broude et al. Enhanced DNA sequencing by hybridization. *Proc. Natl. Acad. Sci. USA* 91:3072–3076 (Apr. 1994).

Brush. Dye hard: protein gel staining products. *The Scientist.* 12:16–22 (May 11, 1998).

Burgess et al. A New Photolabile Protecting Group for Nucleotides. *Abstracts of Papers, Part 2.; 211$^{th}$ ACS National Meeting, American Chemical Society.* New Orleans, LA, Mar. 24–28, 1996.

Butler et al. Bacteriophage SP6–specific RNA polymerase. *J. Biol. Chem.* 257(10):5772–5778 (May 25, 1982).

Chang. The pharmacological basis of anti–IgE therapy. *Nat. Biotech.* 18:157–162 (Feb. 2000).

Chatterjee et al. Cloning and overexpression of the gene encoding bacteriophage T5 DNA polymerase. *Gene* 97:13–19 (1991).

Chetverina et al. Cloning of RNA molecules in vitro. *Nucl. Acids Res.* 21(10):2349–2353 (1993).

Colantuoni et al. Gene Expression Profiling in Postmortem Rett Syndrome Brain: Differential Gene Expression and Patient Classification. *Neutoboil. Dis.* 8:847–865 (2001).

Colantuoni et al. High Throughput Analysis of Gene Expression in the Human Brain. *J. Neurosci. Res.* 59:1–10.

Craxton et al. Linear Amplification Sequencing, a Powerful Method for Sequencing DNA. *Meth. Compan. Meth. Enzymol.* 3(1):20–26 (Aug. 1991).

Crooke et al. Pharmacokinetic Properties of Several Novel Oligonucleotide Analogs in mice. *J. Pharmacol. Exp. Ther.* 277(2):923–937 (1996).

Daubendiek et al. Generation of catalytic RNAs by rolling transcription of synthetic DNA nanocircles. *Nat. Biotechnol.* 15(3):273–277 (Mar. 1997).

Daubendiek et al. Rolling–Circle RNA Synthesis: Circular Oligonucleotides an Efficient Substrates for T7 RNA Polymerase. *J. Am. Chem. Soc.* 117:7818–7819 (1995).

Davanloo et al. Cloning and expression of the gene for bacteriophage T7 RNA polymerase. *Proc. Natl. Acad. Sci. USA* 81:2035–2039 (Apr. 1984).

Dean et al. Rapid Amplification of Plasmid and Phage DNA Using Phi29 DNA Polymerase and Multiply–Primed Rolling Circle Amplification. *Genome Res.* 11:1095–1099 (2001).

Dynal Technical Handbook. Biomagnetic techniques in molecular biology. (DYNAL A.S., 1995).

Ekins. Ligand assays: from electrophoresis to miniaturized microarrays. *Clin. Chem.* 44(9):2015–2030 (1998).

Englisch et al. Chemically modified oligonucleotides as probes and inhibitors. *Angewandte Chemie, Intl Ed.* 30(6):613–722 (Jun. 1991).

Ernst et al. Cyanine Dye Labeling Reagents for Sulfhydryl Groups. *Cytometry* 10:3–10 (1989).

Fields et al. How many genes in the human genome? *Nat. Genet.* 7:345–346 (Jul. 1994).

Fire et al. Rolling replication of short DNA circles. *Proc. Natl. Acad. Sci. USA* 92:4641–4645 (May 1995).

Fleischmann et al. Whole–Genome Random Sequencing and Assembly of *Haemophilus influenza* Rd. *Science* 269:496–512 (Jul. 28, 1995).

Gasparro et al. Site–specific targeting of psoralen photoadducts with a triple helix–forming oligonucleotide: characterization of psoralen monoadduct and crosslink formation. *Nucl. Acids Res.* 22(14):2845–2851 (1994).

Gerdes et al. Dynamic Changes in the Higher–Level Chromatin of Specific Sequences Revealed by In Situ Hybridization to Nuclear Halos. *J. Cell Biol.* 126(2):289–304 (Jul. 1994).

Guatelli et al. Isothermal, in vitro amplification of nucleic acids by a multienzyme reaction modeled after retroviral replication. *Proc. Natl. Acad. Sci. USA* 87:1874–1878 (Mar. 1990).

Gunji et al. Correlation between the serum level of hepatitis C virus RNA and disease activities in acute and chronic hepatitis C. *Int. J. Cancer* 52(5):726–730 (1992).

Guo et al. Direct Fluorescence analysis of enetic polymorphisms by hybridization with oligonucleotide arrays on glass supports. *Nucl. Acids Res.* 22(24):5456–5464 (1994).

Guo et al. Enhanced discrimination of single nucleotide polymorphisms by artificial mismatch hybridization. *Nat. Biotechnol.* 15:331–335 (Apr. 1997).

Gupta et al. Expression of HIV–1 RNA in plasma correlates with the development of AIDS: a multicenter AIDS cohort study (MACS) *Ninth International Conference on AIDS/ Fourth STD World Congress.* Jun. 6–11, 1993, Berlin, Germany (abstract).

Gusev et al. Rolling Circle Amplification: A New Approach to Increase Sensitivity for Immunohistochemistry and Flow Cytomerty. *Am.n J. Pathol.* 159(1):63–69 (Jul. 2001).

Gygl et al. Correlation between Protein and mRNA Abundance in Yeast. *Mol. Cell Biol.* 19(3):1720–1730 (Mar. 1999).

Hacia et al. Detection of heterozygous mutations in BRCA1 using high density oligonucleotide arrays and two–colour fluorescence analysis. *Nat. Genet.* 14:441–447 (Dec. 1996).

Hagiwara et al. Quantitation of Hepatitis C Virus RNA in Serum of Asymptomatic Blood Donors and Patients with Type C Chronic Liver Disease. *Hepatology* 17(4)545–550 (Apr. 1993).

Hall et al. Nucleotide. Part XLI. Mixed Anhydrides as Intermediates in the Synthesis of Dinucleoside Phosphates. *J. Chem. Soc.* 3291–3296 (1957).

Hall et al. From the Cover: Sensitive detection of DNA polymorphisms by the serial invasive signal amplification reaction. *Proc. Natl. Acad. Sci. USA* 97(15):8272–8277 (Jul. 2000).

Hanvey et al. Antisense and Antigene Properties of Peptide Nucleic Acids. *Science* 258:1481–1485 (Nov. 27, 1992).

Hata et al. Structure of the Human Ornithine Transcarbamylase Gene. *J. Biochem.* 103:302–308 (1988).

Heinonen et al. Simple triple–label detection of seven cystic fibrosis mutations by time–resolved fluorometry. *Clin. Chem.* 43(7):1142–1150 (1997).

Hendrickson et al. High sensitivity multianalyte immunoassay using covalent DNA–labeled antibodies and polymerase chain reaction. *Nucl. Acids Res.* 23(3):522–529 (1995).

Henegariu et al. Custom fluorescent–nucleotide synthesis as an alternative method for nucleic acid labeling. *Nat. Biotech.* 18:345–346 (Mar. 2000).

Hoeltke et al. Multiple Nucleic Acid Labeling and Rainbow Detection. *Anal. Biochem.* 207:24–31 (1992).

Holland et al. Detection of specific polymerase chain reaction product by utilizing the 5'→3' exonuclease activity of *Thermus aquaticus* DNA polymerase. *Proc. Natl. Acad. Sci. USA* 88:7276–7280 (Aug. 1991).

Holloway et al. An exonuclease–amplification coupled capture technique improves detection of PCR product. *Nucl. Acids Res.* 21(16):3905–3906 (1993).

Hoy et al. Bromodeoxyuridine/DNA analysis of replication in CHO cells after exposure to UV light. *Mutat. Res.* 290:217–230 (1993).

Hsuih et al. Quantitative detection of HCV RNA using novel ligation–dependent polymerase chain reaction. *American Association for the Study of Liver Diseases.* (Chicago, IL, Nov. 3–7, 1995) [poster abstract].

Humphery–Smith and Blackstock. Proteome Analysis: Genomics via the Output Rather than the Input Code. *J. Protein Chem.* 16(5):537–544 (1997).

Itakura et al. Synthesis and Use of Synthetic Oligonucleotides. *Annu. Rev. Biochem.* 53:323–356 (1984).

Iyer et al. 3H–1,2–benzodithiole–3–one 1, 1–Dioxide as an Improved Sulfurizing Reagent in the Solid–Phase Syntesis of Oligodeoxyribonucleotide Phosphorotioates. *J. Am. Chem. Soc.* 112:1253–1254 (1990).

Jacobson et al. The N–Terminal Amino–Acid Sequences of DNA Polymerase I from *Escherichia coli* and of the Large and the Small Fragments Obtained by a Limited Proteolysis. *Eur. J. Biochem.* 45:623–627 (1974).

Jiang et al. An efficient method for generation and subcloning of tandemly repeated DNA sequences with defined length, orientation and spacing. *Nucl. Acids Res.* 24(16):3278–3279 (1996).

Jónsson et al. Sequence of the DNA ligase–encoding gene from thermus scotoductus and conserved motifs in DNA ligases. *Gene* 151:177–180 (1995).

Jung et al. Bacteriophage PRDI DNA polymerase: Evolution of DNA polymerases. *Proc. Natl. Acad. Sci. USA* 84:8287–8291 (1987).

Kabanov et al. A new class of antivirals: antisense oligonucleotides combined with a hydrophobic substituent effectively inhibit influenze virus reproduction and synthesis of virus–specific proteins in MDCK cells. *FEBS Lett.* 259(2):327–330 (1990).

Kaboord et al. Accessory proteins function as matchmakers in the assembly of the T4 DNA polymerse holoenzyme. *Curr. Biol.* 5(2):149–157 (1995).

Kälin et al. Evaluation of the ligase chain reaction (LCR) for the detection of point mutations. *Mutat. Res.* 283(2):119–128 (1992).

Kaplan et al. Rapid Photolytic of Adenosine 5'–Triphosphate from a Protected Analogue: Utilization by the Na:K Pump of Human Red Blood Cell Ghosts. *Biochemistry* 17:1929–1935 (1978).

Kellogg et al. TaqStart Antibody: "Hot Start" PCR facilitated by a neutralizing monoclonal antibody directed against Taq DNA polymerase. *BioTechniques.* 16(6):1134–1137 (1994).

Kerkhof. A Comparison of Substrates for Quantifying the Signal fron a Nonradiolabeled DNA Probe. *Anal. Biochem.* 205:359–364 (1992).

Kessler. The digoxigenin:anti–dioxgenin (DIG) technology—a survey on the concept and realization of a novel bioanalytical indicator system. *Mol. Cell Probes* 5:161–205 (1991).

Khrapko et al. Hybridization of DNA with oligonucleotides immobilized In gel: a convenient method for detecting single base substitutions. *Mol. Biol. (Mosk) (USSR).* 25:718–730 (1991).

Kimpton et al. Automated DNA Profiling Employing Multiplex Amplification of Short Tandom Repeat Loci. *PCR Methods and Applications.* 3:13–22 (1993).

King et al. Bridgning the Gap. Joining of nonhomologous ends by DNA polymerases. *J. Biol. Chem.* 269(18):13061–13064 (May 6, 1994).

Kong et al. Characterization of a DNA Polymerase from the Hyperthermophile Archaea *Thermococcus litoralis. J. Biol. Chem.* 268(3):1965–1975 (1993).

Kool. Circular Oligonucleotides: New Concepts in Oligonucleotide Design. *Annu. Rev. Biomol. Struct.* 25:1–28 (1996).

Kunkel et al. Rapid and Eficient Site–Specific Mutagenesis without Phenotypic Selection. *Meth. Enzymol.* 154:367–382 (1987).

Kwoh et al. Transcription–based amplification system and detection of amplified human immunodeficiency virus type 1 with a bead–based sandwich hybridization format. *Proc. Natl. Acad. Sci. USA* 86:1173–1177 (Feb. 1989).

Lamture et al. Direct detection of nucleic acid hybridization on the surface of a charge coupled device. *Nucl. Acids Res.* 22(11):2121–2125 (1994).

Landegren et al. A Ligase–Mediated Gene Detection Technique. *Science* 241:1077–1080 (Aug. 26, 1988).

Landegren. Molecular mechanics of nucleic acid sequence amplification. *Trends Genetics.* 9(6):199–202 (Jun. 1993).

Langer et al. Enzymatic synthesis of biotin–labeled polynucleotides: novel nucleic acid affinity probes. *Proc. Natl. Acad. Sci. USA* 78(11):6633–6637 (Nov. 1981).

Lawyer et al. High–level Expression, Purification, and Enzymatic Characterization of Full–length *Thermus aquaticus* DNA Polymerase and a Truncated Form Deficient in 5+ to 3' Exonuclease Activity. *PCR Methods Applications* 2(4):275–287 (1993).

LaFrere et al. Towards a new predictor of AIDS progression through the quantitation of HIV–1 DNA copies by PCR in HIV–infected individuals. *Br. J. Haematol.* 82(2):467–471 (1992).

Lesnick and Freier. Relative Thermodynamic Stability of DNA, RNA, and DNA:RNA Hybrid Duplexes: Relationship with Base Composition and Structure. *Biochemistry* 34:10807–10815 (1995).

Letsinger et al. Cholesteryl–conjugated oligonucleotides: Synthesis, properties, and activity as inhibitors of replication of human immunodeficiency virus in cell culture. *Proc. Natl. Acad. Sci. USA* 86:6553–6556 (Sep. 1989).

Letsinger et al. Synthesis of Thymidine Oligonucleotides by Phosphite Triester Intermediates. *J. Am. Chem. Soc.* 9:3655–3661 (Jun. 9, 1981).

Letsinger and Wu. Use of a Stilbenedicarboxamide Bridge in Stabilizing, Monitoring, and Photochemically Altering Folded Conformations of Oligonucleotides. *J. Am. CheM. Soc.* 117:7323–7328 (1995).

Lichter et al. High–Resolution Mapping of Human Chromosome 11 by in Situ Hybridization with Cosmid Clones. *Science* 247:64–69 (Jan. 5, 1990).

Little et al. Strand Displacement Amplification and Homogeneous Real–Time Detection Incorporated in a Second-–Generation DNA Probe System, BDProbeTectET. *Clin. Chem.* 45(6):777–784 (1999).

Liu et al. Rolling Circle DNA Synthesis: Small Circular Oligonucleotides as Efficient Templates for DNA Polymerases. *J. Am. Chem. Soc.* 118:1587–1594 (1996).

Lizardi et al. Mutation detection and single–molecule counting using isothermal rolling–circle amplification. *Nat. Genet.* 19:225–232 (Jul. 1998).

Loakes et al. 5–Nitroindole as an univeral base analogue. *Nucl. Acids Res.* 22(20):4039–4043 (1994).

Lockhart et al. Expression monitoring by hybridization to high–density oligonucleotide arrays. *Nat. Biotechnol.* 14:1675–1680 (Dec. 1996).

Lu et al. High Concentration of Peripheral Blood Mononuclear Cells Harboring Infectious Virus Correlates with Rapid Progression of Human Immunodeficiency Virus Type–1 Related Diseases. *JID* 168(5):1165–8116 (Nov. 1993).

Lukyanov et al. Molecule by molecule PCR amplification of complex DNA mixtures for direct sequencing: an approach to in vitro cloning. *Nucl. Acids Res.* 24(11):2194–2195 (1996).

Luo et al. Improving the fidelity of thermus thermophilus DNA ligase. *Nucl. Acids Res.* 24(14):3071–3078 (1996).

Manoharan et al. Chemical Modifications to Improve Uptake and Bioavailability of Antisense Oligonucleotides. *Ann. NY Acad. Sci.* 660:306–309 (1992).

Manoharan et al. Cholic Acid–Oligonucleotide Conjugate for Antisense Applications. *Bioorg. Med. Chem. Lett.* 4(8):1053–1060 (1994).

Manoharan et al. Introduction of a lipophilic thioether tether in the minor groove of nucleic acids for antisense applications. *Bioorg. Med. Chem. Lett.* 3(12):2765–2770 (1993).

Manoharan et al. Lipidic Nucleic Acids. *Tetra. Lett.* 36(21):3651–3654 (1995).

Manoharan et al. Oligonucleotide conjugates: alteration of the pharmacokinetic properties of antisense agents. *Nucleosides & Nucleotides.* 14(3–5):969–973 (1995).

Marshall et al. Detection of HCV RNA by the Asymmetric Gap Ligase Chain Reaction. *PCR Methods and Applications.* 4:80–84 (1994).

Maskos et al. Oligonucleotide hybridizations on glass supports: a novel linker for oligonucleotide synthesized in situ. *Nucl. Acids Res.* 20(7):1679–1684 (1992).

Matsumoto et al. Primary structure of bacteriophage M2 DNA polymerase: conserved segments within protein–priming DNA polymerases and DNA polymerase I of *Escherichia coli. Gene* 84(2):247–255 (1989).

Matteucci et al. Synthesis of Deoxyoligonucleotides on a Polymer Support. *J. Am. Chem. Soc.* 103:3185–3191 (1981).

McCray et al. A new approach to time–resolved studies of ATP–requiring biological systems: laser flash photolysis of caged ATP. *Proc. Natl. Acad. Sci. USA* 77(12):7237–7241 (Dec. 1980).

McGraw et al. Sequence–dependent oligonucleotide–target duplex stabilities: rules from empirical studies with a set of twenty–mers. *Biotechniques.* 8(6):674–678 (1990).

Melton et al. Efficient in vitro synthesis of biologically active RNA and RNA hybridization probes from plasmids containing a bacteriophage SP6 promoter. *Nucl. Acids Res.* 12(18):7035–7056 (1984).

Metzker et al. Termination of DNA synthesis by novel 3'–modified–deoxyribonucleoside 5'–triphosphtes. *Nucl. Acids Res.* 22(20):4259–4267 (1994).

Mujumdar et al. Cyanine Dye Labeling Reagents Containing Isothiocyanate Groups. *Cytometry* 10:11–19 (1989).

Mullenix et al. Allergen–specific IgE Detection on Microarrays Using Rolling Circle Amplification: Correlation with in Vitro Assays for Serum IgE. *Clin. Chem.* 47(10):1926–1929 (2001).

Nallur et al. Signal amplification by rolling circle amplification on DNA microarrays. *Nucl. Acids. Res.* 29(23):e118.

Narang et al. Chemical Synthesis of Deoxynucleotides by the Modified Tester Method. *Meth. Enzymol.* 65:610–620 (1980).

Nazerenko et al. A closed tube format for amplification and detection of DNA based on energy transfer. *Nucl. Acids Res.* 25:2516–2521 (Jun. 1997).

Newton et al. Analysis of any point mutation in DNA. The amplification refractory mutation system (ARMS). *Nucl. Acids Res.* 17(7):2503–2516 (1989).

Nichols et al. A universal nucleoside for use at ambiguous sites in DNA primers. *Nature.* 369(6480):492–493 (Jun. 9, 1994).

Nielsen et al. Peptide Nucleic Acid (PNA). A DNA Mimic with a Peptide Backbone. *Bioconj. Chem.* 5:3–7 (1994).

Nielsen et al. Peptide nucleic acids (PNAs): Potential anti-sense and anti-gene agents. *Anti–Cancer Drug Design.* 8:53–63 (1993).

Nielsen et al. Sequence–Selective Recognition of DNA by Strand Displacement with a Thymine–Substituted Polymide. *Science* 254:1497–1500 (Dec. 1991).

Nikiforov et al. Genetic Bit Analysis: a solid phase method for typing single nucleotide polymorphisms. *Nucl. Acids Res.* 22(20):4167–4175 (1994).

Nikiforov et al. The Use of Phosphorothioate Primers and Exonuclease Hydrolysis for the Preparation of Single–stranded PCR Products and their Detection by Solid-phase Hybridization. *PCR Meth. Appl.* 3:285–291 (1994).

Nilsson et al. Padlock probes reveal single–nucleotide differences, parent of origin and in situ distribution of centromeric sequences in human chromosomes 13 and 21. *Nat. Genet.* 16:252–255 (Jul. 1997).

Nilsson et al. Padlock Probes: Circularizing Oligonucleotides for Localized DNA Detection. *Science* 265(5181):2085–2088 (Sep. 30, 1994).

Nuovo et al. In Situ Amplification Using Universal Energy Transfer–labeled Primers. *J. Histochem. Cytochem.* 47(3):273–279 (1999).

Oberhauser et al. Effective incorporation of 2'–O–methyl-oligoribonucleotides into liposomes and enhanced cell association through modification with thiocholesterol. *Nucl. Acids Res.* 20(3):533–538 (1992).

Oda et al. Accurate quantitation of protein expression and site–specific phosphorylation. *Proc. Natl. Acad. Sci. USA* 96:6591–6596 (1999).

Panasenko et al. A Simple, Three–Step Procedure for the Large Scale Purification of DNA Ligase from a Hybrid λ Lysogen Constructed in Vitro. *J. Biol. Chem.* 253(13):4590–4592 (Jul. 10, 1978).

Parker et al. Targeted gene walking polymerase chain reaction. *Nucl. Acids Res.* 19(11):3055–3060 (1991).

Patton et al. Components of the Protein Synthesis and Folding Machinery Are Induced in Vascular Smooth Muscle Cells by Hypertrophic and Hyperplastic Agents. *J. Biol. Chem.* 270(36):21404–21410 (Sep. 8, 1995).

Patton. Making Blind Robots See: The Synergy Between Fluorscent Dyes and Imaging Devices in Automated Proteomics. *Biotechniques* 28(5):944–957 (2000).

Patton. Proteome analysis II. Protein subcellar redistribution: linking physiology to genomics via the proteome and separation techniques involved. *J Chromatogr. B* 722:203–223 (1999).

Pease et al. Light–generated oligonucleotide arrays for rapid DNA sequence analysis. *Proc. Natl.Acad. Sci. USA* 91(11):5022–5026 (May 1994).

Piatak et al. High Levels of HIV–1 in Plasma During All Stages of Infection Determined by Competitive PCR. *Science* 259:1749–1754 (Mar. 19, 1993).

Pillai. Photoremovable Protecting Groups in Organic Synthesis. *Synthesis* 1–26 (1980).

Pless and Letsinger. Solid support synthesis of oligothymidylates using phosphorochloridates and 1–alkylimidazoles. *Nucl. Acids Res.* 2(6):773–786 (Jun. 1975).

Pokrovskaya et al. In Vitro transcription: Preparative RNA Yields in Analytical Scale Reactions. *Anal. Biochem.* 220:420–423 (1994).

Porstmann et al. Quantitation of 5–Bromo–2–Deoxyuridine Incorporation into DNA: an Enzyme Immunoassay for the Assessment of the Lymphiod Cell Proliferative. *J. Immunol. Meth.* 82:169–179 (1985).

Prakash and Kool. Structural Effects in the Recognition of DNA by Circular Oligonucleotides. *J. Amer. Chem. Soc.* 114:3523–3527 (1992).

Prober et al. A System for Rapid DNA Sequencing with Fluorscent Chain–Terminating Dideoxynucleotides. *Science* 238:336–341 (1987).

Ramsing et al. Helix–Coli Transsition of Parallel–Stranded DNA. Thermodynamics of Hairpin and Linear Duplex Oligonucleotides. *Biochemistry* 28:9528–9535 (1989).

Richards et al. Conditional Mutator Phenotypes In hMSH2–Deficient Tumor Cells Lines. *Science* 277:1523–1526 (Sep. 5, 1997).

Ried et al. Simultaneous visualization of seven different DNA probes by in situ hybridization using combinational fluorescence and digital imaging microscopy. *Proc. Natl. Acad. Sci. USA* 89(4):1388–1392 (1982).

Rigler et al. Difference in the Mechanism of Stimulation of T7 DNA Polymerase by Two Binding Modes of *Escherichia coli* Single–stranded DNA–binding Protein. *J. Biol. Chem.* 270(15):8819–8919 (Apr. 14, 1995).

Rychlik et al. Optimization of the annealing temperature for DNA amplification in vitro. *Nucl. Acids Res.* 18(21):6409–6412 (1990).

Rys et al. Preventing False Positives: Quantitative Evaluatio of Three Protocols for Inactivation of Polymerase Chain Reaction Amplication Products. *J. Clin. Microbiol.* 31(9):2356–2360 (Sep. 1993).

Saiki et al. Primer–Directed Enzymatic Amplification of DNA with a Thermostable DNA Polymerase. *Science* 239:487–491 (Jan. 29, 1988).

Saison–Behmoaras et al. Short modified antisense oligonucleotides directed against Ha–ras point mutation induce selective cleavage of the mRNA and inhibit T24 cells proliferation. *EMBO J.* 10(5):1111–1118 (1991).

Saksela et al. Human immunodeficiency virus type 1 mRNA expression in peripheral blood cells predicts disease progression independently of the numbers of CD4+ lymphocytes. *Proc. Natl. Acad. Sci. USA* 91(3):1104–1108 (1994).

Sanghvi. Heterocyclic base modifications in nucleic acids and their applications in antisense oligonucleotides. *Antisense Research and Applications.* (Crooke et al, eds., CRC Press) Chapters 15–16, pp. 273–301 (1993).

Sano et al. Detection of heavy methylation in human repetitive DNA subsets by a monoclonal antibody against 5–methylcytosine. *Biochim. Biophys. Acta.* 951:157–165 (1988).

Saris et al. Blotting of RNA onto RNA exchange paper allowing subsequent characterization by in situ translation in addition to blot hybridization. *Nucl. Acids Res.* 10(16):4831–4843 (1982).

Schena et al. Parallel human genome analysis: Microarray–based expression monitoring of 1000 genes. *Proc. Natl. Acad. Sci. USA* 93:10614–10619 (Oct. 1994).

Schena et al. Quantitative Monitoring of Gene Expression Patterns with s Complementary DNA Microarray. *Science* 270:467–470 (Oct. 20, 1995).

Schenborn et al. A novel transcription property of SP6 and T7 RNA polymerases: dependence on template structure. *Nucl. Acids Res.* 13(17):6223–6236 (1985).

Schwarz. Improved yields of long PCR products using gene 32 protein. *Nucl. Acids Res.* 18(4):1079 (1990).

Schweitzer and Kingsmore. Combining nucleic acid amplification and detection. *Curr. Opin. Biotech.* 12(1):21–27 (Feb. 2001).

Schweitzer et al. Immunoassays with rolling circle DNA amplification: a versatile platform for ultrasensitive antigen detection. *Proc. Natl. Acad. Sci. USA* 97(18):10113–10118 (Aug. 29, 2000).

Schweitzer et al. Multiplexed protein profiling on microarrays by rolling–circle amplification. *Nat. Biotech.* 20:359–365 (2002).

Shea et al. Synthesis, hybridization properties and antiviral activity of lipid–oligodeoxynucleotide conjugates. *Nucl. Acids Res.* 18(13):3777–3783 (1990).

Shumaker et al. Mutation Detection by Solid Phase Primer Extension. *Hum. Mutat.* 7(4):346–354 (1996).

Siegal et al. A Novel DNA Helicase from Calf Thymus. *J. Biol. Chem.* 267(19):13629–13635 (Jul. 5, 1992).

Simpson. The Natural Somatic Mutation Frequency and Human Carcinogenesis. *Adv. Cancer Res.* 71:209–240 (1997).

Skaliter et al. Rolling circle DNA replication in vitro by a complex of herpes simplex virus type 1–encoded enzymes. *Proc. Natl. Acad. Sci. USA* 91(22):10665–10669 (Oct. 1994).

Speicher et al. Karyotyping human chromosomes by combinatorial multi–fluor FISH. *Nat. Genet.* 12(4):368–375 (1996).

Stimpson et al. Real–time detection of DNA hybridization and metling on oligonucleotide arrays by using optical wave guides. *Proc. Natl. Acad. Sci. USA* 92(14):6379–6383 (Jul. 1995).

Strauss et al. Quantitative measure of calretinin and β–actin mRNAIN rat brain micropunches without prior isolation of RNA. *Mol. Brain Res.* 20:229–239 (1993).

Studier et al. Use of T7 RNA Polymerase to Direct Expression of Cloned Genes. *Meth. Enzymol.* 185:60–89 (1990).

Stump et al. The use of modified primers ot eliminate cycle sequencing artifacts. *Nucl. Acids Res.* 27(23):4642–4648 (1999).

Svinarchuk et al. Inhibition of HIV proliferation in MT–4 cells by antisense oligonucleotide conjugated to lipophilic groups. *Biochimie.* 75:49–54 (1993).

Syvänen et al. Fast quantification of nucleic acid hybrids by affinity–based hybrid collection. *Nucl. Acids Res.* 14(12):5037–5049 (1986).

Tabor et al. Selective Inactivation of the Exonuclease Activity of Bacteriophage T7 DNA Polymerase by in Vitro Mutagenesis. *J. Biol. Chem.* 264(11):6447–6458 (Apr. 15, 1989).

Tabor and Richardson. Selective Oxidation of the Exonuclease Domain of Bacteriophage T7 DNA Polymearase. *J. Biol. Chem.* 262(32):15330–15333 (Nov. 15, 1987).

Thelwell et al. Mode of action and application of Scorpion primers to mutation detection. *Nucl. Acids Res.* 28(19):3752–3761 (2000).

Thomas et al. Cascade rolling circle amplification, a homogeneous fluorescence detection system for DNA diagnostics. *Clin. Chem.* 43:2219, Abs. 38 (1997).

Thorbjarnardottir et al. Cloning and sequence analysis of the DNA ligase–encoding gene of *Rhodothermus marinus*, overproduction, purification and characterization of two thermophilic DNA ligases. *Gene* 161:1–6 (1995).

Tsurumi et al. Functional Interaction between Epstein–Barr Virus DNA Polymerase Catalytic Subunit and Its Accessory Subunit In Vitro. *J. Virol.* 67(12):7648–7653 (Dec. 1993).

Tyagi and Kramer. Molecular Beacons: Probes that Fluoresce upon Hybridization. *Nat. Biotech.* 14:303–308 (Mar. 1996).

Tyagi et al. Extremely sensitive, background–free gene detection using binary probes and Qβ replicase. *Proc. Natl. Acad. Sci. USA* 93:5395–5400 (May 1996.

Uemori et al. Cloning of the DNA Polymerase Gene of *Bacillus caldotenax* and Characterizaion of the Gene Product. *J. Biochem.* 113:401–410 (1993).

Velculescu et al. Serial Analysis of Gene Expression. *Science* 270:484–487 (Oct. 20, 1995).

Vellemain et al. The N–Terminal B–Domain of T4 Gene 32 Protein Mdulates the Lifetime of Cooperatively Bound Gp32–ss Nucleic Acid Complexes. *Biochemistry* 35:14395–14404 (1996).

Vogelstein et al. Supercoiled Loops and Eucaryotic DNA Replication. *Cell* 22:79–85 (Nov. 1980).

Voisey et al. Interrogation of Multimeric DNA Amplification Products by Competitive Primer Extension Using Bst DNA Polymerase (Large Fragment). *Biotechniques* 31(5):1122–1129 (Nov. 2001).

Waggoner. Covalent Labeling of Proteins and Nucleic Acids With Fluorophores. *Meth. Enzymol.* 246:362–373 (1995).

Walker and Linn. Detection of *Mycobacterium tuberculosis* DNA with thermophilic strand displacement amplification and fluorescence polarization. *Clin. Chem.* 42(10):1604–1608 (1996).

Walker et al. Isothermal in vitro amplification of DNA by a restriction enzyme/DNA polymerase system. *Proc. Natl. Acad. Sci. USA* 89:392–396 (Jan. 1992).

Walker et al. Strand displacement amplification—an isothermal, in vitro DNA amplification technique. *Nucl. Acids Res.* 20(7):1691–1696 (1992).

Walter and Strunk. Strand displacement amplification as an in vitro model for rolling–circle replication: deletion formation and evolution during serial transfer. *Proc. Natl. Acad. Sci. USA* 91:7937–7941 (Aug. 1994).

Wang and Kool. Circular RNA oligonucleotide. Synthesis, nucleic acid binding properties, and a comparison with circular DNAs. *Nucl. Acids. Res.* 22(12):2326–2333 (1994).

Wang et al. Large–Scale Identification, Mapping, and Genotyping of Single–Nucleotide Polymorphisms in the Human Genome. *Science* 280:1077–1082 (May 15, 1998).

Wansink et al. Fluorescent Labeling of Nascent RNA Reveals Transcription by RNA Polymerase II in Domains Scattered Throughout the Nucleus. *J. Cell Biol.* 122(2):283–293 (Jul. 1993).

Wiedmann et al. Ligase chain reaction (LCR)—overview and applications. *PCR Methods and Applications.* (Cold Spring Harbor Laboratory Press, Cold Spring Harbor, NY, 1994) [pp. S51–S64].

Winn–Deen et al. Non–radioactive detection of *Mycobacterium tuberculosis* LCR products in a microtitre plate format. *Mol. Cell Probes* (England) 7(3):179–186 (1993).

Wirth and Romano. Staining methods in gel electrophoresis, including the use of multiple detection methods. *J. Chromatogr. A.* 698:123–143 (1995).

Young et al. Quantitative Analysis of Solution Hybridization. *Nucleic Acid Hybridisation: A Practical Approach.* (IRL Press, 1985) pp. 47–71.

Yu et al. Cyanine dye dUTP analogs for enzymatic labeling of DNA probes. *Nucl. Acids Res.* 22(15):3226–3232 (1994).

Zehavi et al. Light–Sensitive Glycosides. I. 6–Nitroveratryl β–D–Glucopyranoside and 2–Nitrobenzyl β–D–Glucopyranoside. *J. Org. Chem.* 37(14):2281–2288 (1972).

Zhang et al. Whole genome amplification from a single cell: Implications for genetic analysis. *Proc. Natl. Acad. Sci. USA* 89:5847–5851 (Jul. 1992).

Zhu et al. Gloval Analysis of Protein Activities Using Proteome Chips. *Science* 293:2101–2105 (Sep. 14, 2001).

Zhu et al. Purification and characteriation of PRD1 DNA polymerase. *Biochimica Biophysics Acta.* 1219(2):267–276 (1994).

Zijderveld et al. Helix–Destabilizing Properties of the Adenovirus DNA–Binding Protein. *J. Virol.* 68(2):1158–1164 (Feb. 1994).

* cited by examiner

SEQUENCE LISTING

```
<160> NUMBER OF SEQ ID NOS: 6

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Note =
      synthetic construct

<400> SEQUENCE: 1
gtgcggccgc tttttttttt tttttttttt                                      30

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Note =
      synthetic construct
<220> FEATURE:
<221> NAME/KEY: misc_feature
<222> LOCATION: 15-20
<223> OTHER INFORMATION: n=a,t,c,or g

<400> SEQUENCE: 2
aaaagcggcc gcacnnnnnn                                                 20

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: Note =
```

-continued

```
      synthetic construct
<220> FEATURE:
<221> NAME/KEY: misc_feature
<222> LOCATION: 31-32
<223> OTHER INFORMATION: n=a,t,c,or g

<400> SEQUENCE: 3
gtgcggccgc tttttttttt tttttttttt nn                          32

<210> SEQ ID NO 4
<211> LENGTH: 13
<212> TYPE: DNA
<213> ORGANISM: Artificial Sequence
<220> FEATURE:
<223> OTHER INFORMATION: Description of Artificial Sequence: Note =
      synthetic construct

<400> SEQUENCE: 4
aaaaaaaaaa aaa                                               13

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Note =
      synthetic construct
<220> FEATURE:
<221> NAME/KEY: misc_feature
<222> LOCATION: 14-19
<223> OTHER INFORMATION: n=a,t,c,or g

<400> SEQUENCE: 5
aaagcggccg cacnnnnnn                                         19

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Note =
      synthetic construct

<400> SEQUENCE: 6
tttttttttt tttttttttt tt                                     22
```

ROLLING CIRCLE AMPLIFICATION OF RNA

FIELD OF THE INVENTION

The present invention is in the field of nucleic acid amplification, and specifically in the area of rolling circle amplification of RNA molecules.

BACKGROUND OF THE INVENTION

Numerous nucleic acid amplification techniques have been devised, including strand displacement cascade amplification (SDCA)(referred to herein as exponential rolling circle amplification (ERCA)) and rolling circle amplification (RCA)(U.S. Pat. No. 5,854,033; PCT Application No. WO 97/19193; Lizardi et al., Nature Genetics 19(3):225–232 (1998)); multiple displacement amplification (MDA)(PCT Application WO 99/18241); strand displacement amplification (SDA)(Walker et al., Nucleic Acids Research 20:1691–1696 (1992), Walker et al., Proc. Natl. Acad. Sci. USA 89:392–396 (1992)); polymerase chain reaction (PCR) and other exponential amplification techniques involving thermal cycling, self-sustained sequence replication (3SR), nucleic acid sequence based amplification (NASBA), and amplification with Qβ replicase (Birkenmeyer and Mushahwar, J. Virological Methods 35:117–126 (1991); Landegren, Trends Genetics 9:199–202 (1993)); and various linear amplification techniques involving thermal cycling such as cycle sequencing (Craxton et al., Methods Companion Methods in Enzymology 3:20–26 (1991)).

Rolling Circle Amplification (RCA) driven by DNA polymerase can replicate circular oligonucleotide probes with either linear or geometric kinetics under isothermal conditions (Lizardi et al., Nature Genet. 19: 225–232 (1998); U.S. Pat. Nos. 5,854,033 and 6,143,495; PCT Application No. WO 97/19193). If a single primer is used, RCA generates in a few minutes a linear chain of hundreds or thousands of tandemly-linked DNA copies of a target that is covalently linked to that target. Generation of a linear amplification product permits both spatial resolution and accurate quantitation of a target. DNA generated by RCA can be labeled with fluorescent oligonucleotide tags that hybridize at multiple sites in the tandem DNA sequences. RCA can be used with fluorophore combinations designed for multiparametric color coding (PCT Application No. WO 97/19193), thereby markedly increasing the number of targets that can be analyzed simultaneously. RCA technologies can be used in solution, in situ and in microarrays. In solid phase formats, detection and quantitation can be achieved at the level of single molecules (Lizardi et al., 1998). Ligation-mediated Rolling Circle Amplification (LM-RCA) involves circularization of a probe molecule hybridized to a target sequence and subsequent rolling circle amplification of the circular probe (U.S. Pat. Nos. 5,854,033 and 6,143,495; PCT Application No. WO 97/19193). Very high yields of amplified products can be obtained with exponential (or cascade) rolling circle amplification (U.S. Pat. Nos. 5,854,033 and 6,143,495; PCT Application No. WO 97/19193) and multiply-primed rolling circle amplification (Dean et al., Genome Research 11:1095–1099 (2001)).

Change in cellular function is related to the changes in the expression pattern of different proteins. Thus, valuable information about cellular function is often obtained by comparing the expression of specific proteins between two stages of cell growth, or function (Zhu et al., "Global analysis of protein activities using proteins chips." Science 293(5537): 2101–5 (2001); Schweitzer and Kingsmore, "Measuring proteins on microarrays." Curr. Opin. Biotechnol. 13(1): 14–9 (2002); Schweitzer et al., "Multiplexed protein profiling on microarrays by rolling-circle amplification." Nat. Biotechnol. 20(4): 359–65 (2002)). This endeavor is referred to as expression profiling. Since protein expression profiling studies are mostly dependent on the availability of protein specific antibodies, many of the gene expression-profiling studies are, therefore, carried out at the level of mRNA expression (Colantuoni et al., "Gene expression profiling in postmortem Rett Syndrome brain: differential gene expression and patient classification." Neurobiol. Dis. 8(5): 847–65 (2001); Colantuoni et al., "High throughput analysis of gene expression in the human brain." J. Neurosci. Res. 59(1): 1–10 (2000)). Thus, important information about the disease process or treatment regime can be obtained by evaluating the relative expression of a gene in two different cellular environments (for example, cancer vs. normal tissue, or drug treated vs. non-treated states). Current high throughput expression profiling studies often are carried out on DNA micro-arrays. Gene specific DNA probes are anchored on to glass slides and fluorescent cDNA or amplified cDNA (from the RNA sample) is hybridized to these anchored probes and detected. Utilization of DNA microarrays is expected to provide advances in identifying genetic profile of human diseases by the acquired ability to screen thousands of individual genes that may be expressed differentially between two samples (Colantuoni et al. (2000); Colantuoni et al. (2001); Nallur et al., "Signal amplification by rolling circle amplification on DNA microarrays." Nucleic Acids Res. 29(23): E118 (2001)). Typically, these assays require 5–100 μg of total RNA for a single analysis. Millions of cells are, therefore, required to obtain sufficient RNA sample for expression profiling experiments with unamplified RNA samples. Often only a few cells that were acquired by aspiration needle biopsies, rare population subsets isolated by cell sorting, laser capture micro dissections or micro manipulated single cells, are available for expression profiling experiments. In such instances only small quantities of RNA becomes available for expression profiling experiments. Therefore, many high throughput expression-profiling studies need to be carried out using amplified cDNA samples. However, most current cDNA amplification technologies have shortcomings that result in amplification bias. Therefore, there is a need for a method for reliable, universal, unbiased transcript amplification.

BRIEF SUMMARY OF THE INVENTION

Disclosed are compositions and methods for amplification of RNA molecules. The disclosed method involves synthesizing first strand cDNA molecules from RNA molecules, circularizing the first strand cDNA molecules and replicating the circularized first strand cDNA molecules using rolling circle replication. The method can be aided by the use of specialized primers for cDNA synthesis and specialized probes for circularizing the first strand cDNA molecules. The method can be used to replicate and amplify multiple RNA molecules, such as all RNA molecules in a sample or all mRNA molecules in a sample, or be used to replicate and amplify specific RNA molecules. Rolling circle replication of the circularized first strand cDNA molecules results in long DNA strands containing tandem repeats of the cDNA sequence. The tandem sequence DNA strand produced by rolling circle replication corresponds to the positive strand of the DNA from which the corresponding RNA was replicated.

The tandem sequence DNA can be used directly (for detection of sequences, for example), further amplified, or used any other purpose. The tandem sequence DNA also can be made double-stranded. Double-stranded tandem sequence DNA can be used, for example to produce unit lengths of the cDNA sequence making up the tandem sequence DNA. Production of unit length cDNA molecules can be aided by including a cleavage site, such as the recognition site for a restriction enzyme, in the cDNA primer and/or circularization probe. The double-stranded tandem sequence DNA and, especially, the unit lengths of cDNA sequence can be cloned using recombinant DNA techniques and materials. Tandem sequence DNA and tandem sequence DNA fragments, including unit length cDNA molecules, can constitute a cDNA library.

Tandem sequence DNA can also be transcribed to produce transcripts having sequence complementary to or matching the sequence of RNA molecules. The tandem sequence DNA can be transcribed directly to produce long RNA molecules, referred to as tandem sequence transcripts, made up of tandem repeats of the RNA sequence (or its complement). Unit length cDNA molecules can also be transcribed to produce RNA molecules, referred to as tandem repeat transcripts, containing a single RNA sequence (or its complement).

Further amplification of the cDNA sequences can be accomplished using any suitable replication or amplification technique. Useful amplification techniques include rolling circle amplification techniques such as multiply-primed rolling circle amplification and exponential rolling circle amplification. Rolling circle replication and rolling circle amplification of the circularize first strand cDNA molecules can also be combined with multiple strand displacement amplification and other amplification techniques to produce specialized amplification products and/or to further increase the amplification yield.

In another form of the disclosed method, first strand cDNA molecules can be ligated together to form concatemers. These first strand cDNA concatemers can be amplified via multiple strand displacement amplification. First strand cDNA concatemers that are circularized can be amplified via rolling circle replication. Rolling circle replication of circular first strand cDNA molecules and/or first strand cDNA concatemers can be carried out simultaneously with multiple strand displacement amplification of uncircularized first strand cDNA molecules and/or uncircularized first strand cDNA concatemers.

The disclosed amplification of RNA molecules is useful for producing nucleic acid molecules corresponding to RNA molecules in an RNA sample. The disclosed method is a general purpose technique for amplifying RNA sequences and the nucleic acid molecules produced can be used for any purpose. Useful purposes include, for example, detecting specific RNA molecules and/or sequences, detecting a population or set of RNA molecules and/or sequences, analyzing or sequencing specific RNA molecules and/or sequences, analyzing or sequencing a population or set of RNA molecules and/or sequences, cataloging a population or set of RNA molecules and/or sequences, cloning specific RNA molecules and/or sequences, and cloning a population or set of RNA molecules and/or sequences. Thus, for example, the disclosed method can be used to identify or analyze the RNA molecules and/or sequences expressed in different cells, tissues, and/or samples, and compare the RNA molecules and/or sequences expressed in different cells, tissues, and/or samples.

It is an object of the present invention to provide a method of amplifying RNA molecules.

It is another object of the present invention to provide primers for first strand cDNA synthesis and probes for circularizing cDNA strands.

It is another object of the present invention to provide kits for amplifying RNA molecules.

It is another object of the present invention to provide a method for detecting,. cataloging and analyzing amplified RNA sequences.

DETAILED DESCRIPTION OF THE INVENTION

Figure 1:
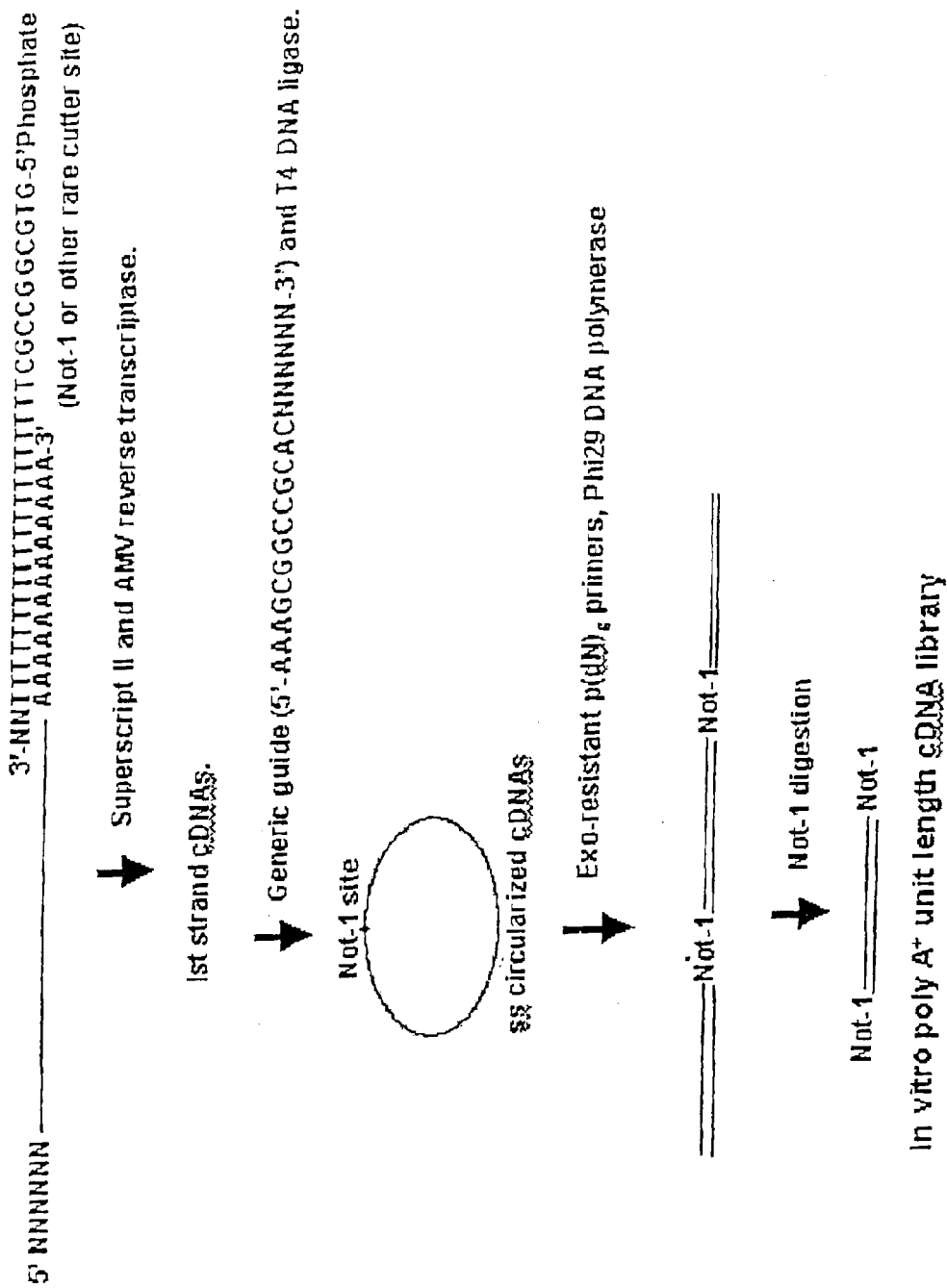
FIG. 1 is a diagram of an example of the disclosed method. A cDNA primer (SEQ ID NO:3) anneals to the poly(A) region of mRNA molecules (SEQ ID NO:4) (top). Reverse transcription produces a linear first strand cDNA molecules. A circularization probe (SEQ ID NO:5) is added and the first strand cDNA molecules are circularized. Exonuclease-resistant random hexamer primers and $\phi$29 DNA polymerase are then used to amplify the circular first strand cDNA molecules via exponential rolling circle amplification. Rolling circle amplification produces double-stranded tandem sequence DNA. The tandem sequence DNA can be cleaved with Not I to produce single tandem repeat units because a Not I site appears between every tandem repeat unit.
Figure 2A:
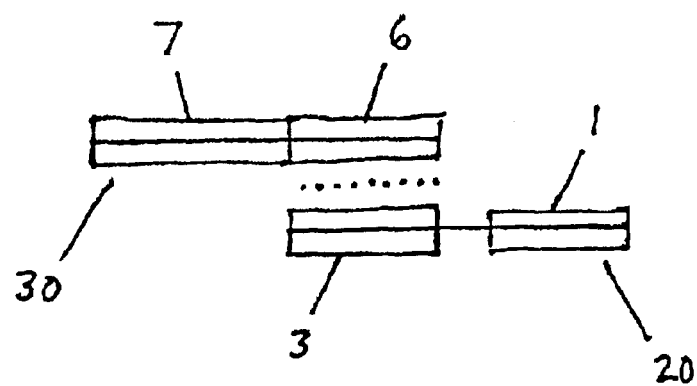
FIGS. 2A, 2B, 2C, 2D, and 2E are diagrams of examples of cDNA primers and circularization probes and their relationships. cDNA primers (20) have RNA complement portions (1) and probe complement portions (3). Optionally, cDNA primers can have primer complement portions (2), primer matching portions (4), cleavage sites (5), and promoter portions (12). Circularization probes (30) have primer complement portions (6) and cDNA complement portions (7). Optionally, circularization probes can have primer matching portions (8), second primer complement portions (9), cleavage sites (10), RNA matching portions (11), and promoter portions (13). Dots between the cDNA primers (20) and circularization probes (30) depict complementarity between the primers and probes
Figure 2B:
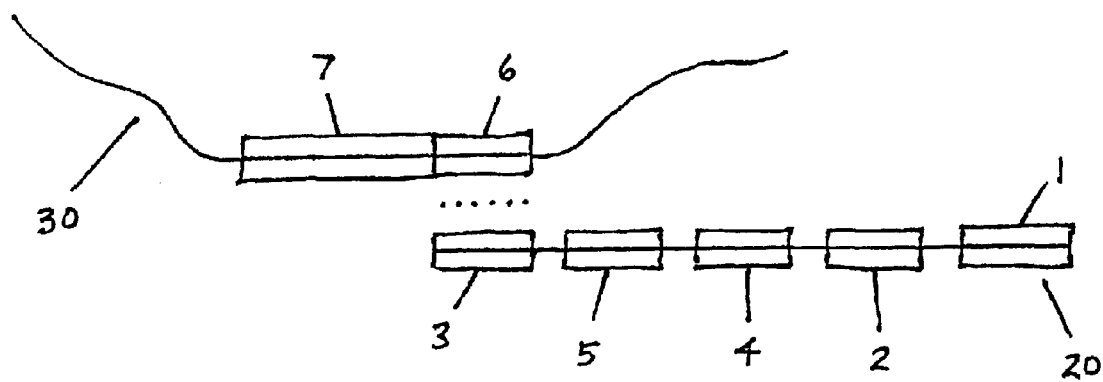
Figure 2C:
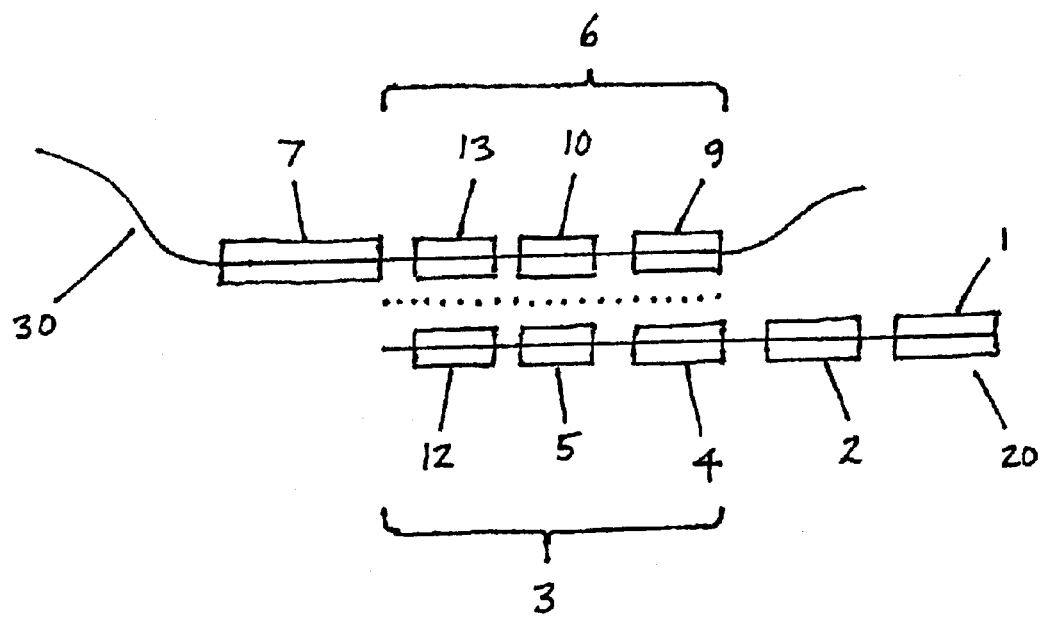
Figure 2D:
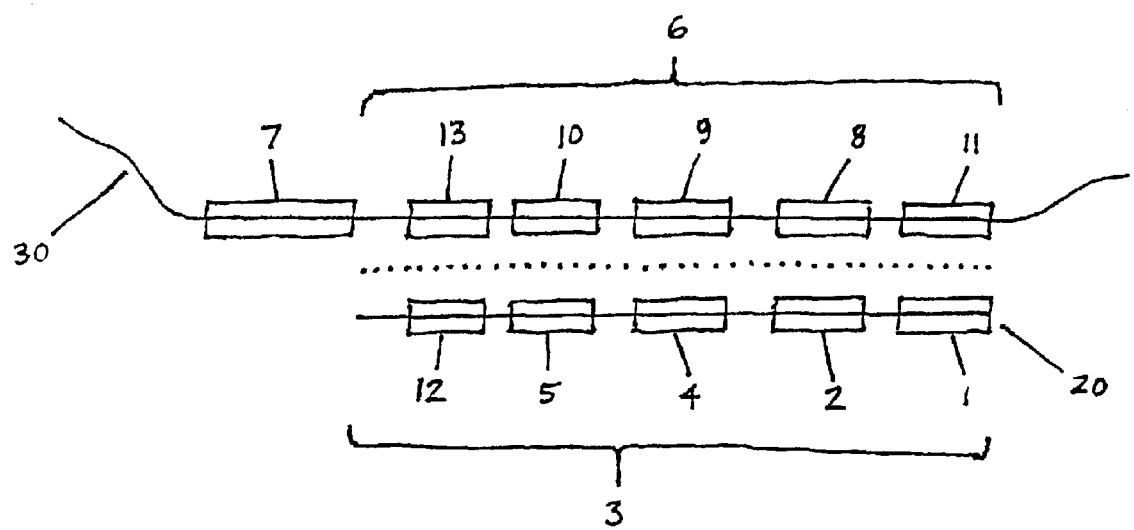
Figure 2E:
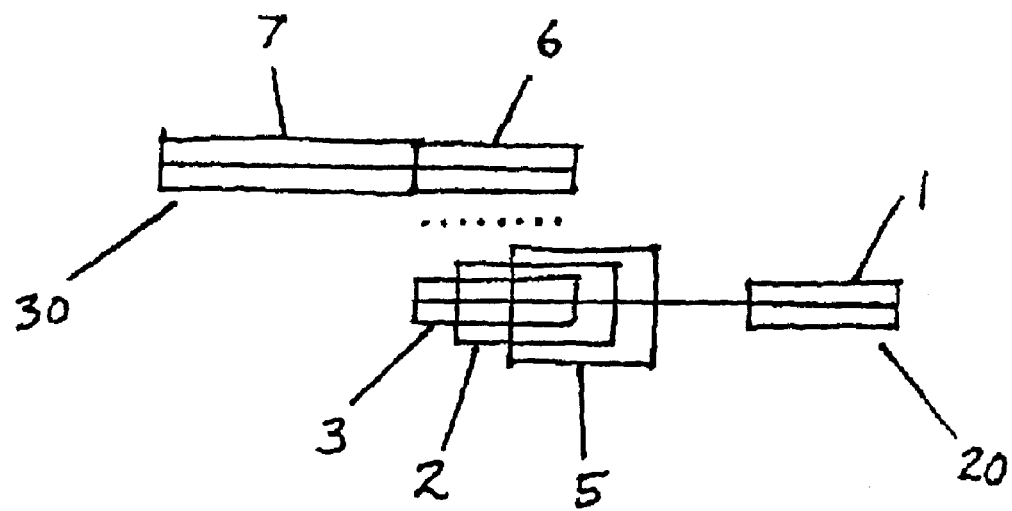

Disclosed are compositions and methods for amplification of RNA molecules. The disclosed method involves synthesizing first strand cDNA molecules from RNA molecules, circularizing the first strand cDNA molecules and replicating the circularized first strand cDNA molecules using rolling circle replication. The method can be aided by the use of specialized primers for cDNA synthesis, referred to as cDNA primers, and specialized probes for circularizing the first strand cDNA molecules, referred to as circularization probes. The method can be used to replicate and amplify multiple RNA molecules, such as all RNA molecules in a sample or all mRNA molecules in a sample, or can be used to replicate and amplify specific RNA molecules. Rolling circle replication of the circularized first strand cDNA molecules results in long DNA strands containing tandem repeats of the cDNA sequence. Rolling circle replication can be primed from a single location on the circular first strand cDNA molecules or can be primed from multiple sites. Regardless of where priming occurs, the resulting tandem sequence DNA will contain tandem repeats of the full cDNA sequence since synthesis continues multiple times around the circle. The disclosed method, an isothermal DNA amplification procedure without repeated denaturation of the template, will also minimize template degradation and allele loss. In some forms, the disclosed method can utilize a DNA polymerase with high fidelity and processivity, such as Φ29 DNA polymerase, to amplify large transcripts with minimal sequence artifacts.

The tandem sequence DNA can be used directly (for detection of sequences, for example), further amplified, cloned, or used any other purpose. Tandem sequence DNA molecules produced in the disclosed method from an RNA sample can contain sequences representing all or a portion of the RNA sequences present in the sample. For example, the disclosed method can be used to produce circular first strand cDNA molecules (and thus, tandem sequence DNA) from all of the RNA molecules in an RNA sample, from all of the mRNA molecules in an RNA sample, or from selected RNA molecules in an RNA sample.

In some forms of the disclosed method, a cDNA primer is used to prime synthesis of a first cDNA strand. The cDNA primer can include an RNA complement portion and a probe complement portion. The RNA complement portion hybridizes to RNA molecules in an RNA sample and primes reverse transcription. The resulting first strand cDNA molecules incorporate the cDNA primer at their 5' ends. The first strand cDNA molecules are circularized using a circularization probe. The circularization probe can include a primer complement portion and a cDNA complement portion. The primer complement portion is complementary to the probe complement portion of the cDNA primer. The cDNA complement portion is hybridizes to sequence in the first strand cDNA molecules. In particular, the cDNA complement portion hybridizes to 3'-end sequence of first strand cDNA molecules. In this way, the ends of first strand cDNA molecules are brought into proximity so they can be ligated together.

The circularized first strand cDNA molecules can then be amplified via rolling circle replication. Rolling circle replication can be primed by a rolling circle replication primer. The rolling circle replication can have a complementary portion, which is complementary to a first strand cDNA molecule. The complementary portion can be complementary to sequence in the cDNA primer, can match sequence in the circularization probe, or both. In this case, the rolling circle replication primer either can be specific for one or some first strand cDNA molecules or can be used to amplify first strand cDNA molecules broadly (depending on whether the primer complement/primer matching sequence in the cDNA primer and/or circularization probe are different (specific) for different first strand cDNA molecules or the same (not specific) for different first strand cDNA molecules. Alternatively, the complementary portion can be complementary to cDNA sequence. In this case, the rolling circle replication primer can be specific for one or a few first strand cDNA molecules. Rolling circle replication primers having random sequence will be complementary to numerous sequences in circular first strand cDNA molecules and can be used to amplify first strand cDNA molecules broadly.

A single cDNA primer and a single circularization probe can be used amplify all RNA molecules in a sample. For example, the cDNA primer can include an RNA complement portion comprised of poly(dT) or random sequence, partially random sequence, and/or nucleotides that can base pair with more than one type of nucleotide. The RNA complement of a cDNA primer will hybridize any RNA sequence to which it is complementary, such as all mRNA (if poly(dT) is used) or all RNA molecules in general (if a generic sequence is used). In this way all of the RNA molecules in a sample can be reverse transcribed. The circularization probe can include, for example, a cDNA complement portion comprised of random sequence, partially random sequence, and/or nucleotides that can base pair with more than one type of nucleotide. The generic nature of the cDNA complement portion allows it to hybridize to any of, or many of, the 3'-end sequences of first strand cDNA molecules. In this way, a circularization probe can be generic for amplification of RNA molecules in an RNA sample.

A single rolling circle replication primer can be used to can be used amplify all RNA molecules in a sample. For example, the rolling circle primer can have a random sequence making it complementary to many sequences in first strand cDNA molecules. Alternatively, the rolling circle replication primer can have a complementary portion that is complementary to sequence in the cDNA primer (that is, the primer complement portion of the cDNA primer), that matches sequence in the circularization probe (that is, the primer matching portion of the circularization probe). As another alternative, the circularization probe can be used as the rolling circle replication primer. In this way, only a single cDNA primer and a single circularization probe would be needed to form circular first strand cDNA molecules and to replicate the circles. The cDNA primer can also serve as a secondary DNA strand displacement primer, thus allowing exponential rolling circle amplification with only these two oligonucleotides.

The tandem sequence DNA also can be made double-stranded. Double-stranded tandem sequence DNA can be used, for example to produce unit lengths of the cDNA sequence making up the tandem sequence DNA. Production of unit length cDNA molecules can be aided by including a cleavage site, such as the recognition site for a restriction enzyme, in the cDNA primer and/or circularization probe. The double-stranded tandem sequence DNA and, especially, the unit lengths of cDNA sequence can be cloned using recombinant DNA techniques and materials. Tandem sequence DNA and tandem sequence DNA fragments, including unit length cDNA molecules, can constitute a cDNA library. Each unit length of cDNA sequence (that is, one of the tandem repeat sequences produced from the circular first strand cDNA molecules) represents the cDNA sequence of an RNA molecule. The unit length of cDNA sequence (or a single tandem repeat sequence) can be referred to as a tandem repeat unit.

The tandem sequence DNA strand produced by rolling circle replication corresponds to the positive strand of the DNA from which the corresponding RNA was replicated. Secondary tandem sequence DNA, which results from replication of tandem sequence DNA, corresponds to the negative strand of the DNA from which the corresponding RNA was replicated. Subsequent generations of tandem sequence DNA strands (for example, tertiary tandem sequence DNA and quaternary tandem sequence DNA) also represent either the positive or negative strand. Either the positive strand (for example, the tandem sequence DNA strand) or the negative strand (for example, the secondary tandem sequence DNA) can be produced in isolation in the disclosed method. This can be accomplished, for example, by synthesizing only the tandem sequence DNA strand or by selectively degrading one of the types of strand.

Tandem sequence DNA can also be transcribed to produce transcripts having sequence complementary to or matching the sequence of RNA molecules. The tandem sequence DNA can be transcribed directly to produce long RNA molecules, referred to as tandem sequence transcripts, made up of tandem repeats of the RNA sequence (or its complement). Unit length cDNA molecules (that is tandem repeat units) can also be transcribed to produce RNA molecules, referred to as tandem repeat transcripts, containing a single RNA sequence (or its complement).

Further amplification of the cDNA sequences can be accomplished using any suitable replication or amplification technique. Useful amplification techniques include rolling circle amplification techniques such as multiply-primed rolling circle amplification and exponential rolling circle amplification. Rolling circle replication and rolling circle amplification of the circularized first strand cDNA molecules can also be combined with multiple strand displacement amplification and other amplification techniques to produce specialized amplification products and/or to further increase the amplification yield.

In another form of the disclosed method, first strand cDNA molecules can be ligated together to form concatemers. These first strand cDNA concatemers can be amplified via multiple strand displacement amplification (and/or any other suitable amplification technique). First strand cDNA concatemers that are circularized can be amplified via rolling circle replication. Rolling circle replication of circular first strand cDNA molecules and/or first strand cDNA concatemers can be carried out simultaneously with multiple strand displacement amplification of uncircularized first strand cDNA molecules and/or uncircularized first strand cDNA concatemers. The circularization operation of the disclosed method, depending on the conditions used, can result in production of one or a combination of the four types of first strand cDNA products: circular first strand cDNA molecules, circular first strand cDNA concatemers, uncircularized first strand cDNA molecules, and uncircularized first strand cDNA concatemers.

The disclosed amplification of RNA molecules is useful for producing nucleic acid molecules corresponding to RNA molecules in an RNA sample. The disclosed method is a general purpose technique for amplifying RNA sequences and the nucleic acid molecules produced can be used for any purpose. Useful purposes include, for example, detecting specific RNA molecules and/or sequences, detecting a population or set of RNA molecules and/or sequences, analyzing or sequencing specific RNA molecules and/or sequences, analyzing or sequencing a population or set of RNA molecules and/or sequences, cataloging a population or set of RNA molecules and/or sequences, cloning specific RNA molecules and/or sequences, cloning a population or set of RNA molecules and/or sequences, and producing a cDNA library. Thus, for example, the disclosed method can be used to identify or analyze the RNA molecules and/or sequences expressed in different cells, tissues, and/or samples, and compare the RNA molecules and/or sequences expressed in different cells, tissues, and/or samples.

The progress of rolling circle amplification reactions (and other amplification reactions) can be monitored in real-time (that is, during the reaction) by using detection primers in the amplification of detection probes during amplification. The detection primer produces a signal during amplification as a quenching moiety in or on the primer becomes separated from a fluorescent label on the primer. When a quenching moiety is in proximity to a fluorescent molecule or label, fluorescence is quenched by transfer of energy to the quenching moiety. Fluorescence is detectable once the quenching moiety is no longer in proximity to the fluorescent label. Detection primers are incorporated into amplification products as they prime replication. In the disclosed amplification reactions, the incorporated primer goes on to serve as a template sequence when the nucleic acid strand in which it is incorporated is replicated. A quenching moiety can be placed in proximity to a fluorescent label on the primer, for example, via hybridization of a nucleic acid sequence to which the quenching moiety is attached to sequence of the primer adjacent to the fluorescent label. When the incorporated primer is replicated, the hybrid is disrupted and the quencher moiety is separated from the fluorescent label, which can then produce a fluorescent signal. Thus, as the amplification reaction proceeds, more and more incorporated detection primers are replicated, producing an ever-increasing fluorescent signal that can be monitored as the reaction proceeds.

Rolling circle amplification involves rolling circle replication of a circular template (here, a circularized first strand cDNA molecule). Rolling circle replication can be mediated by a primer, referred to as a rolling circle replication primer, that hybridizes anywhere on the circular template. Multiple strands can be produced simultaneously by using two or more rolling circle replication primers that hybridize to different sequences (that is, at different locations) in the circular template. Thus, the disclosed method can be performed using of two or more rolling circle replication primers targeted to different sequences in the circular templates. Alternatively, multiple strands can be produced simultaneously by using a rolling circle replication primer having a random sequence. The random sequence hybridizes to different sequences (that is, at different locations) in the circular template.

Use of both rolling circle replication primers (which prime replication of circularized first strand cDNA molecules) and secondary DNA strand displacement primers (which prime replication of the product of replication of circularized first strand cDNA molecules) allows multiple generations of amplification product to be generated simultaneously. This multiplies the yield of amplification. The circularization probe and the cDNA primer can serve as a rolling circle replication primer and secondary DNA strand displacement primer, respectively.

Rolling circle replication of a circular template produces long strands of DNA containing tandem repeats of sequence complementary to the sequence of the circular template. These strands are referred to as tandem sequence DNA. The speed and yield of rolling circle amplification reactions can be greatly increased by replicating the tandem sequence DNA during rolling circle replication. This can be accomplished by using one or more primers complementary to sequence in the tandem sequence DNA. Such primers, referred to as secondary DNA strand displacement primers, have sequence matching sequence in a first strand cDNA molecule (and thus are complementary to the tandem sequence DNA). Replication of the tandem sequence DNA produces more nucleic acid, referred to as secondary tandem sequence DNA, and provides a template for further replication by the rolling circle replication primers (which are complementary to sequences in the secondary tandem sequence DNA). These, and subsequent replication products are similarly replicated producing an overall cascade of replication, referred to as exponential rolling circle amplification, that produces a huge amplification in a short time.

The disclosed method is applicable to numerous areas including, but not limited to, analysis of RNA present in a sample, disease detection, mutation detection, protein expression profiling, RNA expression profiling, gene discovery, gene mapping (molecular haplotyping), agricultural research, and virus detection. Notable uses include detection of nucleic acids in situ in cells, on microarrays, on DNA fibers, and on genomic DNA arrays; detection of RNA in cells; RNA expression profiling; molecular haplotyping; mutation detection; detection of abnormal RNA (for example, overexpression of an oncogene or absence of expression of a tumor suppressor gene); expression in cancer cells; detection of viral genome in cells; viral RNA expression; detection of inherited diseases such as cystic fibrosis, muscular dystrophy, diabetes, hemophilia, sickle cell anemia; assessment of predisposition for cancers such as prostate cancer, breast cancer, lung cancer, colon cancer, ovarian cancer, testicular cancer, pancreatic cancer.

Some forms of the disclosed method can comprise incubating a cDNA primer and an RNA sample comprising RNA molecules under conditions that promote synthesis of first strand cDNA molecules from the RNA molecules, incubating a circularization probe and the first strand cDNA molecules under conditions that promote circularization of the first strand cDNA molecules, and incubating the circularized first strand cDNA molecules under conditions that promote rolling circle replication of the circularized first strand cDNA molecules, thereby amplifying RNA sequences.

The rolling circle replication can result in formation of tandem sequence DNA, wherein the tandem sequence DNA is replicated to form secondary tandem sequence DNA, wherein the tandem sequence DNA and the secondary tandem sequence DNA form double-stranded tandem sequence DNA. The cDNA primer can comprise an RNA complement portion, wherein the RNA complement portion hybridizes to one or more of the RNA molecules, wherein the cDNA primer is incorporated into the first strand cDNA molecules during synthesis of the first strand cDNA molecules.

The cDNA primer can be incorporated into the first strand cDNA molecules during synthesis of the first strand cDNA molecules, wherein the circularization probe comprises a cDNA complement portion, and a primer complement portion, wherein the cDNA complement portion hybridizes to one or more of the first strand cDNA molecules, wherein the primer complement portion hybridizes to the cDNA primer incorporated into the first strand cDNA molecules, wherein hybridization of the cDNA complement portion to the first strand cDNA molecules and hybridization of the primer complement portion to the cDNA primer brings the ends of the first strand cDNA molecules into proximity thereby mediating circularization of the first strand cDNA molecules.

Rolling circle replication can be primed by a rolling circle replication primer, wherein the rolling circle replication primer has a random sequence, wherein the rolling circle replication is primed from a plurality of locations on the circularized first strand cDNA molecules. Rolling circle replication can be primed by a plurality of rolling circle replication primers, wherein the rolling circle replication is primed from a plurality of locations on the circularized first strand cDNA molecules. Rolling circle replication can be primed by one or more rolling circle replication primers, wherein the rolling circle replication results in formation of tandem sequence DNA, wherein the tandem sequence DNA is not replicated, wherein the tandem sequence DNA comprises sequence matching sequence in the RNA molecules.

Rolling circle replication can be primed by the circularization probe, wherein the rolling circle replication results in formation of tandem sequence DNA, wherein the tandem sequence DNA is not replicated, wherein the tandem sequence DNA comprises sequence matching sequence in the RNA molecules.

Rolling circle replication can be primed by one or more rolling circle replication primers, wherein the rolling circle replication results in formation of tandem sequence DNA, wherein the tandem sequence DNA is replicated to form secondary tandem sequence DNA, wherein replication of the tandem sequence DNA can be primed by one or more secondary DNA strand displacement primers. The rolling circle replication primers can have 5' phosphates and the secondary DNA strand displacement primers can have 5' hydroxyls, with the result that the tandem sequence DNA has 5' phosphates and the secondary tandem sequence DNA has 5' hydroxyls. The method then can further comprise incubating the tandem sequence DNA and secondary tandem sequence DNA in the presence of a phosphate-dependent exonuclease, whereby the tandem sequence DNA is degraded and the secondary tandem sequence DNA remains.

The rolling circle replication primers can have 5' hydroxyls and the secondary DNA strand displacement primers can have 5' phosphates, with the result that the tandem sequence DNA has 5' hydroxyls and the secondary tandem sequence DNA has 5' phosphates. The method then can further comprise incubating the tandem sequence DNA and secondary tandem sequence DNA in the presence of a phosphate-dependent exonuclease, whereby the secondary tandem sequence DNA is degraded and the tandem sequence DNA remains.

Rolling circle replication can be primed by the circularization probe, wherein the rolling circle replication results in formation of tandem sequence DNA, wherein the tandem sequence DNA is replicated to form secondary tandem sequence DNA, wherein replication of the tandem sequence DNA can be primed by one or more secondary DNA strand displacement primers. The circularization probe can have a 5' phosphate and the secondary DNA strand displacement primers can have 5' hydroxyls, with the result that the tandem sequence DNA has 5' phosphates and the secondary tandem sequence DNA has 5' hydroxyls. The method then can further comprise incubating the tandem sequence DNA and secondary tandem sequence DNA in the presence of a phosphate-dependent exonuclease, whereby the tandem sequence DNA is degraded and the secondary tandem sequence DNA remains.

The circularization probe can have a 5' hydroxyl and the secondary DNA strand displacement primers can have 5' phosphates, with the result that the tandem sequence DNA has 5' hydroxyls and the secondary tandem sequence DNA has 5' phosphates. The method then can further comprises incubating the tandem sequence DNA and secondary tandem sequence DNA in the presence of a phosphate-dependent exonuclease, whereby the secondary tandem sequence DNA is degraded and the tandem sequence DNA remains.

Rolling circle replication can be primed by a rolling circle replication primer, wherein the rolling circle replication primer further comprises a promoter portion, wherein the rolling circle replication results in formation of tandem sequence DNA. The cDNA primer can further comprise a promoter portion, wherein the rolling circle replication results in formation of tandem sequence DNA. Rolling circle replication can result in formation of tandem sequence DNA and the method can further comprise detecting one or more target sequences in the tandem sequence DNA.

Rolling circle replication can result in formation of tandem sequence DNA, wherein a plurality of first strand cDNA molecules are synthesized from a plurality of RNA molecules, wherein a plurality of tandem sequence DNAs are formed, wherein the plurality of tandem sequence DNAs correspond to the plurality of RNA molecules, wherein the plurality of tandem sequence DNAs constitute a catalog of sequences derived from the RNA sample.

Rolling circle replication can result in formation of tandem sequence DNA and the method can further comprise sequencing one or more target sequences in the tandem sequence DNA. Rolling circle replication can result in formation of tandem sequence DNA and the method can further comprise, following the rolling circle replication, incubating the tandem sequence DNA under conditions that promote replication of the tandem sequence DNA, wherein during replication of the tandem sequence DNA at least one of the replicated strands is displaced from the tandem sequence DNA by strand displacement replication of another replicated strand.

Rolling circle replication can result in formation of tandem sequence DNA, wherein the tandem sequence DNA is replicated to form secondary tandem sequence DNA during the rolling circle replication and the method can further comprise, following the rolling circle replication, incubating the tandem sequence DNA and the secondary tandem sequence DNA under conditions that promote replication of the tandem sequence DNA and the secondary tandem sequence DNA, wherein during replication of the tandem sequence DNA and the secondary tandem sequence DNA at least one of the replicated strands is displaced from the tandem sequence DNA or the secondary tandem sequence DNA by strand displacement replication of another replicated strand.

The conditions that promote synthesis of first strand cDNA molecules can comprise incubating the cDNA primer and the RNA sample in the presence of a reverse transcriptase, wherein the conditions that promote circularization of the first strand cDNA molecules can comprise incubating the circularization probe and the first strand cDNA molecules in the presence of ligase, wherein the conditions that promote rolling circle replication of the circularized first cDNA molecules can comprise incubating the circularized first strand cDNA molecules in the presence of a DNA polymerase.

Some forms of the method can comprise (1) incubating a cDNA primer and an RNA sample comprising RNA molecules under conditions that promote synthesis of first strand cDNA molecules from the RNA molecules, wherein the conditions that promote synthesis of first strand cDNA molecules can comprise incubating the cDNA primer and the RNA sample in the presence of a reverse transcriptase; (2) incubating the first strand cDNA molecules in the presence of an RNAse H activity; (3) incubating the first strand cDNA molecules under alkaline conditions; (4) neutralizing the first strand cDNA molecules; (4) purifying the first strand cDNA molecules; (5) incubating a circularization probe and the first strand cDNA molecules under conditions that promote circularization of the first strand cDNA molecules, wherein the conditions that promote circularization of the first strand cDNA molecules can comprise incubating the circularization probe and the first strand cDNA molecules in the presence of ligase; and (6) incubating the circularized first strand cDNA molecules under conditions that promote rolling circle replication of the circularized first strand cDNA molecules, thereby amplifying RNA sequences, wherein the conditions that promote rolling circle replication of the circularized first cDNA molecules can comprise incubating the circularized first strand cDNA molecules in the presence of a DNA polymerase.

Some forms of the method can comprise (1) incubating a cDNA primer and an RNA sample comprising RNA molecules under conditions that promote synthesis of first strand cDNA molecules from the RNA molecules, (2) incubating a circularization probe and the first strand cDNA molecules under conditions that promote ligation of the first strand cDNA molecules to each other to form first strand cDNA concatemers, and (3) incubating the first strand cDNA concatemers under conditions that promote strand displacement replication of the first strand cDNA concatemers, thereby amplifying RNA sequences. In some forms of the disclosed method, the first strand cDNA molecules can be ligated to at least one other first strand cDNA molecule to form one or more first strand cDNA concatemers.

Multiply-primed RCA can be performed using a single rolling circle replication primer (which hybridizes to multiple sites on a circular first strand cDNA molecule) or multiple rolling circle replication primers (each of which can hybridize to a single site on a first strand cDNA molecule or multiple sites on a first strand cDNA molecule). Multiple priming (as occurs in MPRCA) can increase the yield of amplified product from RCA. Primers anneal to multiple locations on a circular first strand cDNA molecule and a product of extension by polymerase is initiated from each location. In this way, multiple extensions are achieved simultaneously from a single first strand cDNA molecule.

In some forms of the disclosed method, multiple priming can be achieved in several different ways. For example, two or more specific rolling circle replication primers that anneal to different sequences on the circular first strand cDNA molecule can be used, one or more specific rolling circle replication primers that each anneals to a sequence repeated at two or more separate locations on the circular first strand cDNA molecule can be used, a combination of rolling circle replication primers that each anneal to a different sequence on the circular first strand cDNA molecule or to a sequence repeated at two or more separate locations on the circular first strand cDNA molecule can be used, one or more random or degenerate primers, which can anneal to many locations on the circular first strand cDNA molecule, can be used, or a combination of such primers can be used.

Any or all of the probes, primers and other oligonucleotides used in the disclosed method can be resistant to degradation by exonuclease activity that may be present in the reaction. This has the advantage of permitting the probes and primers to persist in reactions that contain an exonuclease activity and that may be carried out for long incubation periods. The persistence of primers allows new priming events to occur for the entire incubation time of the reaction, which is one of the hallmarks of exponential RCA (ERCA) and has the advantage of increasing the yield of amplified DNA. Such nuclease resistant probes and primers also allow selective degradation of excess uncircularized first strand cDNA molecules that might otherwise interfere with hybridization of detection probes and address probes to the amplified nucleic acid.

Fluorescent change probes and primers, which are useful for obtaining real-time detection of amplification, refer to all probes and primers that involve a change in fluorescence intensity or wavelength based on a change in the form or conformation of the probe or primer and nucleic acid to be detected, assayed or replicated. Examples of fluorescent change probes and primers include molecular beacons, Amplifluors, FRET probes, cleavable FRET probes, TaqMan probes, scorpion primers, fluorescent triplex oligos including but not limited to triplex molecular beacons or triplex FRET probes, fluorescent water-soluble conjugated polymers, PNA probes and QPNA probes. Change in fluorescence wavelength or intensity from fluorescent change probes and primers generally involves energy transfer and/or quenching. Fluorescent change probes and primers can be classified according to their structure and/or function. Fluorescent change probes include, for example, hairpin quenched probes, cleavage quenched probes, cleavage activated probes, and fluorescent activated probes.

Random and/or degenerate probes and primers can be used with the disclosed method. As used herein, degenerate refers to an oligonucleotide in which one or more of the base positions is occupied by more than one base, that is, a mixture of oligonucleotides of defined length in which one or more positions of an individual member of the mixture is occupied by a base selected at random from among more than one of the possibilities for that position. Such collections of oligonucleotides can be readily synthesized using standard oligonucleotide synthesis instruments and software. As used herein, random refers to an oligonucleotide in which each of the base positions is occupied by a base selected at random from among a complete set of possibilities, but commonly limited to, for example, the four bases adenine (A), guanine (G), cytosine (C) and thymine (T) (or uracil (U)). For example, random oligonucleotides can be composed of the four nucleotides deoxyriboadenosine monophosphate (dAMP), deoxyribocytidine monophosphate (dCMP), deoxyriboguanosine monophosphate (dGMP), or deoxyribothymidine monophosphate (dTMP). Degenerate oligonucleotides where not every base position is selected at random from among a complete set of possibilities can be referred to as partially random oligonucleotides. In some embodiments, the primers can contain nucleotides, including any types of modified nucleotides or nucleotide analogs, which can serve to make the primers resistant to enzyme degradation, to have other effects, or to give the primers useful properties.

It is to be understood that the disclosed method and compositions are not limited to specific synthetic methods, specific analytical techniques, or to particular reagents unless otherwise specified, and, as such, can vary. It is also to be understood that the terminology used herein is for the purpose of describing particular embodiments only and is not intended to be limiting.

Materials

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a rolling circle replication primer is disclosed and discussed and a number of modifications that can be made to a number of molecules including the rolling circle replication primer are discussed, each and every combination and permutation of the rolling circle replication primer and the modifications that are possible are specifically contemplated unless specifically indicated to the contrary. Thus, if a class of molecules A, B, and C are disclosed as well as a class of molecules D, E, and F and an example of a combination molecule, A–D is disclosed, then even if each combination is not individually recited, each is individually and collectively contemplated. Thus, is this example, each of the combinations A–E, A–F, B–D, B–E, B–F, C–D, C–E, and C–F are specifically contemplated and should be considered disclosed from disclosure of A, B, and C; D, E, and F; and the example combination A–D. Likewise, any subset or combination of these is also specifically contemplated and disclosed. Thus, for example, the sub-group of A–E, B–F, and C–E is specifically contemplated and should be considered disclosed from disclosure of A, B, and C; D, E, and F; and the example combination A–D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. cDNA Primers

Primers used for synthesis of first strand cDNA molecules are referred to herein as cDNA primers. cDNA primers are oligonucleotides having sequence complementary to sequence in RNA molecules. This portion of the cDNA primer is referred to as the RNA complement portion of the cDNA primer. cDNA primers also include probe complement portions. Generally, cDNA primers must have RNA complement portions and probe complement portions. cDNA primers can also include primer complement portions, primer matching portions, cleavage sites, and promoter portions. These portions can be separate and non-overlapping in the cDNA primer, or they can overlap partially or completely with each other.

cDNA primers can be used in sets. This is useful, for example, when cDNA primers are specific for particular RNA molecules or groups of RNA molecules. In such a case, the different cDNA primers in the set can be specific for different RNA molecules and/or groups of RNA molecules. Sets of cDNA primers can be used for any purpose, such as to increase coverage of RNA molecules to be amplified. This can include targeting, and thus amplifying, more RNA molecules and targeting different parts or multiple parts of RNA molecules. This can be useful, for example, for amplifying long RNA molecules. When used in sets, cDNA primers in the set can have the same RNA complement sequence, different RNA complement sequences, and/or one of a set of RNA complement sequences. Thus, for example, a set of 12 cDNA primers can have 6 cDNA primers with the same RNA complement sequence, 2 cDNA primers with the same second, different RNA complement sequence, and 4 cDNA primers each with an RNA complement sequence different from any of the RNA complement sequences of any other cDNA primer in the set. As another example, a set of 12 cDNA primers can have a different RNA complement sequence for each of the cDNA primers.

When used in sets, cDNA primers in the set can have the same probe complement sequence, different probe complement sequences, and/or one of a set of probe complement sequences. Thus, for example, a set of 12 cDNA primers can have 6 cDNA primers with the same probe complement sequence, 2 cDNA primers with the same second, different probe complement sequence, and 4 cDNA primers each with a probe complement sequence different from any of the probe complement sequences of any other cDNA primer in the set. As another example, a set of 12 cDNA primers can have a different probe complement sequence for each of the cDNA primers. Because the probe complement portion of a cDNA primer is complementary to the primer complement portion of a circularization probe, sets of cDNA primers having cDNA primers with different probe complement sequences can be specific for different circularization probes. In this way, different first strand cDNA molecules can be circularized (or not) based on which circularization probes are used with the set of cDNA primers.

1. RNA Complement Portions

RNA complement portions of cDNA primers are complementary to sequence in RNA molecules. This allows the cDNA primers to prime reverse transcription of RNA molecules. The portion of an RNA molecule that is complementary to the RNA complement portion of the cDNA primer is referred to as the primer complement portion. cDNA primers can be specific for specific RNA molecules (that is, the cDNA primers prime reverse transcription primarily only the specific RNA molecules). This can be accomplished, for example, by designing an RNA complement portion that is complementary to a specific sequence in the RNA molecule of interest. Alternatively, cDNA primers can be designed to prime reverse transcription of RNA molecules broadly. This can be accomplished, for example, by including an RNA complement portion comprised of poly(dT) or random sequence, partially random sequence, and/or nucleotides that can base pair with more than one type of nucleotide. The RNA complement of the cDNA primer will hybridize any RNA sequence to which it is complementary, such as all mRNA (if poly(dT) is used) or all RNA molecules in general (if a generic sequence is used). In this way all of the RNA molecules in a sample can be reverse transcribed. A useful form of RNA complement portion for amplification of mRNA is poly(dT) followed by one, two, or a few, random or partially random nucleotides. This allows the cDNA primer to hybridize at or near the junction of transcribed sequence and poly(A) sequence in RNA molecules. When targeting a specific sequence in an RNA molecule, the targeted sequence can be anywhere in the RNA molecule, although targeting sequences at or near the 3' end of the RNA molecule will result in more complete cDNA of the RNA molecule. The RNA complement portion can also be designed based on relevant principals for the design of first strand cDNA primers (many of which are known) to the extent they are consistent with other features and function of the cDNA primers and the disclosed method.

In some forms of cDNA primer, the RNA complement portion of a cDNA primer can have a random sequence or can be made up of nucleotides that can base pair with more than one type of nucleotide (such as universal nucleotides or inosine). In this case, the cDNA primer can hybridize to, and prime reverse transcription of, any RNA molecule or sequence. Such a cDNA primer can be referred to as a generic cDNA primer. Sequences that are random sequences, that are made up of nucleotides that can base pair with more than one type of nucleotide, or a combination, can be referred to as generic sequences. Partially random or degenerate sequences can also be used in RNA complement portions of cDNA primers. This results in cDNA primers that generally can prime transcription of multiple RNA molecules and sequences but that will not prime transcription of all RNA molecules.

In some forms of cDNA primer, the RNA complement portion of a cDNA primer can include poly(dT). In this case, the cDNA primer can hybridize to, and prime reverse transcription of, polyadenylated RNA molecules, such as mRNA. Such cDNA primers can be referred to as poly(A) cDNA primers. Production of first strand cDNA molecules from only polyadenylated RNA molecules in an RNA sample is useful because such RNA molecules are relevant to gene expression and expression profiling. Specific sequences can be used at the 3' end of cDNA primers that include poly(dT) in the RNA complement portion (that is, poly(A) cDNA primers). Doing so results in a cDNA primer that is specific for a certain polyadenylated RNA molecule and will prime transcription from the end of the RNA molecule (making it possible to obtain full length cDNA sequence of the RNA molecule). The combination of a specific sequence and a poly(dT) sequence assures that transcription will be primed at the junction of specific RNA sequence and the poly(A) tail. Further, the specific sequence will specify priming of only those RNA molecules having that sequence at the poly(A) junction.

A similar effect can be achieved for transcription of polyadenylated RNA molecules in general by using random sequence (or nucleotides that can base pair with more than one type of nucleotide) at the 3' end of cDNA primers that include poly(dT) in the RNA complement portion. The cDNA primer will prime transcription from the end of any RNA molecule (making it possible to obtain full length cDNA sequence of the RNA molecule). The combination of a generic sequence and a poly(dT) sequence assures that transcription will be primed at the junction of specific RNA sequence and the poly(A) tail. Because the generic sequence allows the primer to hybridize to any poly(A) junction sequence, the cDNA primer can be used to produce first strand cDNA molecules of polyadenylated RNA in general from the poly(A) junction (and thus potentially full length). Such cDNA primers can be referred to as junction-specific poly(A) cDNA primers.

If the RNA complement portion of a cDNA primer has a specific sequence, then the cDNA primer can hybridize to, and prime reverse transcription of, specific RNA molecules and sequences. Such a cDNA primer can be referred to as a specific cDNA primer. Specific cDNA primers are useful for producing first strand cDNA molecules from specific RNA molecules. It also can be useful to use sets of specific cDNA primers together in order to produce first strand cDNA molecules from a particular set of RNA molecules of interest.

Junction-specific poly(A) cDNA primers have RNA complement portions that comprise poly(dT) sequence and a generic sequence, at the 3' end, that is complementary to any sequence or a variety of sequences. In some forms, the generic sequence can be a random or other sequence capable of hybridizing to any sequence. Useful forms of junction-specific poly(A) cDNA primers can have a partially random sequence that excludes thymidine nucleotides immediately adjacent to the poly(dT) sequence. This allows the cDNA primer to remain junction-specific. For example, the fully random generic sequence NN includes the sequences TT (as well as TA, TC, and TG). As a result, RNA complement portions having the sequence TTTTTTTTTTTTTTTTTTTTNN (nucleotides 11–32 of SEQ ID NO:3) would include RNA complement portions TTTTTTTTTTTTTTTTTTTTTT (SEQ ID NO:6). cDNA primers within the mix containing this RNA complement would thus be poly(A) cDNA primers and would not be junction-specific. For this reason, particularly useful forms of generic sequences for junction-specific poly(A) cDNA primers exclude thymidine nucleotides immediately adjacent to the poly(dT) sequence. Such partially random generic sequences in RNA complement portions can be, for example, V, VN, VNN, VNNN, VNNNN, VNNNNN, VNNNNNN, and so on; VV, VVN, VVNN, VVNNN, VVNNNN, VVNNNNN, and so on; VVV, VVVN, VVVNN, VVVNNN, VVVNNNN, and so on; VVVV, VVVVN, VVVVNN, VVVVNNN, and so on; and VVVVV, VVVVVN, VVVVVNN, and so on. V refers to A, C or G nucleotides (that is, not T). Other generic sequences following these principles are possible. In many cases, however, the effect of including some non-junction-specific cDNA primer in the mix will not be detrimental to the production of first strand cDNA molecules. Thus, fully random generic sequences can be used in RNA complement portion of junction-specific poly(A) cDNA primers.

The RNA complement portion of a cDNA primer can be any length that supports specific and stable hybridization between the primer and an RNA molecule under the conditions used. Generally this is 6 to 35 nucleotides long, but is usefully 10 to 20 nucleotides long.

2. Probe Complement Portions

Probe complement portions of cDNA primers are complementary to sequence in circularization probes. When the cDNA primer is incorporated into first strand cDNA molecules, the probe complement portion is incorporated into the first strand cDNA molecule. The probe complement portion allows the circularization probe to hybridize to the first strand cDNA molecule and mediate its circularization. For this purpose, the probe complement portion should be at the 5' end of the cDNA primer. The portion of the circularization probe that is complementary to the probe complement portion of a cDNA primer is referred to as the primer complement portion of the circularization probe. Because the probe complement portion need only hybridize to the primer complement portion of a circularization probe, there are no specific sequence requirements. Thus, a probe complement portion and its cognate primer complement portion can have any desired sequence so long as they are complementary to each other. The sequence of the probe complement portion can be referred to as the probe complement sequence. More specifically, the sequence of the probe complement portion of a cDNA primer can be referred to as the probe complement sequence of the cDNA primer.

The probe complement portion of a cDNA primer can be any length that supports specific and stable hybridization between the primer and the primer complement portion of its cognate circularization probe under the conditions used. Generally this is 6 to 35 nucleotides long, but is usefully 10 to 20 nucleotides long.

3. Primer Complement Portions

Primer complement portions of cDNA primers are complementary to sequence in rolling circle replication primers (or other primers used for positive strand synthesis). When the cDNA primer is incorporated into first strand cDNA molecules, the primer complement portion is incorporated into the first strand cDNA molecule. The primer complement portion allows the rolling circle replication primer to hybridize to the first strand cDNA molecule and prime rolling circle replication of it. Placing the complement to the rolling circle replication primer in the cDNA primer allows a single rolling circle replication primer to mediate rolling circle replication of all circular first strand cDNA molecules incorporating that cDNA primer (which can be all of the circular first stand cDNA molecules if a single cDNA primer is used). Such replication is then independent of sequence in the cDNA sequence of the first strand cDNA molecule (and thus independent of sequence in the source RNA molecules). Although the primer complement portion can be anywhere in the cDNA primer and can overlap any other component or sequence of the cDNA primer, it is useful if the primer complement portion does not overlap any primer matching portion. This can reduce the chance of interactions between rolling circle replication primers and secondary DNA strand displacement primers. The portion of the rolling circle replication primer (or other primer) that is complementary to the primer complement portion of a cDNA primer is referred to as the complementary portion of the rolling circle replication primer (or other primer). Because the primer complement portion need only hybridize to the complementary portion of a rolling circle replication primer, there are no specific sequence requirements. Thus, a primer complement portion of a cDNA primer and its cognate complementary portion (in the rolling circle replication primer) can have any desired sequence so long as they are complementary to each other. The sequence of the primer complement portion can be referred to as the primer complement sequence. More specifically, the sequence of the primer complement portion of a cDNA primer can be referred to as the primer complement sequence of the cDNA primer.

The primer complement portion of a cDNA primer can be any length that supports specific and stable hybridization between the primer and the complementary portion of its cognate rolling circle replication primer under the conditions used. Generally this is 6 to 35 nucleotides long, but is usefully 10 to 20 nucleotides long.

4. Primer Matching Portions

Primer matching portions of cDNA primers match sequence in secondary DNA strand displacement primers (or other primers used for negative strand synthesis). When the cDNA primer is incorporated into first strand cDNA molecules, the primer matching portion is incorporated into the first strand cDNA molecule. When the first strand cDNA molecule is replicated, a complement of the primer matching portion is incorporated into tandem sequence DNA (or other amplification product). This primer complement sequence allows the secondary DNA strand displacement primer to hybridize to the tandem sequence DNA and prime replication of it. A complement to the secondary DNA strand displacement primer will appear in each repeat in the tandem repeat DNA. Although the primer matching portion can be anywhere in the cDNA primer and can overlap any other component or sequence of the cDNA primer, it is useful if the primer matching portion does not overlap any primer complement portion. This can reduce the chance of interactions between rolling circle replication primers and secondary DNA strand displacement primers.

The portion of the secondary DNA strand displacement primer (or other primer) that matches the primer matching portion of a cDNA primer is referred to as the matching portion of the secondary DNA strand displacement primer (or other primer). Because the complement of the primer matching portion need only be complementary to the primer complement portion of a secondary DNA strand primer, there are no specific sequence requirements. Thus, a primer matching portion of a cDNA primer and its cognate matching portion (in the secondary DNA strand displacement primer) can have any desired sequence so long as they are match each other. The sequence of the primer matching portion can be referred to as the primer matching sequence. More specifically, the sequence of the primer matching portion of a cDNA primer can be referred to as the primer matching sequence of the cDNA primer.

The primer matching portion of a cDNA primer can be any length that supports specific and stable hybridization between the complement of the primer matching portion and the primer complement portion of its cognate secondary DNA strand displacement primer under the conditions used. Generally this is 6 to 35 nucleotides long, but is usefully 10 to 20 nucleotides long.

5. Cleavage Sites

Cleavage sites can be included in cDNA primers. Incorporation of a cDNA primer in first strand cDNA molecules incorporates cleavage sites on the cDNA primer in the first strand cDNA molecules. The cleavage sites then would appear in tandem sequence DNA (and other amplification products) produced from the first strand cDNA molecules. Cleavage sites are thus useful for cleaving tandem sequence DNA and can be used to cleave tandem sequence DNA into unit lengths.

Cleavage sites are sequences that can be cleaved. Cleavage sites can be, for example, sequences at which restriction endonucleases can cleave a nucleic acid molecule. Cleavages sites can be sequence-specific, meaning that only certain nucleotide sequences are recognized and cleaved. The sequence that specifies cleavage is referred to as a recognition site. The actual point at which a nucleic acid molecule is cut may or may not overlap with the recognition sequence. As used herein, the term cleavage site encompasses both the place where cleavage actually occurs and the recognition site. Different restriction endonucleases generally have different recognition sequences.

cDNA primers and other compositions and components used in the disclosed method may include a number of cleavage sites, many of which may have no functional significance in the disclosed method. That is, any nucleic acid sequence may include cleavage sites by virtue of their sequence, but such cleavage site may not be used in the disclosed method. In general, reference to a cleavage site or cleavage sites herein are intended to refer to particular cleavage sites that have significance for the disclosed method. Thus, a cDNA primer said to have a "single cleavage site" has the referenced cleavage site but may also have other, unreferenced cleavage sites that are not functionally significant (that is, cleavage sites not used in the method). The distinction between cleavage sites that may be present in a cDNA primer or other composition or component used in the disclosed method and a cleavage site having functional significance can be emphasized by referring to the cleavage site having functional significance as a cleavage site of interest. Thus, a cDNA primer said to have a "single cleavage site of interest" has the referenced cleavage site but may also have other, unreferenced cleavage sites that are not functionally significant.

It is useful to cleave amplification products of first strand cDNA molecules into full length tandem repeat units. For this purpose, it is useful to use cleavage sites having recognition sequences that occur only rarely (on average) in nucleic acid sequences. This makes it less likely that the recognition sequence will appear in the cDNA sequence of first strand cDNA molecules thus making it less likely that the cDNA sequence, rather than the cDNA primer sequence, will be cleaved. Generally, recognition sequences that are longer will occur less frequently. For example, an eight nucleotide recognition sequence will occur only once every 65,536 nucleotides, on average. A seven nucleotide recognition sequence will occur only once every 16,384 nucleotides, on average. These intervals are much longer than typical (or even long) transcript length. Restriction endonucleases having eight nucleotide recognition sequences include Not I, Asc I, AsiS I, Fse I, Pac I, Pme I, Sbf I, Sfi I, and Swa I.

6. Promoter Portions

Promoter portions correspond to the sequence of an RNA polymerase promoter. A promoter portion can be included in a cDNA primer so that transcripts can be generated from the resulting first strand cDNA molecule or TS-DNA (or other amplification products). The sequence of any promoter can be used, but simple promoters for RNA polymerases without complex requirements are preferred. It is also preferred that the promoter is not recognized by any RNA polymerase that may be present in the sample containing the target nucleic acid sequence. Useful promoters include, for example, phage promoters, bacterial promoters, promoters for phage RNA polymerases, and promoters for bacterial RNA polymerases. For example, the promoter portion can correspond to the sequence of a T3 RNA polymerase promoter, a T7 RNA polymerase promoter, or an SP6 RNA polymerase promoter. The T3, T7 and SP6 RNA polymerases are highly specific for particular promoter sequences. Other promoter sequences specific for RNA polymerases with this characteristic would also be useful. Because promoter sequences are generally recognized by specific RNA polymerases, the cognate polymerase for the promoter portion of the cDNA primer should be used for transcriptional amplification. Numerous promoter sequences are known and any promoter specific for a suitable RNA polymerase can be used. The promoter portion can be located anywhere in the cDNA primer and can be in either orientation.

cDNA primers can also have detection tag portions and/or address tag portions. Detection tag portions have sequences matching the sequence of the complementary portion of detection probes and can be used to associate detection probes with tandem sequence DNA. Detection tag portions, when amplified during rolling circle replication, result in TS-DNA having detection tag sequences that are complementary to the complementary portion of detection probes. However, use of detection probes specific for cDNA sequence can be more useful for detecting specific RNA sequences. Address tag portions have sequences matching the sequence of the complementary portion of an address probe and can be used to associate tandem sequence DNA with solid-state substrates having address probes. Address tag portions, when amplified during rolling circle replication, result in TS-DNA having address tag sequences that are complementary to the complementary portion of address probes.

Although in design, complementary sequences generally will be fully complementary (that is, all of the nucleotides will be able to base pair), full complementarity is not required to achieve the required function. For example, the probe complement portion need only functionally hybridize to a circularization probe in order for it to allow the circularization probe to mediate circularization. Such functional hybridization does not require complete and exact complementarity or base pairing. Thus, unless the context clearly indicates to the contrary, sequences referred to herein as being complementary need only be functionally complementary (that is, support base pairing sufficient to allow the oligonucleotides and/or nucleic acid molecules involved to function in the disclosed method in the manner required).

Similarly, although matching sequences generally will fully match (that is, all of the nucleotides will be the same or equivalent), full matching is not required to achieve the required function. For example, the complement of a primer matching portion need only functionally hybridize to the relevant primer in order for it to allow the primer to primer replication. Such functional hybridization does not require complete and exact complementarity or base pairing. Thus, unless the context clearly indicates to the contrary, a sequence referred to herein as matching another sequence need only have a complement that is functionally complementary to the other sequence.

cDNA primers may also include modified nucleotides to make them resistant to exonuclease digestion. For example, the primer can have three or four phosphorothioate linkages between nucleotides at the 5' end of the primer. Those segments of the cDNA primer that do not correspond to a specific portion of the cDNA primer can be arbitrarily chosen sequences. It is useful if cDNA primers do not have any sequences that are self-complementary, although this is not required. It is considered that this condition is met if there are no complementary regions greater than six nucleotides long without a mismatch or gap. For producing tandem repeat transcripts (transcripts of only one tandem repeat unit), it can be useful, although not required, to include a transcription terminator sequence on the first strand cDNA molecules. If included, the transcription terminator sequence should be 5' of any promoter portion of the cDNA primer. For producing of tandem sequence transcripts (transcripts of multiple tandem repeat units), it is useful if cDNA primers containing a promoter portion do not have any sequences that resemble a transcription terminator, such as a run of eight or more thymidine nucleotides.

A cDNA primer is specific for, or corresponds to, a circularization probe when the probe complement portion of the cDNA primer is complementary to the primer complement portion of the circularization probe. A cDNA primer is not specific for, or does not correspond to, a circularization probe when the probe complement portion of the cDNA primer is not substantially complementary to the circularization probe. A probe complement portion is not substantially complementary to another sequence if it has a melting temperature 10° C. lower than the melting temperature under the same conditions of a sequence fully complementary to the probe complement portion of the cDNA primer.

A cDNA primer is specific for, or corresponds to, a set of circularization probes when the probe complement portion of the cDNA primer is complementary to the primer complement portion of the circularization probes in the set. A cDNA primer is not specific for, or does not correspond to, a set of circularization probes when the probe complement portion of the cDNA primer is not substantially complementary to the circularization probes in the set.

Examples of cDNA primers are shown in FIGS. 2A, 2B, 2C, 2D, and 2E. cDNA primers (20) have RNA complement portions (1) and probe complement portions (3). Optionally, cDNA primers can have primer complement portions (2), primer matching portions (4), cleavage sites (5), and promoter portions (12). The RNA complement portion (1) of cDNA primers is complementary to sequence in RNA molecules. The probe complement portion (3) of cDNA primers is complementary to sequence in circularization probes. Specifically, the probe complement portion (3) of a cDNA primer is complementary to the primer complement portion (6) of a circularization probe. This complementarity is depicted in FIG. 2 by dots between the cDNA primers (20) and the circularization probes (30). The probe complement portion (3) of cDNA primers generally must extend to the 5' end of the cDNA primer. The RNA complement portion (1) of cDNA primers generally must be at the 3' end of the cDNA primer.

B. Circularization Probes

Circularization probes are specialized probes for circularizing the first strand cDNA molecules. Circularization probes are oligonucleotides having sequence complementary to sequence in cDNA primers. This portion of the circularization probe is referred to as the primer complement portion of the circularization probe. Circularization probes also have cDNA complement portions, which are complementary to sequence in the cDNA sequence of first strand cDNA molecules. Generally, circularization probes must have a primer complement portion and a cDNA complement portion. Circularization probes can also include primer matching portions, second primer complement portions, cleavage sites, and promoter portions. These portions can be separate and non-overlapping in the cDNA primer, or they can overlap partially or completely with each other. An exception to this is the primer complement-portion and the cDNA complement portion, which generally should not overlap.

The primer complementary portion of a circularization probe allows the circularization probe to hybridize to cDNA primers incorporated into first strand cDNA molecules. The portion of a cDNA primer that is complementary to the primer complement portion of the circularization probe is referred to as the probe complement portion. Circularization probes can be designed to circularize first strand cDNA molecules broadly. This can be accomplished, for example, by including a cDNA complement portion comprised of random sequence, partially random sequence, and/or nucleotides that can base pair with more than one type of nucleotide The cDNA complement of the circularization probe will hybridize any cDNA sequence to which it is complementary, such as the 3' end sequence of first strand cDNA molecules. In this way all of the first strand cDNA molecules can be circularized.

Circularization probes can be used in sets. This is useful, for example, when circularization probes are specific for particular cDNA primers or groups of cDNA primers. In such a case, the different circularization probes in the set can be specific for different cDNA primers and/or groups of cDNA primers. Sets of circularization probes can be used for any purpose, such as to target different first strand cDNA molecules for circularization. For example, only those first strand cDNA molecules having a probe complement portion complementary to the primer complement portions of the circularization probes will be circularized. Similarly, only those first strand cDNA molecules having 3' end sequence complementary to the cDNA complement portions of the circularization probes will be circularized. This can be used, for example, to target particular full length cDNA molecules by using circularization probes having cDNA complement sequences that match known 5' end sequences of RNA molecules of interest. Use of cDNA complement sequences matching internal RNA sequences can be used in a similar way to target specific partial cDNA molecules.

When used in sets, circularization probes in the set can have the same cDNA complement sequence, different cDNA complement sequences, and/or one of a set of cDNA complement sequences. Thus, for example, a set of 12 circularization probes can have 6 circularization probes with the same cDNA complement sequence, 2 circularization probes with the same second, different cDNA complement sequence, and 4 circularization probes each with a cDNA complement sequence different from any of the cDNA complement sequences of any other circularization probe in the set. As another example, a set of 12 circularization probes can have a different cDNA complement sequence for each of the circularization probes.

When used in sets, circularization probes in the set can have the same primer complement sequence, different primer complement sequences, and/or one of a set of primer complement sequences. Thus, for example, a set of 12 circularization probes can have 6 circularization probes with the same primer complement sequence, 2 circularization probes with the same second, different primer complement sequence, and 4 circularization probes each with a primer complement sequence different from any of the primer complement sequences of any other circularization probe in the set. As another example, a set of 12 circularization probes can have a different primer complement sequence for each of the circularization probes. Because the primer complement portion of a circularization probe is complementary to the probe complement portion of a cDNA primer, sets of circularization probes having circularization probes with different primer complement sequences can be specific for different cDNA primers. In this way, different first strand cDNA molecules can be circularized (or not) based on which cDNA primers are used with the set of circularization probes.

1. Primer Complement Portions

Primer complement portions of circularization probes are complementary to sequence in cDNA primers. When the cDNA primer is incorporated into first strand cDNA molecules, the probe complement portion of the cDNA primer is incorporated into the first strand cDNA molecule. The primer complement portion allows the circularization probe to hybridize to the first strand cDNA molecule and mediate its circularization. For this purpose, the primer complement portion should be adjacent to the cDNA complementary portion of the circularization probe. The portion of the cDNA primer that is complementary to the primer complement portion of a circularization probe is referred to as the probe complement portion of the cDNA primer. Because the primer complement portion need only hybridize to the probe complement portion of a cDNA primer, there are no specific sequence requirements. Thus, a primer complement portion and its cognate probe complement portion can have any desired sequence so long as they are complementary to each other. The sequence of the primer complement portion can be referred to as the primer complement sequence. More specifically, the sequence of the primer complement portion of a circularization probe can be referred to as the primer complement sequence of the circularization probe.

The primer complement portion of a circularization probe can be any length that supports specific and stable hybridization between the probe and the probe complement portion of its cognate cDNA primer under the conditions used. Generally this is 6 to 35 nucleotides long, but is usefully 10 to 20 nucleotides long.

2. cDNA Complement Portions cDNA complement portions of circularization probes are complementary to sequence in first strand cDNA molecules. The cDNA complement portion allows the circularization probe to hybridize to the first strand cDNA molecule and mediate its circularization. For this purpose, the cDNA complement portion should be adjacent to the primer complement portion of the circularization probe. For circularization to occur, the circularization probe brings the ends of the first strand cDNA molecule into proximity. For this reason, the cDNA sequence of the first strand cDNA molecule hybridizing to the cDNA complement portion of the circularization probe should be the 3' end sequence. In order to circularize first strand cDNA molecules in general (that is, to be able to circularize any first strand cDNA molecule regardless of source or sequence), the cDNA complement portion can have a random sequence, a partially random sequence, and/or nucleotides that can base pair with more than one type of nucleotide. The generic nature of such a cDNA complement portion allows it to hybridize to any of, or many of, the 3'-end sequences of first strand cDNA molecules. In this way, a circularization probe can be generic for amplification of RNA molecules in an RNA sample. The sequence of the cDNA complement portion can be referred to as the cDNA complement sequence. More specifically, the sequence of the cDNA complement portion of a circularization probe can be referred to as the cDNA complement sequence of the circularization probe.

The cDNA complement portion of the circularization probes determines which first strand cDNA molecules will be circularized. In some forms of circularization probe, the cDNA complement portion can have a random sequence or be made up of nucleotides that can base pair with more than one type of nucleotide (such as universal nucleotides or inosine). In this case, the circularization probe can hybridize to, and mediate circularization of, any first strand cDNA molecule. Such a circularization probe can be referred to as a generic circularization probe. Partially random or degenerate sequences can also be used in cDNA complement portions of circularization probes. This results in circularization probes that generally can mediate circularization of multiple first strand cDNA molecules and sequences but that will not mediate circularization of all first strand cDNA molecules. This effect can be used to limit the first strand cDNA molecules for which a circularization probe can mediate circularization.

In some forms of circularization probe, the cDNA complement portion can have a specific sequence. In this case, the circularization probe can hybridize to, and mediate circularization of, specific first strand cDNA molecules. Such a circularization probe can be referred to as a specific circularization probe. Specific circularization probes are useful for circularizing specific first strand cDNA molecules or specific forms of first strand cDNA molecules. This can be useful, for example, to favor circularization of full length first strand cDNA molecules of particular RNA molecules or circularization of first strand cDNA molecules having a particular 3' end sequence. It also can be useful to use sets of specific circularization probes together in order to produce circular first strand cDNA molecules from a particular set of linear first strand cDNA molecules of interest.

The cDNA complement portion of a circularization probe can be any length that supports specific and stable hybridization between the probe and a cDNA sequence under the conditions used. Generally this is 6 to 35 nucleotides long, but is usefully 10 to 20 nucleotides long.

3. Second Primer Complement Portions

Second primer complement portions of circularization probes are complementary to sequence in secondary DNA strand displacement primers (or other primers used for negative strand synthesis). The second primer complement portion of a circularization probe generally will be part of (that is, overlap) the primer complement portion of the circularization probe. In this way, the second primer complement portion will be complementary to the primer matching portion of the cDNA primer. When the cDNA primer is incorporated into first strand cDNA molecules, the primer matching, portion is incorporated into the first strand cDNA molecule. When the first strand cDNA molecule is replicated, a complement to the primer matching portion of the cDNA primer is present in the replicated strand. This complement is itself complementary to a secondary DNA strand displacement primer. This primer complement sequence allows the secondary DNA strand displacement primer to hybridize to the tandem sequence DNA and prime replication of it. A complement to the secondary DNA strand displacement primer will appear in each repeat in the tandem repeat DNA. Although the second primer complement portion can be anywhere in the circularization probe and can overlap any other component or sequence of the circularization probe, it is useful if the primer complement portion does not overlap any primer matching portion. The portion of the secondary DNA strand displacement primer (or other primer) that is complementary to the second primer complement portion of a circularization probe is referred to as the primer complement portion of the secondary DNA strand displacement primer (or other primer). Because the primer complement portion need only hybridize to the primer complement portion of a secondary DNA strand displacement primer, there are no specific sequence requirements. Thus, a second primer complement portion of a circularization probe and its cognate primer complement portion (in the secondary DNA strand displacement primer) can have any desired sequence so long as they are complementary to each other. The sequence of the second primer complement portion can be referred to as the second primer complement sequence. More specifically, the sequence of the second primer complement portion of a circularization probe can be referred to as the second primer complement sequence of the circularization probe.

The second primer complement portion of a circularization probe can be any length that supports specific and stable hybridization between the probe and the primer complement portion of its cognate secondary DNA strand displacement primer under the conditions used. Generally this is 6 to 35 nucleotides long, but is usefully 10 to 20 nucleotides long.

4. Primer Matching Portions

Primer matching portions of circularization probes match sequence in rolling circle replication primers (or other primers used for positive strand synthesis). The primer matching portion of a circularization probe generally will be part of (that is, overlap) the primer complement portion of the circularization probe. In this way, the primer matching portion will be complementary to the primer complement portion of the cDNA primer. When the cDNA primer is incorporated into first strand cDNA molecules, the primer complement portion is incorporated into the first strand cDNA molecule. This primer complement sequence allows the rolling circle replication primer to hybridize to the first strand cDNA molecule and prime replication of it. The primer matching portion can be anywhere in the circularization probe and can overlap any other component or sequence of the circularization probe. The portion of the rolling circle replication primer (or other primer) that is complementary to the primer matching portion of a circularization probe is referred to as the complementary portion of the rolling circle replication primer (or other primer). Because the complement of the primer matching portion need only be complementary to the complementary portion of a rolling circle replication primer, there are no specific sequence requirements. Thus, a primer matching portion of a circularization probe and its cognate matching portion (in the rolling circle replication primer) can have any desired sequence so long as they are match each other. The sequence of the primer matching portion can be referred to as the primer matching sequence. More specifically, the sequence of the primer matching portion of a circularization probe can be referred to as the primer matching sequence of the circularization probe.

The primer matching portion of a circularization probe can be any length that supports specific and stable hybridization between the complement of the primer matching portion and the primer complement portion of its cognate rolling circle replication primer under the conditions used. Generally this is 6 to 35 nucleotides long, but is usefully 10 to 20 nucleotides long.

5. Cleavage Sites

Cleavage sites can be included in circularization probes. Cleavage sites in a circularization probe generally will be part of (that is, overlap) the primer complement portion of the circularization probe. Incorporation of a cDNA primer in first strand cDNA molecules incorporates cleavage sites on the cDNA primer (and corresponding cleavage sites on the circularization probe) in the first strand cDNA molecules. The cleavage sites then would appear in tandem sequence DNA (and other amplification products) produced from the first strand cDNA molecules. Cleavage sites are thus useful for cleaving tandem sequence DNA and can be used to cleave tandem sequence DNA into unit lengths.

6. Promoter Portions

Promoter portions correspond to the sequence of an RNA polymerase promoter. The promoter portion of a circularization probe generally will be part of (that is, overlap) the primer complement portion of the circularization probe. Incorporation of a cDNA primer in first strand cDNA molecules incorporates the promoter portion on the cDNA primer (and corresponding promoter portion on the circularization probe) in the first strand cDNA molecules. The promoter then would appear in tandem sequence DNA (and other amplification products) produced from the first strand cDNA molecules.

A promoter portion can be included in a circularization probe so that transcripts can be generated from the resulting first strand cDNA molecule or TS-DNA (or other amplification products). The sequence of any promoter can be used, but simple promoters for RNA polymerases without complex requirements are preferred. It is also preferred that the promoter is not recognized by any RNA polymerase that may be present in the sample containing the target nucleic acid sequence. Useful promoters include, for example, phage promoters, bacterial promoters, promoters for phage RNA polymerases, and promoters for bacterial RNA polymerases. For example, the promoter portion can correspond to the sequence of a T3 RNA polymerase promoter, a T7 RNA polymerase promoter, or an SP6 RNA polymerase promoter. The T3, T7 and SP6 RNA polymerases are highly specific for particular promoter sequences. Other promoter sequences specific for RNA polymerases with this characteristic would also be useful. Because promoter sequences are generally recognized by specific RNA polymerases, the cognate polymerase for the promoter portion of the circularization probe should be used for transcriptional amplification. Numerous promoter sequences are known and any promoter specific for a suitable RNA polymerase can be used. The promoter portion can be located anywhere in the circularization probe and can be in either orientation.

Circularization probes can also have detection tag portions and/or address tag portions. Detection tag portions and address tag portions of a circularization probe generally will be part of (that is, overlap) the primer complement portion of the circularization probe. Incorporation of a cDNA primer in first strand cDNA molecules incorporates complements of detection tag portions and address tag portions on the cDNA primer (and corresponding detection tag portions and address tag portions on the circularization probe) in the first strand cDNA molecules. The detection tag portions and address tag portions then would appear in secondary tandem sequence DNA (and other amplification products) produced from the first strand cDNA molecules. Detection tag portions have sequences matching the sequence of the complementary portion of detection probes and can be used to associate detection probes with tandem sequence DNA. Detection tag portions, when amplified during rolling circle replication, result in TS-DNA having detection tag sequences that are complementary to the complementary portion of detection probes. However, use of detection probes specific for cDNA sequence can be more useful for detecting specific RNA sequences. Address tag portions have sequences matching the sequence of the complementary portion of an address probe and can be used to associate tandem sequence DNA with solid-state substrates having address probes. Address tag portions, when amplified during rolling circle replication, result in TS-DNA having address tag sequences that are complementary to the complementary portion of address probes.

Circularization probes may also include modified nucleotides to make them resistant to exonuclease digestion. For example, the circularization probe can have three or four phosphorothioate linkages between nucleotides at the 5' end of the probe. Those segments of the circularization probe that do not correspond to a specific portion of the circularization probe can be arbitrarily chosen sequences. It is useful if circularization probes do not have any sequences that are self-complementary, although this is not required. It is considered that this condition is met if there are no complementary regions greater than six nucleotides long without a mismatch or gap. For producing tandem repeat transcripts (transcripts of only one tandem repeat unit), it can be useful, although not required, to include a transcription terminator sequence on the first strand cDNA molecules. If included, the transcription terminator sequence should be 5' of any promoter portion of the circularization probe. For producing tandem sequence transcripts (transcripts of multiple tandem repeat units), it is useful if circularization probes containing a promoter portion do not have any sequences that resemble a transcription terminator, such as a run of eight or more thymidine nucleotides.

A circularization probe is specific for, or corresponds to, a cDNA primer when the primer complement portion of the circularization probe is complementary to the probe complement portion of the cDNA primer. A circularization probe is not specific for, or does not correspond to, a cDNA primer when the primer complement portion of the circularization probe is not substantially complementary to the cDNA primer. A primer complement portion is not substantially complementary to another sequence if it has a melting temperature 10° C. lower than the melting temperature under the same conditions of a sequence fully complementary to the primer complement portion of the circularization probe.

A circularization probe is specific for, or corresponds to, a set of cDNA primers when the primer complement portion of the circularization probe is complementary to the probe complement portion of the cDNA primers in the set. A circularization probe is not specific for, or does not correspond to, a set of cDNA primers when the primer complement portion of the circularization probe is not substantially complementary to the cDNA primers in the set.

Examples of circularization probes are shown in FIGS. 2A, 2B, 2C, 2D, and 2E. Circularization probes (30) have primer complement portions (6) and cDNA complement portions (7). Optionally, circularization probes can have primer matching portions (8), second primer complement portions (9), cleavage sites (10), RNA matching portions (11), and promoter portions (13). The cDNA complement portion (7) of circularization probes is complementary to sequence in first strand cDNA molecules. The primer complement portion (6) of circularization probes is complementary to sequence in cDNA primers. Specifically, the primer complement portion (6) of a circularization probe is complementary to the probe complement portion (3) of a cDNA primer. This complementarity is depicted in FIG. 2 by dots between the cDNA primers (20) and the circularization probes (30). In circularization probes, the primer complement portion (6) and the cDNA complement portion (7) generally must be adjacent, but neither need be at the end of the circularization probe. Circularization probes can have non-complementary sequences at their 5' end, their 3' end, or both. The primer complement portion (6) of circularization probes generally must be 5' of the cDNA complement portion (7) of the circularization probe.

C. First Strand cDNA Molecules

First strand cDNA molecules are cDNA strands produced from reverse transcription of RNA molecules primed by cDNA primers. A first strand cDNA molecule includes sequence reverse transcribed from a single RNA molecule and cDNA primer sequence. The sequence in first strand cDNA molecules that is reverse transcribed from RNA is referred to as the cDNA sequence of the first strand cDNA molecule. Sequence of the incorporated cDNA primer is referred to as the primer sequence of the first strand cDNA molecule. First strand cDNA molecules, as synthesized, are linear single-stranded DNA molecules. These linear molecules can be circularized, concatemerized, or both. Circularized first strand cDNA molecules are referred to as circular first strand cDNA molecules, circularized first strand cDNA molecules, or first strand cDNA circles. First strand cDNA circles are made of a single first strand cDNA molecules. Concatemerized first strand cDNA molecules are referred to as first strand cDNA concatemers. Circularized first strand cDNA concatemers are referred to as circular first strand cDNA concatemers, circularized first strand cDNA concatemers, or first strand cDNA concatemer circles. First strand cDNA concatemers are made of a plurality of first strand cDNA molecules. Linear and circular first strand cDNA molecules can be referred to collectively as first strand cDNA molecules. Similarly, linear and circular first strand cDNA concatemers can be referred to collectively as first strand cDNA concatemers.

Because first strand cDNA molecules incorporate cDNA primers, first strand cDNA molecules include all of the portions, components and feature of the incorporated cDNA primer. As described elsewhere herein, cDNA primers can include RNA complement portions, probe complement portions, primer complement portions, primer matching portions, cleavage sites, promoter portions, detection tag portions, and address tag portions. Thus, first strand cDNA molecules can include RNA complement portions, probe complement portions, primer complement portions, primer matching portions, cleavage sites, promoter portions, detection tag portions, and address tag portions.

First strand cDNA molecules produced in the disclosed method are designed to be amplified by rolling circle amplification (RCA) and/or multiple strand displacement amplification (also referred to as multiple displacement amplification; MDA). Rolling circle amplification generally requires that the first strand cDNA molecule (or first strand cDNA concatemer) be circularized. Multiple strand displacement amplification of the disclosed first strand cDNA molecules generally involves concatemerization of the first strand cDNA molecules, although this is not required. Because the disclosed method can be used to efficiently and broadly amplify RNA sequences, the forms of first strand cDNA molecules are usefully adapted to achieving this result.

Some feature of first strand cDNA molecules will be the result of features of the cDNA primers used to synthesize them and/or the circularization probes used to circularize them. Amplification of a broad range of RNA molecules or amplification of specific RNA molecules generally will be a function of the cDNA primers and circularization probes (generally based on principals described elsewhere herein). Amplification of the first strand cDNA molecules is then just a matter of using appropriate primers and conditions for amplification. First strand cDNA molecules generally have at least one primer complement portion. The primer complement portion is complementary to sequence in a rolling circle replication primer (or other primer used for amplification). The primer complement portion can be any sequence in the first strand cDNA molecule but preferably corresponds to the primer complement portion of the cDNA primer incorporated into the cDNA primer. For multiply-primed RCA, a plurality of primer complement portions are required. Where random or degenerate rolling circle replication primers are used, the sequence of the primer complement portions need not either be known or be of a specified sequence.

First strand cDNA molecules can include primer matching portions. Primer matching portions are complementary to sequence in secondary DNA strand displacement primers (or other primers used for amplification). When the primer matching portion matches sequence in a secondary DNA strand displacement primer, the primer match portion can also be referred to as a secondary DNA strand displacement primer matching portion. The primer matching portion can be any sequence in the first strand cDNA molecule but preferably corresponds to the primer matching portion of the cDNA primer incorporated into the cDNA primer. Where random or degenerate rolling circle replication primers are used, the rolling circle replication primers will serve as secondary DNA strand displacement primers. In this case, the sequence of the primer matching portions need not either be known or be of a specified sequence.

First strand cDNA molecule can include detection tag portions. The detection tag portion can be any sequence in the first strand cDNA. For some forms of the method, it is useful to use a sequence in the cDNA sequence part of the first strand cDNA molecule as a detection tag portion because detection will then be dependent on the identity (and sequence) of the RNA molecule from which the first strand cDNA molecule was derived. For broad detection of multiple or all first strand cDNA molecules, use of a detection tag portion in the primer sequence (which is derived from the cDNA primer) of the first strand cDNA molecule is useful. When fluorescent change probes (or other detection probes) are used for detection, the first strand cDNA molecule can include at least one detection tag portion.

A circular first strand cDNA molecule, when replicated, gives rise to a long DNA molecule containing multiple repeats of sequences complementary to the first strand cDNA molecule. This long DNA molecule is referred to herein as tandem sequences DNA (TS-DNA). TS-DNA contains sequences complementary to the primer complement portions, to RNA complement portions and to probe complement portions. These sequences in the TS-DNA are referred to as primer sequences (which match sequence in the rolling circle replication primers), RNA sequences (which match sequence in the original RNA molecule), and probe sequences (which match the sequence of the circularization probe. If present on the first strand cDNA molecule, the TS-DNA also contains sequences complementary to cleavage sites, promoter portions, detection tag portions, and address tag portions. These sequences in the TS-DNA are referred to as cleavage sites, promoter sequences, detection tags, and address tags, respectively. The TS-DNA will also have sequence complementary to the matching portion of secondary DNA strand displacement primers. This sequence in the TS-DNA is referred to as the secondary DNA strand displacement primer complement or as the primer complement.

If random or degenerate rolling circle replication primers are used, they can act as secondary DNA strand displacement primer. In this case, the first strand cDNA molecules will have multiple secondary DNA strand displacement primer matching portions that generally will not be, and need not be, specifically identified. If random or degenerate rolling circle replication primers are used, the primers and the secondary DNA strand displacement primer matching portions are preferably 4 to 10 nucleotides long, and most preferably 6, 7 or 8 nucleotides long.

D. Rolling Circle Replication Primers

A rolling circle replication primer (RCRP) is an oligonucleotide having sequence complementary to one or more primer complement portions of a first strand cDNA molecule. This sequence is referred to as the complementary portion of the RCRP. The complementary portion of a RCRP and the cognate primer complement portion can have any desired sequence so long as they are complementary to each other. In general, the sequence of the RCRP can be chosen such that it is not significantly complementary to any other portion of the first strand cDNA molecule. That is, the RCRP would be complementary only to primer complement portions. If random or degenerate rolling circle replication primers are used, the primers collectively will be complementary to many sequences on a first strand cDNA molecule. The complementary portion of a rolling circle replication primer can be any length that supports specific and stable hybridization between the primer and the primer complement portion. Generally this is 10 to 35 nucleotides long, but is preferably 16 to 20 nucleotides long. Random or degenerate rolling circle replication primers are preferably 4 to 10 nucleotides long, and most preferably 6, 7 or 8 nucleotides long. Useful rolling circle replication primers are fluorescent change primers.

It is useful if rolling circle replication primers also contain additional sequence at the 5' end of the RCRP that is not complementary to any part of the first strand cDNA molecule. This sequence is referred to as the non-complementary portion of the RCRP. The non-complementary portion of the RCRP, if present, can serve to facilitate strand displacement during DNA replication. The non-complementary portion of a RCRP can be any length, but is generally 1 to 100 nucleotides long, and preferably 4 to 8 nucleotides long. The non-complementary portion can be involved in interactions that provide specialized effects. For example, the non-complementary portion can comprise a quencher complement portion that can hybridize to a peptide nucleic acid quencher or peptide nucleic acid fluor or that can form an intramolecular structure. Random or degenerate rolling circle replication primers preferably do not include a non-complementary portion. Rolling circle replication primers can also comprise fluorescent moieties or labels and quenching moieties. Rolling circle replication primers can be capable of forming an intramolecular stem structure involving one or both of the RCRP's ends. Such rolling circle replication primers are referred to herein as hairpin rolling circle replication primers. Primers forming intramolecular stem structures, and their use in rolling circle amplification, are described in U.S. patent application Ser. No. 09/803,713.

Rolling circle replication primers can also include modified nucleotides to make them resistant to exonuclease digestion. For example, the primer can have three or four phosphorothioate linkages between nucleotides at the 5' end of the primer. Such nuclease resistant primers allow selective degradation of excess uncircularized first strand cDNA molecules that might otherwise interfere with hybridization of detection probes and address probes to the amplified nucleic acid. A rolling circle replication primer can be used as the tertiary DNA strand displacement primer in strand displacement cascade amplification. Random or degenerate rolling circle replication primers can serve as secondary and tertiary DNA strand displacement primers.

A rolling circle replication primer is specific for, or corresponds to, a first strand cDNA molecule when the complementary portion of the rolling circle replication primer is complementary to the primer complement portion of the first strand cDNA molecule. A rolling circle replication primer is not specific for, or does not correspond to, a first strand cDNA molecule when the complementary portion of the rolling circle replication primer is not substantially complementary to the first strand cDNA molecule. A complementary portion is not substantially complementary to another sequence if it has a melting temperature 10° C. lower than the melting temperature under the same conditions of a sequence fully complementary to the complementary portion of the rolling circle replication primer.

A rolling circle replication primer is specific for, or corresponds to, a set of first strand cDNA molecules when the complementary portion of the rolling circle replication primer is complementary to the primer complement portion of the first strand cDNA molecules in the set. A rolling circle replication primer is not specific for, or does not correspond to, a set of first strand cDNA molecules when the complementary portion of the rolling circle replication primer is not substantially complementary to the first strand cDNA molecules in the set.

E. DNA Strand Displacement Primers

Primers used for secondary DNA strand displacement are referred to herein as DNA strand displacement primers. One form of DNA strand displacement primer, referred to herein as a secondary DNA strand displacement primer, is an oligonucleotide having sequence matching part of the sequence of a first strand cDNA molecule. This sequence in the secondary DNA strand displacement primer is referred to as the matching portion of the secondary DNA strand displacement primer. The sequence in the first strand cDNA molecule that matches the matching portion of the secondary DNA strand displacement primer is referred to as the secondary DNA strand displacement primer matching portion (or as the primer matching portion). The matching portion of a secondary DNA strand displacement primer is complementary to sequences in TS-DNA. The matching portion of a secondary DNA strand displacement primer may be complementary to any sequence in TS-DNA. However, it is preferred that it not be complementary TS-DNA sequence matching either the rolling circle replication primers or a tertiary DNA strand displacement primer, if one is being used. This prevents hybridization of the primers to each other. The matching portion of a secondary DNA strand displacement primer can be any length that supports specific and stable hybridization between the primer and its complement. Generally this is 6 to 35 nucleotides long, but is usefully 12 to 25 nucleotides long.

Secondary DNA strand displacement primers can be specific for, or correspond to, all of the first strand cDNA molecules in an amplification reaction or in a set of first strand cDNA molecules in an amplification reaction. A secondary DNA strand displacement primer is specific for, or corresponds to, an first strand cDNA molecule when the matching portion of the secondary DNA strand displacement primer matches the primer matching portion of the first strand cDNA molecule. A secondary DNA strand displacement primer is not specific for, or does not correspond to, a first strand cDNA molecule when the matching portion of the secondary DNA strand displacement primer does not substantially match sequence in the first strand cDNA molecule. A matching portion does not substantially match another sequence if it has a melting temperature with the complement of the other sequence that is 10° C. lower than the melting temperature under the same conditions of a sequence fully complementary to the matching portion of the secondary DNA strand displacement primer.

A secondary DNA strand displacement primer is specific for, or corresponds to, a set of first strand cDNA molecules when the matching portion of the secondary DNA strand displacement primer matches the primer matching portion of the first strand cDNA molecules in the set. A secondary DNA strand displacement primer is not specific for, or does not correspond to, a set of first strand cDNA molecules when the matching portion of the secondary DNA strand displacement primer does not substantially match the first strand cDNA molecules in the set. Secondary DNA strand displacement primers can be fluorescent change primers although this is not preferred.

It is useful if secondary DNA strand displacement primers also contain additional sequence at the 5' end of the primer that does not match any part of the first strand cDNA molecule. This sequence is referred to as the non-matching portion of the secondary DNA strand displacement primer. The non-matching portion of the secondary DNA strand displacement primer, if present, can serve to facilitate strand displacement during DNA replication. The non-matching portion of a secondary DNA strand displacement primer may be any length, but is generally 1 to 100 nucleotides long, and preferably 4 to 8 nucleotides long. The non-matching portion can be involved in interactions that provide specialized effects. For example, the non-matching portion can comprise a quencher complement portion that can hybridize to a peptide nucleic acid quencher or peptide nucleic acid fluor or that can form an intramolecular structure. Secondary DNA strand displacement primers can also comprise fluorescent moieties or labels and quenching moieties.

Useful secondary DNA strand displacement primers for use in the disclosed method can form an intramolecular stem structure involving one or both of the secondary DNA strand displacement primer's ends. Such secondary DNA strand displacement primers are referred to herein as hairpin secondary DNA strand displacement primers. Primers forming intramolecular stem structures, and their use in rolling circle amplification, are described in U.S. patent application Ser. No. 09/803,713.

Another form of DNA strand displacement primer, referred to herein as a tertiary DNA strand displacement primer, is an oligonucleotide having sequence complementary to part of the sequence of a first strand cDNA molecule. This sequence is referred to as the complementary portion of the tertiary DNA strand displacement primer. This complementary portion of the tertiary DNA strand displacement primer matches sequences in TS-DNA. The complementary portion of a tertiary DNA strand displacement primer may be complementary to any sequence in the first strand cDNA molecule. However, it is preferred that it not be complementary first strand cDNA molecule sequence matching the secondary DNA strand displacement primer. This prevents hybridization of the primers to each other. The complementary portion of a tertiary DNA strand displacement primer can be any length that supports specific and stable hybridization between the primer and its complement. Generally this is 6 to 35 nucleotides long, but is preferably 12 to 25 nucleotides long. Tertiary DNA strand displacement primers can be fluorescent change primers although this is not preferred.

Useful tertiary DNA strand displacement primers for use in the disclosed method can form an intramolecular stem structure involving one or both of the tertiary DNA strand displacement primer's ends. Such tertiary DNA strand displacement primers are referred to herein as hairpin tertiary DNA strand displacement primers.

It is useful if tertiary DNA strand displacement primers also contain additional sequence at their 5' end that is not complementary to any part of the first strand cDNA molecule. This sequence is referred to as the non-complementary portion of the tertiary DNA strand displacement primer. The non-complementary portion of the tertiary DNA strand displacement primer, if present, serves to facilitate strand displacement during DNA replication. The non-complementary portion of a tertiary DNA strand displacement primer may be any length, but is generally 1 to 100 nucleotides long, and preferably 4 to 8 nucleotides long. A rolling circle replication, primer is a preferred form of tertiary DNA strand displacement primer. Tertiary DNA strand displacement primers can also comprise fluorescent moieties or labels and quenching moieties.

DNA strand displacement primers may also include modified nucleotides to make them resistant to exonuclease digestion. For example, the primer can have three or four phosphorothioate linkages between nucleotides at the 5' end of the primer. Such nuclease resistant primers allow selective degradation of excess uncircularized first strand cDNA molecules that might otherwise interfere with hybridization of detection probes and address probes to the amplified nucleic acid. DNA strand displacement primers can be used for secondary DNA strand displacement and strand displacement cascade amplification, both described below and in U.S. Pat. No. 6,143,495.

F. RNA Molecules

The disclosed method can involve the use of RNA molecules and RNA sequences. RNA molecules serve as the template for reverse transcription to produce first strand cDNA molecules. As used herein, unless the context indicates otherwise, the term RNA molecule refers to both actual molecules and to RNA sequences that are part of a larger RNA molecule. RNA molecules and sequences can be from any nucleic acid sample of interest or any RNA sample of interest. The source, identity, and preparation of many such nucleic acid or RNA samples are known. It is useful if nucleic acid or RNA samples known or identified for use in amplification or detection methods are used for the method described herein. The nucleic acid or RNA sample can be, for example, a nucleic acid sample from one or more cells, tissue, or bodily fluids such as blood, urine, semen, lymphatic fluid, cerebrospinal fluid, or amniotic fluid, or other biological samples, such as tissue culture cells, buccal swabs, mouthwash, stool, tissues slices, biopsy aspiration, and archeological samples such as bone or mummified tissue. Types of useful nucleic acid or RNA samples include blood samples, urine samples, semen samples, lymphatic fluid samples, cerebrospinal fluid samples, amniotic fluid samples, biopsy samples, needle aspiration biopsy samples, cancer samples, tumor samples, tissue samples, cell samples, cell lysate samples, a crude cell lysate samples, forensic samples, archeological samples, infection samples, nosocomial infection samples, production samples, drug preparation samples, biological molecule production samples, protein preparation samples, lipid preparation samples, and/or carbohydrate preparation samples.

Any RNA molecule can be used in the disclosed method. Examples include mRNA molecules, polyadenylated RNA molecules, rRNA molecules, tRNA molecules, snRNA molecules, precursor RNA molecules, mitochondiral RNA molecules, chloroplast RNA molecules, bacterial RNA molecules, phage RNA molecules, viral RNA molecules, eubacterial RNA molecules, archae bacterial RNA molecules, fungal RNA molecules, microbial RNA molecules, eukaryotic RNA molecules, plant RNA molecules, animal RNA molecules, vertebrate RNA molecules, invertebrate RNA molecules, insect RNA molecules, mammalian RNA molecules, human RNA molecules, or any combination.

G. RNA Samples

RNA samples can be derived from any source that has, or is suspected of having, RNA molecules. An RNA sample is the source of RNA molecules and RNA sequences. RNA samples can contain, for example, a specific mRNA or pool of mRNA molecules. The RNA sample can contain RNA alone or RNA and any other material. That is, an RNA sample can be any type of sample from any source that has, or is suspected of having, RNA molecules. The RNA sample in certain embodiments can also include chemically synthesized RNA molecules. The RNA sample can include any nucleotide, nucleotide analog, nucleotide substitute or nucleotide conjugate.

The RNA sample can be, for example, an RNA sample from one or more cells, tissue, or bodily fluids such as blood, urine, semen, lymphatic fluid, cerebrospinal fluid, or amniotic fluid, or other biological samples, such as tissue culture cells, buccal swabs, mouthwash, stool, tissues slices, biopsy aspiration, and archeological samples such as bone or mummified tissue. Types of useful RNA samples include blood samples, urine samples, semen samples, lymphatic fluid samples, cerebrospinal fluid samples, amniotic fluid samples, biopsy samples, needle aspiration biopsy samples, cancer samples, tumor samples, tissue samples, cell samples, cell lysate samples, crude cell lysate samples, forensic samples, archeological samples, infection samples, nosocomial infection samples, production samples, drug preparation samples, biological molecule production samples, protein preparation samples, lipid preparation samples, and/or carbohydrate preparation samples.

H. Fluorescent Change Probes and Primers

Fluorescent change probes and fluorescent change primers refer to all probes and primers that involve a change in fluorescence intensity or wavelength based on a change in the form or conformation of the probe or primer and nucleic acid to be detected, assayed or replicated. Examples of fluorescent change probes and primers include molecular beacons, Amplifluors, FRET probes, cleavable FRET probes, TaqMan probes, scorpion primers, fluorescent triplex oligos including but not limited to triplex molecular beacons or triplex FRET probes, fluorescent water-soluble conjugated polymers, PNA probes and QPNA probes.

Fluorescent change probes and primers can be classified according to their structure and/or function. Fluorescent change probes include hairpin quenched probes, cleavage quenched probes, cleavage activated probes, and fluorescent activated probes. Fluorescent change primers include stem quenched primers and hairpin quenched primers. The use of several types of fluorescent change probes and primers are reviewed in Schweitzer and Kingsmore, Curr. Opin. Biotech. 12:21–27 (2001). Hall et al., Proc. Natl. Acad. Sci. USA 97:8272–8277 (2000), describe the use of fluorescent change probes with Invader assays.

Hairpin quenched probes are probes that when not bound to a target sequence form a hairpin structure (and, typically, a loop) that brings a fluorescent label and a quenching moiety into proximity such that fluorescence from the label is quenched. When the probe binds to a target sequence, the stem is disrupted, the quenching moiety is no longer in proximity to the fluorescent label and fluorescence increases. Examples of hairpin quenched probes are molecular beacons, fluorescent triplex oligos, triplex molecular beacons, triplex FRET probes, and QPNA probes.

Cleavage activated probes are probes where fluorescence is increased by cleavage of the probe. Cleavage activated probes can include a fluorescent label and a quenching moiety in proximity such that fluorescence from the label is quenched. When the probe is clipped or digested (typically by the 5'-3' exonuclease activity of a polymerase during amplification), the quenching moiety is no longer in proximity to the fluorescent label and fluorescence increases. TaqMan probes (Holland et al., Proc. Natl. Acad. Sci. USA 88:7276–7280 (1991)) are an example of cleavage activated probes.

Cleavage quenched probes are probes where fluorescence is decreased or altered by cleavage of the probe. Cleavage quenched probes can include an acceptor fluorescent label and a donor moiety such that, when the acceptor and donor are in proximity, fluorescence resonance energy transfer from the donor to the acceptor causes the acceptor to fluoresce. The probes are thus fluorescent, for example, when hybridized to a target sequence. When the probe is clipped or digested (typically by the 5'-3' exonuclease activity of a polymerase during amplification), the donor moiety is no longer in proximity to the acceptor fluorescent label and fluorescence from the acceptor decreases. If the donor moiety is itself a fluorescent label, it can release energy as fluorescence (typically at a different wavelength than the fluorescence of the acceptor) when not in proximity to an acceptor. The overall effect would then be a reduction of acceptor fluorescence and an increase in donor fluorescence. Donor fluorescence in the case of cleavage quenched probes is equivalent to fluorescence generated by cleavage activated probes with the acceptor being the quenching moiety and the donor being the fluorescent label. Cleavable FRET (fluorescence resonance energy transfer) probes are an example of cleavage quenched probes.

Fluorescent activated probes are probes or pairs of probes where fluorescence is increased or altered by hybridization of the probe to a target sequence Fluorescent activated probes can include an acceptor fluorescent label and a donor moiety such that, when the acceptor and donor are in proximity (when the probes are hybridized to a target sequence), fluorescence resonance energy transfer from the donor to the acceptor causes the acceptor to fluoresce. Fluorescent activated probes are typically pairs of probes designed to hybridize to adjacent sequences such that the acceptor and donor are brought into proximity. Fluorescent activated probes can also be single probes containing both a donor and acceptor where, when the probe is not hybridized to a target sequence, the donor and acceptor are not in proximity but where the donor and acceptor are brought into proximity when the probe hybridized to a target sequence. This can be accomplished, for example, by placing the donor and acceptor on opposite ends a the probe and placing target complement sequences at each end of the probe where the target complement sequences are complementary to adjacent sequences in a target sequence. If the donor moiety of a fluorescent activated probe is itself a fluorescent label, it can release energy as fluorescence (typically at a different wavelength than the fluorescence of the acceptor) when not in proximity to an acceptor (that is, when the probes are not hybridized to the target sequence). When the probes hybridize to a target sequence, the overall effect would then be a reduction of donor fluorescence and an increase in acceptor fluorescence. FRET probes are an example of fluorescent activated probes.

Stem quenched primers are primers that when not hybridized to a complementary sequence form a stem structure (either an intramolecular stem structure or an intermolecular stem structure) that brings a fluorescent label and a quenching moiety into proximity such that fluorescence from the label is quenched. When the primer binds to a complementary sequence, the stem is disrupted, the quenching moiety is no longer in proximity to the fluorescent label and fluorescence increases. In the disclosed method, stem quenched primers are used as primers for nucleic acid synthesis and thus become incorporated into the synthesized or amplified nucleic acid. Examples of stem quenched primers are peptide nucleic acid quenched primers and hairpin quenched primers.

Peptide nucleic acid quenched primers are primers associated with a peptide nucleic acid quencher or a peptide nucleic acid fluor to form a stem structure. The primer contains a fluorescent label or a quenching moiety and is associated with either a peptide nucleic acid quencher or a peptide nucleic acid fluor, respectively. This puts the fluorescent label in proximity to the quenching moiety. When the primer is replicated, the peptide nucleic acid is displaced, thus allowing the fluorescent label to produce a fluorescent signal.

Hairpin quenched primers are primers that when not hybridized to a complementary sequence form a hairpin structure (and, typically, a loop) that brings a fluorescent label and a quenching moiety into proximity such that fluorescence from the label is quenched. When the primer binds to a complementary sequence, the stem is disrupted, the quenching moiety is no longer in proximity to the fluorescent label and fluorescence increases. Hairpin quenched primers are typically used as primers for nucleic acid synthesis and thus become incorporated into the synthesized or amplified nucleic acid. Examples of hairpin quenched primers are Amplifluor primers (Nazerenko et al., Nucleic Acids Res. 25:2516–2521 (1997)) and scorpion primers (Thelwell et al., Nucleic Acids Res. 28(19):3752–3761 (2000)).

Cleavage activated primers are similar to cleavage activated probes except that they are primers that are incorporated into replicated strands and are then subsequently cleaved. Little et al., Clin. Chem. 45:777–784 (1999), describe the use of cleavage activated primers.

I. Detection Labels

To aid in detection and quantitation of nucleic acids amplified using the disclosed method, detection labels can be directly incorporated into amplified nucleic acids or can be coupled to detection molecules. As used herein, a detection label is any molecule that can be associated with amplified nucleic acid, directly or indirectly, and which results in a measurable, detectable signal, either directly or indirectly. Many such labels for incorporation into nucleic acids or coupling to nucleic acid probes are known to those of skill in the art. Examples of detection labels suitable for use in the disclosed method are radioactive isotopes, fluorescent molecules, phosphorescent molecules, enzymes, antibodies, and ligands. Fluorescent labels, especially in the context of fluorescent change probes and primers, are useful for real-time detection of amplification.

Examples of suitable fluorescent labels include fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as quantum dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy Fl, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH-CH3, Diamino Phenyl Oxydiazole (DAO), Dimethylamino-5-Sulphonic acid, Dipyrrometheneboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

Preferred fluorescent labels are fluorescein (5-carboxyfluorescein-N-hydroxysuccinimide ester), rhodamine (5,6-tetramethyl rhodamine), and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. Other examples of fluorescein dyes include 6-carboxyfluorescein (6-FAM), 2',4',1,4,-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7', 8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, OR; and Research Organics, Cleveland, Ohio.

Additional labels of interest include those that provide for signal only when the probe with which they are associated is specifically bound to a target molecule, where such labels include: "molecular beacons" as described in Tyagi & Kramer, Nature Biotechnology (1996) 14:303 and EP 0 070 685 B1. Other labels of interest include those described in U.S. Pat. No. 5,563,037; WO 97/17471 and WO 97/17076.

Labeled nucleotides are a preferred form of detection label since they can be directly incorporated into the amplification products during synthesis. Examples of detection labels that can be incorporated into amplified nucleic acids include nucleotide analogs such as BrdUrd (5-bromodeoxyuridine, Hoy and Schimke, *Mutation Research* 290:217–230 (1993)), aminoallyldeoxyuridine (Henegariu et al., *Nature Biotechnology* 18:345–348 (2000)), 5-methylcytosine (Sano et al., *Biochim. Biophys. Acta* 951:157–165 (1988)), bromouridine (Wansick et al., *J. Cell Biology* 122:283–293 (1993)) and nucleotides modified with biotin (Langer et al., *Proc. Natl. Acad. Sci. USA* 78:6633 (1981)) or with suitable haptens such as digoxygenin (Kerkhof, *Anal. Biochem.* 205:359–364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.*, 22:3226–3232 (1994)). A preferred nucleotide analog detection label for DNA is BrdUrd (bromodeoxyuridine, BrdUrd, BrdU, BUdR, Sigma-Aldrich Co). Other preferred nucleotide analogs for incorporation of detection label into DNA are AA-dUTP (aminoallyl-deoxyuridine triphosphate, Sigma-Aldrich Co.), and 5-methyl-dCTP (Roche Molecular Biochemicals). A preferred nucleotide analog for incorporation of detection label into RNA is biotin-16-UTP (biotin-16-uridine-5'-triphosphate, Roche Molecular Biochemicals). Fluorescein, Cy3, and Cy5 can be linked to dUTP for direct labeling. Cy3.5 and Cy7 are available as avidin or anti-digoxygenin conjugates for secondary detection of biotin- or digoxygenin-labeled probes.

Detection labels that are incorporated into amplified nucleic acid, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-dioxetane-3-2'-(5'-chloro)tricyclo [3.3.1.1$^{3,7}$]decane]-4-yl) phenyl phosphate; Tropix, Inc.). Labels can also be enzymes, such as alkaline phosphatase, soybean peroxidase, horseradish peroxidase and polymerases, that can be detected, for example, with chemical signal amplification or by using a substrate to the enzyme which produces light (for example, a chemiluminescent 1,2-dioxetane substrate) or fluorescent signal.

Molecules that combine two or more of these detection labels are also considered detection labels. Any of the known detection labels can be used with the disclosed probes, tags, and method to label and detect nucleic acid amplified using the disclosed method. Methods for detecting and measuring signals generated by detection labels are also known. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary detection label coupled to the antibody. As used herein, detection molecules are molecules which interact with amplified nucleic acid and to which one or more detection labels are coupled.

J. Detection Probes

Detection probes are labeled oligonucleotides having sequence complementary to detection tags on TS-DNA or transcripts of TS-DNA (including tandem repeat transcripts and tandem sequence transcripts). The complementary portion of a detection probe can be any length that supports specific and stable hybridization between the detection probe and the detection tag. For this purpose, a length of 6 to 35 nucleotides is preferred, with a complementary portion of a detection probe 12 to 20 nucleotides long being particularly useful. Detection probes can contain any of the detection labels described herein. Useful labels are biotin and fluorescent molecules. Useful detection probes are fluorescent change probes. A particularly useful detection probe is a molecular beacon (which is a form of fluorescent change probe). Molecular beacons are detection probes labeled with fluorescent moieties where the fluorescent moieties fluoresce only when the detection probe is hybridized (Tyagi and Kramer, *Nature Biotechnology* 14:303–308 (1996)). The use of such probes eliminates the need for removal of unhybridized probes prior to label detection because the unhybridized detection probes will not produce a signal. This is especially useful in multiplex assays.

One form of detection probe, referred to herein as a collapsing detection probe, contains two separate complementary portions. This allows each detection probe to hybridize to two detection tags in TS-DNA. In this way, the detection probe forms a bridge between different parts of the TS-DNA. The combined action of numerous collapsing detection probes hybridizing to TS-DNA will be to form a collapsed network of cross-linked TS-DNA. Collapsed TS-DNA occupies a much smaller volume than free, extended TS-DNA, and includes whatever detection label present on the detection probe. This result is a compact and discrete detectable signal for each TS-DNA. Collapsing TS-DNA is useful both for in situ hybridization applications and for multiplex detection because it allows detectable signals to be spatially separate even when closely packed. Collapsing TS-DNA is described in U.S. Pat. No. 6,143,495.

K. Address Probes

An address probe is an oligonucleotide having a sequence complementary to address tags on TS-DNA or transcripts of TS-DNA (including tandem repeat transcripts and tandem sequence transcripts). The complementary portion of an address probe can be any length that supports specific and stable hybridization between the address probe and the address tag. For this purpose, a length of 6 to 35 nucleotides is preferred, with a complementary portion of an address probe 12 to 18 nucleotides long being particularly useful. Address probe can contain a single complementary portion or multiple complementary portions. Address probes can be coupled, either directly or via a spacer molecule, to a solid-state support. Such a combination of address probe and solid-state support are a useful form of solid-state detector. Address probes can be fluorescent change probes although this is not preferred.

L. Solid Supports

Solid supports are solid-state substrates or supports with which amplification products of the disclosed method (or other components used in, or produced by, the disclosed method) can be associated. Amplification products can be associated with solid supports directly or indirectly. For example, amplification products can be bound to the surface of a solid support or associated with address probes, or detection probes immobilized on solid supports. An array detector is a solid support to which multiple different address probes and/or detection probes have been coupled in an array, grid, or other organized pattern. RNA molecules and RNA sequences can also be attached to solid supports.

Solid-state substrates for use in solid supports can include any solid material with which components can be associated, directly or indirectly. This includes materials such as acrylamide, agarose, cellulose, nitrocellulose, glass, gold, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, functionalized silane, polypropylfumerate, collagen, glycosaminoglycans, and polyamino acids. Solid-state substrates can have any useful form including thin film, membrane, bottles, dishes, fibers, woven fibers, shaped polymers, particles, beads, microparticles, or a combination. Solid-state substrates and solid supports can be porous or non-porous. A chip is a rectangular or square small piece of material. Preferred forms for solid-state substrates are thin films, beads, or chips. A useful form for a solid-state substrate is a microtiter dish. In some embodiments, a multiwell glass slide can be employed.

Different address probes and/or detection probes can be used together as a set. The set can be used as a mixture of all or subsets of the address probes and/or detection probes used separately in separate reactions, or immobilized on a solid support. Address probes and/or detection probes used separately or as mixtures can be physically separable through, for example, association with or immobilization on a solid support. An array can include a plurality of address probes and/or detection probes immobilized at identified or predefined locations on the solid support. Each predefined location on the solid support generally has one type of component (that is, all the components at that location are the same). Alternatively, multiple types of components can be immobilized in the same predefined location on a solid support. Each location will have multiple copies of the given components. The spatial separation of different components on the solid support allows separate detection and identification of amplification products.

Although useful, it is not required that the solid support be a single unit or structure. The set of address probes and/or detection probes may be distributed over any number of solid supports. For example, at one extreme, each probe may be immobilized in a separate reaction tube or container, or on separate beads or microparticles.

Methods for immobilization of oligonucleotides to solid-state substrates are well established. Oligonucleotides, including address probes and detection probes, can be coupled to substrates using established coupling methods. For example, suitable attachment methods are described by Pease et al., *Proc. Natl. Acad. Sci. USA* 91(11):5022–5026 (1994), and Khrapko et al., *Mol Biol (Mosk) (USSR)* 25:718–730 (1991). A method for immobilization of 3'-amine oligonucleotides on casein-coated slides is described by Stimpson et al., *Proc. Natl. Acad. Sci. USA* 92:6379–6383 (1995). A useful method of attaching oligonucleotides to solid-state substrates is described by Guo et al., *Nucleic Acids Res.* 22:5456–5465 (1994).

Each of the components (for example, address probes and/or detection probes) immobilized on the solid support can be located in a different predefined region of the solid support. The different locations can be different reaction chambers. Each of the different predefined regions can be physically separated from each of the other different regions. The distance between the different predefined regions of the solid support can be either fixed or variable. For example, in an array, each of the components can be arranged at fixed distances from each other, while components associated with beads will not be in a fixed spatial relationship. In particular, the use of multiple solid support units (for example, multiple beads) will result in variable distances.

Components can be associated or immobilized on a solid support at any density. Components can be immobilized to the solid support at a density exceeding 400 different components per cubic centimeter. Arrays of components can have any number of components. For example, an array can have at least 1,000 different components immobilized on the solid support, at least 10,000 different components immobilized on the solid support, at least 100,000 different components immobilized on the solid support, or at least 1,000,000 different components immobilized on the solid support.

Nucleic acids produced in the disclosed method can be associated with or immobilized on a solid-state substrate or solid support. For example tandem repeat units or tandem repeat transcripts can be attached to a support and used as probes in hybridization assays. The tandem repeat units or tandem repeat transcripts can serve as a probe library representing the RNA sequences in the RNA sample that was the source for amplification.

M. Solid-State Detectors

Solid-state detectors are solid supports to which address probes or detection molecules have been coupled. A preferred form of solid-state detector is an array detector. An array detector is a solid-state detector to which multiple different address probes and/or detection molecules have been coupled in an array, grid, or other organized pattern.

Solid-state substrates for use in solid-state detectors can include any solid material to which oligonucleotides can be coupled. This includes materials such as acrylamide, agarose, cellulose, nitrocellulose, glass, gold, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, functionalized silane, polypropylfumerate, collagen, glycosaminoglycans, and polyamino acids. Solid-state substrates can have any useful form including thin film, membrane, bottles, dishes, fibers, woven fibers, shaped polymers, particles, beads, microparticles, or a combination. Solid-state substrates and solid supports can be porous or non-porous. A chip is a rectangular or square small piece of material. Preferred forms for solid-state substrates are thin films, beads, or chips. A useful form for a solid-state substrate is a microtiter dish. In some embodiments, a multiwell glass slide can be employed.

Address probes immobilized on a solid-state substrate allow capture of the products of the disclosed amplification method on a solid-state detector. Such capture provides a convenient means of washing away reaction components that might interfere with subsequent detection steps. By attaching different address probes to different regions of a solid-state detector, different amplification products can be captured at different, and therefore diagnostic, locations on the solid-state detector. For example, in a multiplex assay, address probes specific for numerous different amplified nucleic acids (each representing a different RNA molecule) can be immobilized in an array, each in a different location. Capture and detection will occur only at those array locations corresponding to amplified nucleic acids for which the corresponding RNA molecules were present in a sample.

Methods for immobilization of oligonucleotides to solid-state substrates are well established. Oligonucleotides, including address probes and detection probes, can be coupled to substrates using established coupling methods. For example, suitable attachment methods are described by Pease et al., *Proc. Natl. Acad. Sci. USA* 91(11):5022–5026 (1994), and Khrapko et al., *Mol Biol (Mosk) (USSR)* 25:718–730 (1991). A method for immobilization of 3'-amine oligonucleotides on casein-coated slides is described by Stimpson et al., *Proc. Natl. Acad. Sci. USA* 92:6379–6383 (1995). A preferred method of attaching oligonucleotides to solid-state substrates is described by Guo et al., *Nucleic Acids Res.* 22:5456–5465 (1994). Examples of nucleic acid chips and arrays, including methods of making and using such chips and arrays, are described in U.S. Pat. No. 6,287,768, U.S. Pat. No. 6,288,220, U.S. Pat. No. 6,287,776, U.S. Pat. No. 6,297,006, and U.S. Pat. No. 6,291,193.

Some solid-state detectors useful in the disclosed method have detection antibodies attached to a solid-state substrate. Such antibodies can be specific for a molecule of interest. Captured molecules of interest can then be detected by binding of a second, reporter antibody, followed by amplification. Such a use of antibodies in a solid-state detector allows amplification assays to be developed for the detection of any molecule for which antibodies can be generated. Methods for immobilizing antibodies to solid-state substrates are well established. Immobilization can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidin-biotin, photocrosslinkable agents, epoxides and maleimides. A preferred attachment agent is glutaraldehyde. These and other attachment agents, as well as methods for their use in attachment, are described in *Protein immobilization: fundamentals and applications*, Richard F. Taylor, ed. (M. Dekker, New York, 1991), Johnstone and Thorpe, *Immunochemistry In Practice* (Blackwell Scientific Publications, Oxford, England, 1987) pages 209–216 and 241–242, and *Immobilized Affinity Ligands*, Craig T. Hermanson et al., eds. (Academic Press, New York, 1992). Antibodies can be attached to a substrate by chemically cross-linking a free amino group on the antibody to reactive side groups present within the solid-state substrate. For example, antibodies may be chemically cross-linked to a substrate that contains free amino or carboxyl groups using glutaraldehyde or carbodiimides as cross-linker agents. In this method, aqueous solutions containing free antibodies are incubated with the solid-state substrate in the presence of glutaraldehyde or carbodiimide. For crosslinking with glutaraldehyde the reactants can be incubated with 2% glutaraldehyde by volume in a buffered solution such as 0.1 M sodium cacodylate at pH 7.4. Other standard immobilization chemistries are known by those of skill in the art.

N. Solid-State Samples

Solid-state samples are solid supports to which RNA molecules or RNA sequences have been coupled or adhered. RNA molecules or RNA sequences are preferably delivered in an RNA sample. A useful form of solid-state sample is an array sample. An array sample is a solid-state sample to which multiple different RNA samples have been coupled or adhered in an array, grid, or other organized pattern.

Solid-state substrates for use in solid-state samples can include any solid material to which RNA molecules or RNA sequences can be coupled or adhered. This includes materials such as acrylamide, agarose, cellulose, nitrocellulose, glass, gold, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, functionalized silane, polypropylfumerate, collagen, glycosaminoglycans, and polyamino acids. Solid-state substrates can have any useful form including thin film, membrane, bottles, dishes, fibers, woven fibers, shaped polymers, particles, beads, microparticles, or a combination. Solid-state substrates and solid supports can be porous or non-porous. A chip is a rectangular or square small piece of material. Preferred forms for solid-state substrates are thin films, beads, or chips. A useful form for a solid-state substrate is a microtiter dish. In some embodiments, a multiwell glass slide can be employed.

Nucleic acids produced in the disclosed method can be coupled or adhered to a solid-state substrate in any suitable way. For example, nucleic acids generated by rolling circle amplification or multiple strand displacement amplification of first strand cDNA molecules can be attached by adding modified nucleotides to the 3' ends of nucleic acids produced in the reaction using terminal deoxynucleotidyl transferase, and reacting the modified nucleotides with a solid-state substrate or support thereby attaching the nucleic acids to the solid-state substrate or support.

A useful form of solid-state substrate is a glass slide to which up to 256 separate RNA samples have been adhered as an array of small dots. Each dot is preferably from 0.1 to 2.5 mm in diameter, and most preferably around 2.5 mm in diameter. Such microarrays can be fabricated, for example, using the method described by Schena et al., *Science* 270:487–470 (1995). Briefly, microarrays can be fabricated on poly-L-lysine-coated microscope slides (Sigma) with an arraying machine fitted with one printing tip. The tip is loaded with 1 µl of an RNA sample (0.5 mg/ml) from, for example, 96-well microtiter plates and deposited ~0.005 µl per slide on multiple slides at the desired spacing. The printed slides can then be rehydrated for 2 hours in a humid chamber, snap-dried at 100° C. for 1 minute, rinsed in 0.1% SDS, and treated with 0.05% succinic anhydride prepared in buffer consisting of 50% 1-methyl-2-pyrrolidinone and 50% boric acid. The RNA on the slides can then be denatured in, for example, distilled water for 2 minutes at 90° C. immediately before use. Microarray solid-state samples can scanned with, for example, a laser fluorescent scanner with a computer-controlled XY stage and a microscope objective. A mixed gas, multiline laser allows sequential excitation of multiple fluorophores.

O. Reverse Transcriptases

Reverse transcriptases useful in the disclosed method can be any polymerase that exhibits reverse transcriptase activity. The catalytic activities useful in the disclosed method are an RNA-dependent DNA polymerase activity. The reverse transcriptase can have a RNAse H activity or can lack an RNAse activity. It is preferred that a reverse transcriptase lacking an RNAse H activity be sued to synthesize the first strand cDNA molecules. The RNA template can then be digested by RNAse H or a reverse transcriptase having an RNAse H activity. Because the disclosed method generally does not involve second strand synthesis, the reverse transcriptase need not have a DNA-dependent DNA polymerase activity. Most reverse transcriptases, including those derived from Moloney murine leukemia virus (MMLV-RT), avian myeloblastosis virus (AMV-RT), bovine leukemia virus (BLV-RT), Rous sarcoma virus (RSV) and human immunodeficiency virus (HIV-RT) have each of these activities. A useful reverse transcriptase for synthesis of first strand cDNA molecules is Superscript II reverse transcriptase (Invitrogen). Many other reverse transcriptases are known (available from, for example, Invitrogen, Clontech, Boehringer Mannheim Corp., Indianapolis, Ind.; Life Technologies, Inc., Rockville, Md.; New England Biolabs, Inc., Beverley, Mass.; Perkin Elmer Corp., Norwalk, Conn.; Pharmacia LKB Biotechnology, Inc., Piscataway, N.J.; Qiagen, Inc., Valencia, Calif.; Stratagene, La Jolla, Calif.) .which can be used in the disclosed method. A variety of proteins that catalyze one or two of these activities can be added to the cDNA synthesis reaction. For example, Superscript II reverse transcriptase which lacks RNAse H activity and which has RNA-dependent DNA polymerase activity, can be added with a source of RNAse H activity, such as the RNAse H purified from cellular sources, including *Escherichia coli*. These proteins may be added together during a single reaction step, or added sequentially during two or more substeps. Finally, additional proteins that may enhance the yield of cDNA products may also be added to the cDNA synthesis reaction. These proteins include a variety of DNA polymerases (such as those derived from *E. coli*, thermophilic bacteria, archaebacteria, phage, yeasts, Neurosporas, Drosophilas, primates and rodents), and DNA Ligases (such as those derived from phage or cellular sources, including T4 DNA Ligase and *E. coli* DNA Ligase).

P. DNA Polymerases

DNA polymerases useful in the rolling circle replication step of the disclosed method must perform rolling circle replication of primed circular templates. Such polymerases are referred to herein as rolling circle DNA polymerases. For rolling circle replication, it is preferred that a DNA polymerase be capable of displacing the strand complementary to the template strand, termed strand displacement, and lack a 5' to 3' exonuclease activity. Strand displacement is necessary to result in synthesis of multiple tandem copies of the circularized first strand cDNA molecules. A 5' to 3' exonuclease activity, if present, might result in the destruction of the synthesized strand. DNA polymerases for use in the disclosed method can also be highly processive, if desired. The suitability of a DNA polymerase for use in the disclosed method can be readily determined by assessing its ability to carry out rolling circle replication. Preferred rolling circle DNA polymerases are bacteriophage φ29 DNA polymerase (U.S. Pat. Nos. 5,198,543 and 5,001,050 to Blanco et al.), Bst DNA polymerase, VENT® DNA polymerase (Kong et al., *J. Biol. Chem.* 268:1965–1975 (1993)), ThermoSequenase™, delta Tts DNA polymerase, Bca DNA polymerase (Journal of Biochemistry 113(3):401–10, 1993 March), phage M2 DNA polymerase (Matsumoto et al., *Gene* 84:247 (1989)), phage φPRD1 DNA polymerase (Jung et al., *Proc. Natl. Acad. Sci. USA* 84:8287 (1987)), Klenow fragment of DNA polymerase I (Jacobsen et al., *Eur. J. Biochem.* 45:623–627 (1974)), T5 DNA polymerase (Chatterjee et al., *Gene* 97:13–19 (1991)), PRD1 DNA polymerase (Zhu and Ito, *Biochim. Biophys. Acta.* 1219:267–276 (1994)), modified T7 DNA polymerase (Tabor and Richardson, *J. Biol. Chem.* 262:15330–15333 (1987); Tabor and Richardson, *J. Biol. Chem.* 264:6447–6458 (1989); Sequenase™ (U.S. Biochemicals)), and T4 DNA polymerase holoenzyme (Kaboord and Benkovic, *Curr. Biol.* 5:149–157 (1995)). More preferred are bacteriophage φ29 DNA polymerase, Bst DNA polymerase, VENT® DNA polymerase, ThermoSequenase™, and delta Tts DNA polymerase. φ29 DNA polymerase is most preferred.

Strand displacement can be facilitated through the use of a strand displacement factor, such as helicase. It is considered that any DNA polymerase that can perform rolling circle replication in the presence of a strand displacement factor is suitable for use in the disclosed method, even if the DNA polymerase does not perform rolling circle replication in the absence of such a factor. Strand displacement factors useful in the disclosed method include BMRF1 polymerase accessory subunit (Tsurumi et al., *J. Virology* 67(12):7648–7653 (1993)), adenovirus DNA-binding protein (Zijderveld and van der Vliet, *J. Virology* 68(2):1158–1164 (1994)), herpes simplex viral protein ICP8 (Boehmer and Lehman, *J. Virology* 67(2):711–715 (1993); Skaliter and Lehman, *Proc. Natl. Acad. Sci. USA* 91(22):10665–10669 (1994)), single-stranded DNA binding proteins (SSB; Rigler and Romano, *J. Biol. Chem.* 270:8910–8919 (1995)), and calf thymus helicase (Siegel et al., *J. Biol. Chem.* 267:13629–13635 (1992)).

The ability of a polymerase to carry out rolling circle replication can be determined by using the polymerase in a rolling circle replication assay such as those described in Fire and Xu, *Proc. Natl. Acad. Sci. USA* 92:4641–4645 (1995) and in U.S. Pat. No. 6,143,495 (Example 1).

DNA polymerases useful in multiple strand displacement amplification must be capable of displacing, either alone or in combination with a compatible strand displacement factor, a hybridized strand encountered during replication. Such polymerases are referred to herein as strand displacement DNA polymerases. It is preferred that a strand displacement DNA polymerase lack a 5' to 3' exonuclease activity. Strand displacement is necessary to result in synthesis of multiple copies of a target sequence. A 5' to 3' exonuclease activity, if present, might result in the destruction of a synthesized strand. It is also preferred that DNA polymerases for use in the disclosed method are highly processive. The suitability of a DNA polymerase for use in the disclosed method can be readily determined by assessing its ability to carry out strand displacement replication. Preferred strand displacement DNA polymerases are bacteriophage φ29 DNA polymerase (U.S. Pat. Nos. 5,198,543 and 5,001,050 to Blanco et al.), Bst large fragment DNA polymerase (Exo(–) Bst; Aliotta et al., *Genet. Anal. (Netherlands)* 12:185–195 (1996)) and exo(–)Bca DNA polymerase (Walker and Linn, *Clinical Chemistry* 42:1604–1608 (1996)). Other useful polymerases include phage M2 DNA polymerase (Matsumoto et al., *Gene* 84:247 (1989)), phage φPRD1 DNA polymerase (Jung et al., *Proc. Natl. Acad. Sci. USA* 84:8287 (1987)), exo(–)VENT® DNA polymerase (Kong et al., *J. Biol. Chem.* 268:1965–1975 (1993)), Klenow fragment of DNA polymerase I (Jacobsen et al., *Eur. J. Biochem.* 45:623–627 (1974)), T5 DNA polymerase (Chatterjee et al., *Gene* 97:13–19 (1991)), Sequenase (U.S. Biochemicals), PRD1 DNA polymerase (Zhu and Ito, *Biochim. Biophys. Acta.* 1219:267–276 (1994)), and T4 DNA polymerase holoenzyme (Kaboord and Benkovic, *Curr. Biol.* 5:149–157 (1995)). φ29 DNA polymerase is most preferred.

Strand displacement can be facilitated through the use of a strand displacement factor, such as helicase. It is considered that any DNA polymerase that can perform strand displacement replication in the presence of a strand displacement factor is suitable for use in the disclosed method, even if the DNA polymerase does not perform strand displacement replication in the absence of such a factor. Strand displacement factors useful in strand displacement replication include BMRF1 polymerase accessory subunit (Tsurumi et al., *J. Virology* 67(12):7648–7653 (1993)), adenovirus DNA-binding protein (Zijderveld and van der Vliet, *J. Virology* 68(2):1158–1164 (1994)), herpes simplex viral protein ICP8 (Boehmer and Lehman, *J. Virology* 67(2):711–715 (1993); Skaliter and Lehman, *Proc. Natl. Acad. Sci. USA* 91(22):10665–10669 (1994)); single-stranded DNA binding proteins (SSB; Rigler and Romano, *J. Biol. Chem.* 270:8910–8919 (1995)); phage T4 gene 32 protein (Villemain and Giedroc, *Biochemistry* 35:14395–14404 (1996); and calf thymus helicase (Siegel et al., *J. Biol. Chem.* 267:13629–13635 (1992)).

The ability of a polymerase to carry out strand displacement replication can be determined by using the polymerase in a strand displacement replication assay. Such assays should be performed at a temperature suitable for optimal activity for the enzyme being used, for example, 32° C. for φ29 DNA polymerase, from 46° C. to 64° C. for exo(–) Bst DNA polymerase, or from about 60° C. to 70° C. for an enzyme from a hyperthermophylic organism. For assays from 60° C. to 70° C., primer length may be increased to provide a melting temperature appropriate for the assay temperature. A useful assay for selecting a polymerase is the primer-block assay described in Kong et al., *J. Biol. Chem.* 268:1965–1975 (1993). The assay consists of a primer extension assay using an M13 ssDNA template in the presence or absence of an oligonucleotide that is hybridized upstream of the extending primer to block its progress. Enzymes able to displace the blocking primer in this assay are expected to be useful for the disclosed method.

Q. DNA Ligases

Any DNA ligase is suitable for use in the disclosed amplification method. Many suitable ligases are known, such as T4 DNA ligase (Davis et al., *Advanced Bacterial Genetics—A Manual for Genetic Engineering* (Cold Spring Harbor Laboratory, Cold Spring Harbor, N.Y., 1980)), *E. coli* DNA ligase (Panasnko et al., *J. Biol. Chem.* 253:4590–4592 (1978)), AMPLIGASE® (Kalin et al., *Mutat. Res.*, 283(2):119–123 (1992); Winn-Deen et al., *Mol Cell Probes* (England) 7(3):179–186 (1993)), Taq DNA ligase (Barany, *Proc. Natl. Acad. Sci. USA* 88:189–193 (1991), *Thermus thermophilus* DNA ligase (Abbott Laboratories), *Thermus scotoductus* DNA ligase and *Rhodothermus marinus* DNA ligase (Thorbjarnardottir et al., *Gene* 151:177–180 (1995)). T4 DNA ligase is preferred.

R. RNA Polymerases

Any RNA polymerase which can carry out transcription in vitro and for which promoter sequences have been identified can be used in or with the disclosed method. Stable RNA polymerases without complex requirements are preferred. Most preferred are T3 RNA polymerase, T7 RNA polymerase (Davanloo et al., *Proc. Natl. Acad. Sci. USA* 81:2035–2039 (1984)), and SP6 RNA polymerase (Butler and Chamberlin, *J. Biol. Chem.* 257:5772–5778 (1982)) which are highly specific for particular promoter sequences (Schenborn and Meirendorf, *Nucleic Acids Research* 13:6223–6236 (1985)). Other RNA polymerases with this characteristic are also preferred. Because promoter sequences are generally recognized by specific RNA polymerases, the first strand cDNA molecules and/or TS-DNA should contain a promoter sequence recognized by the RNA polymerase that is used. Numerous promoter sequences are known and any suitable RNA polymerase having an identified promoter sequence can be used. Promoter sequences for RNA polymerases can be identified using established techniques.

S. Oligonucleotide Synthesis

Circularization probes, cDNA primers, rolling circle replication primers, detection probes, address probes, DNA strand displacement primers and any other oligonucleotides can be synthesized using established oligonucleotide synthesis methods. Methods to produce or synthesize oligonucleotides are well known. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method. Solid phase chemical synthesis of DNA fragments is routinely performed using protected nucleoside cyanoethyl phosphoramidites (S. L. Beaucage et al. (1981) Tetrahedron Lett. 22:1859). In this approach, the 3'-hydroxyl group of an initial 5'-protected nucleoside is first covalently attached to the polymer support (R. C. Pless et al. (1975) Nucleic Acids Res. 2:773 (1975)). Synthesis of the oligonucleotide then proceeds by deprotection of the 5'-hydroxyl group of the attached nucleoside, followed by coupling of an incoming nucleoside-3'-phosphoramidite to the deprotected hydroxyl group (M. D. Matteucci et a. (1981) J. Am. Chem. Soc. 103:3185). The resulting phosphite triester is finally oxidized to a phosphorotriester to complete the internucleotide bond (R. L. Letsinger et al. (1976) J. Am. Chem. Soc. 9:3655). Alternatively, the synthesis of phosphorothioate linkages can be carried out by sulfurization of the phosphite triester. Several chemicals can be used to perform this reaction, among them 3H-1,2-benzodithiole-3-one, 1,1-dioxide (R. P. Iyer, W. Egan, J. B. Regan, and S. L. Beaucage, J. Am. Chem. Soc., 1990, 112, 1253–1254). The steps of deprotection, coupling and oxidation are repeated until an oligonucleotide of the desired length and sequence is obtained. Other methods exist to generate oligonucleotides such as the H-phosphonate method (Hall et al, (1957) J. Chem. Soc., 3291–3296) or the phosphotriester method as described by Ikuta et al., *Ann. Rev. Biochem.* 53:323–356 (1984), (phosphotriester and phosphite-triester methods), and Narang et al., *Methods Enzymol.*, 65:610–620 (1980), (phosphotriester method). Protein nucleic acid molecules can be made using known methods such as those described by Nielsen et al., *Bioconjug. Chem.* 5:3–7 (1994). Other forms of oligonucleotide synthesis are described in U.S. Pat. No. 6,294,664 and U.S. Pat. No. 6,291,669.

The nucleotide sequence of an oligonucleotide is generally determined by the sequential order in which subunits of subunit blocks are added to the oligonucleotide chain during synthesis. Each round of addition can involve a different, specific nucleotide precursor, or a mixture of one or more different nucleotide precursors. In general, degenerate or random positions in an oligonucleotide can be produced by using a mixture of nucleotide precursors representing the range of nucleotides that can be present at that position. Thus, precursors for A and T can be included in the reaction for a particular position in an oligonucleotide if that position is to be degenerate for A and T. Precursors for all four nucleotides can be included for a fully degenerate or random position. Completely random oligonucleotides can be made by including all four nucleotide precursors in every round of synthesis. Degenerate oligonucleotides can also be made having different proportions of different nucleotides. Such oligonucleotides can be made, for example, by using different nucleotide precursors, in the desired proportions, in the reaction.

Many of the oligonucleotides described herein are designed to be complementary to certain portions of other oligonucleotides or nucleic acids such that stable hybrids can be formed between them. The stability of these hybrids can be calculated using known methods such as those described in Lesnick and Freier, *Biochemistry* 34:10807–10815 (1995), McGraw et al., *Biotechniques* 8:674–678 (1990), and Rychlik et al., *Nucleic Acids Res.* 18:6409–6412 (1990).

Oligonucleotides can be synthesized, for example, on a Perseptive Biosystems 8909 Expedite Nucleic Acid Synthesis system using standard β-cyanoethyl phosphoramidite coupling chemistry on synthesis columns (Glen Research, Sterling, Va.). Oxidation of the newly formed phosphites can be carried out using, for example, the sulfurizing reagent 3H-1,2-benzothiole-3-one-1,1-idoxide (Glen Research) or the standard oxidizing reagent after the first and second phosphoramidite addition steps. The thio-phosphitylated oligonucleotides can be deprotected, for example, using 30% ammonium hydroxide (3.0 ml) in water at 55° C. for 16 hours, concentrated in an OP 120 Savant Oligo Prep deprotection unit for 2 hours, and desalted with PD10 Sephadex columns using the protocol provided by the manufacturer.

Random hexamer oligonucleotides can be synthesized on a Perseptive Biosystems 8909 Expedite Nucleic Acid Synthesis system using standard β-cyanoethyl phosphoramidite coupling chemistry on mixed dA+dC+dG+dT synthesis columns (Glen Research, Sterling, Va.). The four phosphoramidites can be mixed in equal proportions to randomize the bases at each position in the oligonucleotide. Oxidation of the newly formed phosphites can be carried out using the sulfurizing reagent 3H-1,2-benzothiole-3-one-1,1-idoxide (Glen Research) instead of the standard oxidizing reagent after the first and second phosphoramidite addition steps. The thio-phosphitylated oligonucleotides can be deprotected using 30% ammonium hydroxide (3.0 ml) in water at 55° C. for 16 hours, concentrated in an OP 120 Savant Oligo Prep deprotection unit for 2 hours, and desalted with PD 10 Sephadex columns using the protocol provided by the manufacturer.

So long as their relevant function is maintained, cDNA primers, circularization probes, rolling circle replication primers, detection probes, address probes, DNA strand displacement primers and any other oligonucleotides can be made up of or include modified nucleotides (nucleotide analogs). Many modified nucleotides are known and can be used in oligonucleotides. A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl, hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine.

Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289–302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Other modified bases are those that function as universal bases. Universal bases include 3-nitropyrrole and 5-nitroindole. Universal bases substitute for the normal bases but have no bias in base pairing. That is, universal bases can base pair with any other base. Base modifications often can be combined with for example a sugar modification, such as 2'-O-methoxyethyl, to achieve unique properties such as increased duplex stability. There are numerous United States patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, which detail and describe a range of base modifications. Each of these patents is herein incorporated by reference in its entirety, and specifically for their description of base modifications, their synthesis, their use, and their incorporation into oligonucleotides and nucleic acids.

Nucleotide analogs can also include modifications of the sugar moiety. Modifications to the sugar moiety would include natural modifications of the ribose and deoxyribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$, alkyl or $C_2$ to $C_{10}$ alkenyl and alkynyl. 2' sugar modifications also include but are not limited to —O[$(CH_2)_n$ O]$_m$ $CH_3$, —O$(CH_2)_n$ $OCH_3$, —O$(CH_2)_n$ $NH_2$, —O$(CH_2)_n$ $CH_3$, —O$(CH_2)_n$ —$ONH_2$, and —O$(CH_2)_n$ON[$(CH_2)_n$ $CH_3$)]$_2$, where n and m are from 1 to about 10.

Other modifications at the 2' position include but are not limited to: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2$ $CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as $CH_2$ and S. Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety, and specifically for their description of modified sugar structures, their synthesis, their use, and their incorporation into nucleotides, oligonucleotides and nucleic acids.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkages between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference its entirety, and specifically for their description of modified phosphates, their synthesis, their use, and their incorporation into nucleotides, oligonucleotides and nucleic acids.

It is understood that nucleotide analogs need only contain a single modification, but may also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize and hybridize to (base pair to) complementary nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086;

5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference its entirety, and specifically for their description of phosphate replacements, their synthesis, their use, and their incorporation into nucleotides, oligonucleotides and nucleic acids.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. (See also Nielsen et al., *Science* 254:1497–1500 (1991)).

Oligonucleotides can be comprised of nucleotides and can be made up of different types of nucleotides or the same type of nucleotides. For example, one or more of the nucleotides in an oligonucleotide can be ribonucleotides, 2'-O-methyl ribonucleotides, or a mixture of ribonucleotides and 2'-O-methyl ribonucleotides; about 10% to about 50% of the nucleotides can be ribonucleotides, 2'-O-methyl ribonucleotides, or a mixture of ribonucleotides and 2'-O-methyl ribonucleotides; about 50% or more of the nucleotides can be ribonucleotides, 2'-O-methyl ribonucleotides, or a mixture of ribonucleotides and 2'-O-methyl ribonucleotides; or all of the nucleotides are ribonucleotides, 2'-O-methyl ribonucleotides, or a mixture of ribonucleotides and 2'-O-methyl ribonucleotides. Such oligonucleotides can be referred to as chimeric oligonucleotides.

T. cDNA Libraries

The disclosed method can be used to produce replicated strands that serve as a cDNA library of an RNA sample. Such a cDNA library can be used for any purpose, including, for example, detection of sequences, production of probes, production of nucleic acid arrays or chips, and comparison with nucleic acids in other nucleic acid and/or cDNA libraries. A cDNA library can include, for example, all or a portion of the first strand cDNA molecules produced from one or more RNA samples, all or a portion of the tandem sequence DNA produced from all or a portion of the first strand cDNA molecules produced from one or more RNA samples, all or a portion of the tandem repeat units produced from all or a portion of the tandem sequence DNA produced from all or a portion of the first strand cDNA molecules produced from one or more RNA samples, cloned cDNA molecules, where the cDNA molecules are derived from all or a portion of the first strand cDNA molecules produced from one or more RNA samples, cDNA molecules inserted into vectors, where the cDNA molecules are derived from all or a portion of the first strand cDNA molecules produced from one or more RNA samples, cloned tandem repeat units, where the tandem repeat units are produced from all or a portion of the tandem sequence DNA produced from all or a portion of the first strand cDNA molecules produced from one or more RNA samples, and tandem repeat units inserted into vectors, where the tandem repeat units are produced from all or a portion of the tandem sequence DNA produced from all or a portion of the first strand cDNA molecules produced from one or more RNA samples. The disclosed cDNA libraries can be used to produce transcripts of the cDNA (for example, tandem sequence transcripts and tandem repeat transcripts).

Tandem repeat units that constitute, or that can be used to make, a cDNA library can be made from double-stranded tandem sequence DNA. Tandem sequence DNA produced in the disclosed method can include cleavage sites as described elsewhere herein. These cleavage sites, which preferably occur once in every tandem repeat, can be used to digest the tandem sequence DNA into single tandem repeat units. Single tandem repeat units are essentially cDNA molecules of a single RNA molecule (that is, the equivalent of a traditional cDNA molecule). These tandem repeat units can be manipulated, used, stored, cloned and inserted into vectors in all of the ways that traditional cDNA molecules can. The important difference in the disclosed method is that the number of tandem repeat units is greatly amplified over the number of RNA molecules from which they were derived. This, combined with the high sequence representation and low amplification bias of the disclosed method, provide a more robust cDNA library than other techniques. The disclosed method produces, for example, cDNA libraries with good representation of low abundance RNA molecules.

Similarly prepared cDNA libraries of other RNA samples allow convenient detection of differences between the samples. The cDNA libraries can be used both for detection of related RNA samples and comparison of RNA samples. For example, the presence or identity of specific organisms can be detected by producing a cDNA library of the test organism and comparing the resulting cDNA library with reference cDNA libraries prepared from known organisms. Changes and differences in gene expression patterns can also be detected by preparing cDNA libraries of mRNA from different cell samples and comparing the cDNA libraries. The replicated strands can also be used to produce a set of probes or primers that is specific for the source of a RNA sample. The replicated strands can also be used as a fingerprint of nucleic acid sequences present in a sample. cDNA libraries can be made up of, or derived from, the mRNA of a sample such that the entire relevant mRNA content of the sample is substantially represented.

cDNA libraries can be stored or archived for later use. For example, replicated strands produced in the disclosed method can be physically stored, either in solution, frozen, or attached or adhered to a solid-state substrate such as an array. Storage in an array is useful for providing an archived probe set derived from the nucleic acids in any sample of interest. As another example, informational content of, or derived from, nucleic acid fingerprints can also be stored. Such information can be stored, for example, in or as computer readable media. Examples of informational content of cDNA libraries include nucleic acid sequence information (complete or partial); differential nucleic acid sequence information such as sequences present in one sample but not another; hybridization patterns of replicated strands to, for example, nucleic acid arrays, sets, chips, or other replicated strands. Numerous other data that is or can be derived from cDNA libraries and replicated strands produced in the disclosed method can also be collected, used, saved, stored, and/or archived.

cDNA libraries can also contain or be made up of other information derived from the information generated in the disclosed method, and can be combined with information obtained or generated from any other source. The informational nature of cDNA libraries produced using the disclosed method lends itself to combination and/or analysis using known bioinformatics systems and methods.

cDNA libraries of RNA samples can be compared to a similar cDNA library derived from any other sample to detect similarities and differences in the samples (which is indicative of similarities and differences in the nucleic acids in the samples). For example, a cDNA library of a first RNA sample can be compared to a cDNA library of a sample from the same type of organism as the first RNA sample, a sample from the same type of tissue as the first RNA sample, a sample from the same organism as the first RNA sample, a sample obtained from the same source but at time different from that of the first RNA sample, a sample from an organism different from that of the first RNA sample, a sample from a type of tissue different from that of the first RNA sample, a sample from a strain of organism different from that of the first RNA sample, a sample from a species of organism different from that of the first RNA sample, or a sample from a type of organism different from that of the first RNA sample.

The same type of tissue is tissue of the same type such as liver tissue, muscle tissue, or skin (which may be from the same or a different organism or type of organism). The same organism refers to the same individual, animal, or cell. For example, two samples taken from a patient are from the same organism. The same source is similar but broader, referring to samples from, for example, the same organism, the same tissue from the same organism, the same RNA molecule, or the same cDNA library. Samples from the same source that are to be compared can be collected at different times (thus allowing for potential changes over time to be detected). This is especially useful when the effect of a treatment or change in condition is to be assessed. Samples from the same source that have undergone different treatments can also be collected and compared using the disclosed method. A different organism refers to a different individual organism, such as a different patient, a different individual animal. Different organism includes a different organism of the same type or organisms of different types. A different type of organism refers to organisms of different types such as a dog and cat, a human and a mouse, or *E. coli* and *Salmonella*. A different type of tissue refers to tissues of different types such as liver and kidney, or skin and brain. A different strain or species of organism refers to organisms differing in their species or strain designation as those terms are understood in the art.

cDNA molecules, tandem sequence DNA, and cDNA libraries can be used to produce transcripts. Such transcripts can include, for example, all or a portion of the tandem sequence transcripts produced from all or a portion of the tandem sequence DNA produced from all or a portion of the first strand cDNA molecules produced from one or more RNA samples, and all or a portion of the tandem repeat transcripts produced from all or a portion of the tandem repeat units produced from all or a portion of the tandem sequence DNA produced from all or a portion of the first strand cDNA molecules produced from one or more RNA samples.

U. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for amplification of RNA sequences, the kit comprising one or more cDNA primers and one or more circularization probes. The kits also can contain, for example, reverse transcriptases, DNA polymerases, rolling circle replication primers, DNA strand displacement primers, detection probes, nucleotides, buffers, ligases, or a combination.

V. Mixtures

Disclosed are mixtures formed by performing or preparing to perform the disclosed method. For example, disclosed are mixtures comprising one or more cDNA primers and one or more circularization probes; tandem sequence DNA, one or more cDNA primers and one or more circularization probes; DNA polymerase, one or more cDNA primers and one or more circularization probes; DNA polymerase, tandem sequence DNA, one or more cDNA primers and one or more circularization probes; double-stranded tandem sequence DNA, one or more cDNA primers and one or more circularization probes; tandem sequence DNA, secondary tandem sequence DNA, one or more cDNA primers and one or more circularization probes; DNA polymerase, tandem sequence DNA, secondary tandem sequence DNA, one or more cDNA primers and one or more circularization probes; one or more RNA samples, one or more cDNA primers and one or more circularization probes; tandem sequence DNA, one or more RNA samples, one or more cDNA primers and one or more circularization probes; DNA polymerase, one or more RNA samples, one or more cDNA primers and one or more circularization probes; DNA polymerase, tandem sequence DNA, one or more RNA samples, one or more cDNA primers and one or more circularization probes; double-stranded tandem sequence DNA, one or more RNA samples, one or more cDNA primers and one or more circularization probes; tandem sequence DNA, secondary tandem sequence DNA, one or more RNA samples, one or more cDNA primers and one or more circularization probes; DNA polymerase, tandem sequence DNA, secondary tandem sequence DNA, one or more RNA samples, one or more cDNA primers and one or more circularization probes; one or more tandem repeat units, one or more cDNA primers and one or more circularization probes; tandem sequence DNA, one or more tandem repeat units, one or more cDNA primers and one or more circularization probes; DNA polymerase, one or more tandem repeat units, one or more cDNA primers and one or more circularization probes; DNA polymerase, tandem sequence DNA, one or more tandem repeat units, one or more cDNA primers and one or more circularization probes; double-stranded tandem sequence DNA, one or more tandem repeat units, one or more cDNA primers and one or more circularization probes; and tandem sequence DNA, secondary tandem sequence DNA, one or more tandem repeat units, one or more cDNA primers and one or more circularization probes; DNA polymerase, tandem sequence DNA, secondary tandem sequence DNA, one or more cDNA primers and one or more circularization probes.

Whenever the method involves mixing or bringing into contact compositions or components or reagents, performing the method creates a number of different mixtures. For example, if the method includes 3 mixing steps, after each one of these steps a unique mixture is formed if the steps are performed separately. In addition, a mixture is formed at the completion of all of the steps regardless of how the steps were performed. The present disclosure contemplates these mixtures, obtained by the performance of the disclosed methods as well as mixtures containing any disclosed reagent, composition, or component, for example, disclosed herein.

W. Systems

Disclosed are systems useful for performing, or aiding in the performance of, the disclosed method. Systems generally comprise combinations of articles of manufacture such as structures, machines, devices, and the like, and compositions, compounds, materials, and the like. Such combinations that are disclosed or that are apparent from the disclosure are contemplated. For example, disclosed and contemplated are systems comprising solid supports and cDNA primers, circularization probes, detection probes, address probes, or a combination.

X. Data Structures and Computer Control

Disclosed are data structures used in, generated by, or generated from, the disclosed method. Data structures generally are any form of data, information, and/or objects collected, organized, stored, and/or embodied in a composition or medium. A cDNA library stored in electronic form, such as in RAM or on a storage disk, is a type of data structure.

The disclosed method, or any part thereof or preparation therefor, can be controlled, managed, or otherwise assisted by computer control. Such computer control can be accomplished by a computer controlled process or method, can use and/or generate data structures, and can use a computer program. Such computer control, computer controlled processes, data structures, and computer programs are contemplated and should be understood to be disclosed herein.

Uses

The disclosed method and compositions are applicable to numerous areas including, but not limited to, analysis of nucleic acids present in cells (for example, analysis of RNA in cells), disease detection, mutation detection, gene discovery, gene mapping (molecular haplotyping), and agricultural research. Particularly useful is gene expression profiling. Other uses include, for example, molecular haplotyping; mutation detection; detection of inherited diseases such as cystic fibrosis, muscular dystrophy, diabetes, hemophilia, sickle cell anemia; assessment of predisposition for cancers such as prostate cancer, breast cancer, lung cancer, colon cancer, ovarian cancer, testicular cancer, pancreatic cancer.

Method

Disclosed are methods for amplification of RNA molecules. The disclosed method involves synthesizing first strand cDNA molecules from RNA molecules, circularizing the first strand cDNA molecules and replicating the circularized first strand cDNA molecules using rolling circle replication. The method can be aided by the use of specialized primers for cDNA synthesis, referred to as cDNA primers, and specialized probes for circularizing the first strand cDNA molecules, referred to as circularization probes. The method can be used to replicate and amplify multiple RNA molecules, such as all RNA molecules in a sample or all mRNA molecules in a sample, or can be used to replicate and amplify specific RNA molecules. Rolling circle replication of the circularized first strand cDNA molecules results in long DNA strands containing tandem repeats of the cDNA sequence. Rolling circle replication can be primed from a single location on the circular first stand cDNA molecules or can be primed from multiple sites. Regardless of where priming occurs, the resulting tandem sequence DNA will contain tandem repeats of the full cDNA sequence since synthesis continues multiple times around the circle.

In some forms of the disclosed method, a cDNA primer is used to prime synthesis of a first cDNA strand. The cDNA primer can include an RNA complement portion and a probe complement portion. The RNA complement portion hybridizes to RNA molecules in an RNA sample and primes reverse transcription. The resulting first strand cDNA molecules incorporate the cDNA primer at their 5' ends. The first strand cDNA molecules are circularized using a circularization probe. The circularization probe can include a primer complement portion and a cDNA complement portion. The primer complement portion is complementary to the probe complement portion of the cDNA primer. The cDNA complement portion is hybridizes to sequence in the first strand cDNA molecules. In particular, the cDNA complement portion hybridizes to 3'-end sequence of first strand cDNA molecules. In this way, the ends of first strand cDNA molecules are brought into proximity so they can be ligated together.

The circularized first strand cDNA molecules can then be amplified via rolling circle replication. Rolling circle replication can be primed by a rolling circle replication primer. The rolling circle replication can have a complementary portion, which is complementary to a first strand cDNA molecule. The complementary portion can be complementary to sequence in the cDNA primer, can match sequence in the circularization probe, or both. In this case, the rolling circle replication primer either can be specific for one or some first strand cDNA molecules or can be used to amplify first strand cDNA molecules broadly (depending on whether the primer complement/primer matching sequence in the cDNA primer and/or circularization probe are different (specific) for different first strand cDNA molecules or the same (not specific) for different first strand cDNA molecules. Alternatively, the complementary portion can be complementary to cDNA sequence. In this case, the rolling circle replication primer can be specific for one or a few first strand cDNA molecules. Rolling circle replication primers having random sequence will be complementary to numerous sequences in circular first strand cDNA molecules and can be used to amplify first strand cDNA molecules broadly.

A single cDNA primer and a single circularization probe can be used amplify all RNA molecules in a sample. For example, the cDNA primer can include an RNA complement portion comprised of poly(dT) or random sequence, partially random sequence, and/or nucleotides that can base pair with more than one type of nucleotide. The RNA complement of a cDNA primer will hybridize any RNA sequence to which it is complementary, such as all mRNA (if poly(dT) is used) or all RNA molecules in general (if a generic sequence is used). In this way all of the RNA molecules in a sample can be reverse transcribed. The circularization probe can include, for example, a cDNA complement portion comprised of random sequence, partially random sequence, and/or nucleotides that can base pair with more than one type of nucleotide. The generic nature of the cDNA complement portion allows it to hybridize to any of, or many of, the 3'-end sequences of first strand cDNA molecules. In this way, a circularization probe can be generic for amplification of RNA molecules in an RNA sample.

A single rolling circle replication primer can be used to can be used amplify all RNA molecules in a sample. For example, the rolling circle primer can have a random sequence making it complementary to many sequences in first strand cDNA molecules. Alternatively, the rolling circle replication primer can have a complementary portion that is complementary to sequence in the cDNA primer (that is, the primer complement portion of the cDNA primer), that matches sequence in the circularization probe (that is, the primer matching portion of the circularization probe). As another alternative, the circularization probe can be used as the rolling circle replication primer. In this way, only a single cDNA primer and a single circularization probe would be needed to form circular first strand cDNA molecules and to replicate the circles. The cDNA primer can also serve as a secondary DNA strand displacement primer, thus allowing exponential rolling circle amplification with only these two oligonucleotides.

The tandem sequence DNA also can be made double-stranded. Double-stranded tandem sequence DNA can be used, for example to produce unit lengths of the cDNA sequence making up the tandem sequence DNA. Production of unit length cDNA molecules can be aided by including a cleavage site, such as the recognition site for a restriction enzyme, in the cDNA primer and/or circularization probe. The double-stranded tandem sequence DNA and, especially, the unit lengths of cDNA sequence can be cloned using recombinant DNA techniques and materials. Tandem sequence DNA and tandem sequence DNA fragments, including unit length cDNA molecules, can constitute a cDNA library. Each unit length of cDNA sequence (that is, one of the tandem repeat sequences produced from the circular first strand cDNA molecules) represents the cDNA sequence of an RNA molecule. The unit length of cDNA sequence (or a single tandem repeat sequence) can be referred to as a tandem repeat unit.

The tandem sequence DNA strand produced by rolling circle replication corresponds to the positive strand of the DNA from which the corresponding RNA was replicated. Secondary tandem sequence DNA, which results from replication of tandem sequence DNA, corresponds to the negative strand of the DNA from which the corresponding RNA was replicated. Subsequent generations of tandem sequence DNA strands (for example, tertiary tandem sequence DNA and quaternary tandem sequence DNA) also represent either the positive or negative strand. Either the positive strand (for example, the tandem sequence DNA strand) or the negative strand (for example, the secondary tandem sequence DNA) can be produced in isolation in the disclosed method. This can be accomplished, for example, by synthesizing only the tandem sequence DNA strand or by selectively degrading one of the types of strand.

Tandem sequence DNA can also be transcribed to produce transcripts having sequence complementary to or matching the sequence of RNA molecules. The tandem sequence DNA can be transcribed directly to produce long RNA molecules, referred to as tandem sequence transcripts, made up of tandem repeats of the RNA sequence (or its complement). Unit length cDNA molecules (that is tandem repeat units) can also be transcribed to produce RNA molecules, referred to as tandem repeat transcripts, containing a single RNA sequence (or its complement).

Further amplification of the cDNA sequences can be accomplished using any suitable replication or amplification technique. Useful amplification techniques include rolling circle amplification techniques such as multiply-primed rolling circle amplification and exponential rolling circle amplification. Rolling circle replication and rolling circle amplification of the circularized first strand cDNA molecules can also be combined with multiple strand displacement amplification and other amplification techniques to produce specialized amplification products and/or to further increase the amplification yield.

An example of the disclosed method is shown in FIG. 1. A cDNA primer (SEQ ID NO:3) anneals to the poly(a) region of mRNA molecules (SEQ ID NO:4) (top). The 3' end of the cDNA primer aligns with the junction of the transcribed sequences and the poly(A) in the mRNA molecules due to two degenerate nucleotide positions (Ns) at the 3' end of the cDNA primer. The cDNA primer includes a Not I cleavage site. Reverse transcription produces a linear first strand cDNA molecules. A circularization probe (SEQ ID NO:5) is added and the first strand cDNA molecules are circularized. The circularization probe uses a random sequence (Ns) as the cDNA complement portion, allowing the circularization probe to mediate circularization of any first strand cDNA molecule. The circularization probe includes a Not I cleavage site (in the primer complement portion). Exonuclease-resistant random hexamer primers and ϕ29 DNA polymerase are then used to amplify the circular first strand cDNA molecules via exponential rolling circle amplification. The hexamer primers serve as both rolling circle replication primers and secondary DNA strand displacement primers. Because the hexamer primers hybridize at multiple locations on the first strand cDNA molecules, the amplification is a form of multiply-primer rolling circle amplification. Rolling circle amplification produces double-stranded tandem sequence DNA. The tandem sequence DNA can be cleaved with Not I to produce single tandem repeat units because a Not I site appears between every tandem repeat unit (due to incorporation of the Not I site of the cDNA primer into the first strand cDNA molecule). The tandem repeat units thus produced represent a cDNA library of the mRNA molecules. The tandem repeat units can be used directly or cloned into a vector to produce a traditional cDNA library.

Tandem sequence DNA produced in the disclosed method can be used directly (for detection of sequences, for example), further amplified, cloned, or used any other purpose. Tandem sequence DNA molecules produced in the disclosed method from an RNA sample can contain sequences representing all or a portion of the RNA sequences present in the sample. For example, the disclosed method can be used to produce circular first strand cDNA molecules (and thus, tandem sequence DNA) from all of the RNA molecules in an RNA sample, from all of the mRNA molecules in an RNA sample, or from selected RNA molecules in an RNA sample.

A. cDNA Synthesis

First strand cDNA molecules are produced by reverse transcription of RNA molecules primed by cDNA primers. Reverse transcription can be performed using any known technique. Reverse transcription involves production of a DNA complement to an RNA sequence. Reverse transcription is mediated by reverse transcriptases, which are DNA polymerases that can use RNA as a template for replication. Many reverse transcriptases are RNA-dependent DNA polymerases. Reverse transcription reactions are well known and any suitable conditions can be used for reverse transcription of RNA molecules in the disclosed method. The disclosed method generally involves only first strand cDNA synthesis. For this reason, techniques and manipulations used for second strand cDNA synthesis generally are not applicable to the disclosed method. However, first strand cDNA molecules can be derived from double-stranded cDNA and used in the disclosed method (that is, can be circularized and amplified).

The RNA complement portion of the cDNA primers determines which RNA molecules in an RNA sample will be transcribed. For example, if the RNA complement portion of a cDNA primer has a random sequence or is made up of nucleotides that can base pair with more than one type of nucleotide (such as universal nucleotides or inosine), then the cDNA primer can hybridize to, and prime reverse transcription of, any RNA molecule or sequence. Such a cDNA primer can be referred to as a generic cDNA primer. Sequences that are random sequences, that are made up of nucleotides that can base pair with more than one type of nucleotide, or a combination, can be referred to as generic sequences. Partially random or degenerate sequences can also be used in RNA complement portions of cDNA primers. This results in cDNA primers that generally can prime transcription of multiple RNA molecules and sequences but that will not prime transcription of all RNA molecules.

If the RNA complement portion of a cDNA primer includes poly(dT), then the cDNA primer can hybridize to, and prime reverse transcription of, polyadenylated RNA molecules, such as mRNA. Such cDNA primers can be referred to as poly(A) cDNA primers. Production of first strand cDNA molecules from only polyadenylated RNA molecules in an RNA sample is useful because such RNA molecules are relevant to gene expression and expression profiling. Specific sequences can be used at the 3' end of cDNA primers that include poly(dT) in the RNA complement portion (that is, poly(A) cDNA primers). Doing so results in a cDNA primer that is specific for a certain polyadenylated RNA molecule and will prime transcription from the end of the RNA molecule (making it possible to obtain full length cDNA sequence of the RNA molecule). The combination of a specific sequence and a poly(dT) sequence assures that transcription will be primed at the junction of specific RNA sequence and the poly(A) tail. Further, the specific sequence will specify priming of only those RNA molecules having that sequence at the poly(A) junction.

A similar effect can be achieved for transcription of polyadenylated RNA molecules in general by using random sequence (or nucleotides that can base pair with more than one type of nucleotide) at the 3' end of cDNA primers that include poly(dT) in the RNA complement portion. The cDNA primer will prime transcription from the end of any RNA molecule (making it possible to obtain full length cDNA sequence of the RNA molecule). The combination of a generic sequence and a poly(dT) sequence assures that transcription will be primed at the junction of specific RNA sequence and the poly(A) tail. Because the generic sequence allows the primer to hybridize to any poly(A) junction sequence, the cDNA primer can be used to produce first strand cDNA molecules of polyadenylated RNA in general from the poly(A) junction (and thus potentially full length). Such cDNA primers can be referred to as junction-specific poly(A) cDNA primers.

If the RNA complement portion of a cDNA primer has a specific sequence, then the cDNA primer can hybridize to, and prime reverse transcription of, specific RNA molecules and sequences. Such a cDNA primer can be referred to as a specific cDNA primer. Specific cDNA primers are useful for producing first strand cDNA molecules from specific RNA molecules. It also can be useful to use sets of specific cDNA primers together in order to produce first strand cDNA molecules from a particular set of RNA molecules of interest.

In some embodiments of the disclosed method a plurality of RNA molecules can be reverse transcribed. The plurality of different RNA molecules may comprises a set of RNA molecules derived from, or present in, a source of interest. Such a source can include, for example, cells, tissue or any other source of RNA. The disclosed method may also involve a plurality of different RNA molecules which are associated with a condition or disease state of the cells, tissue, or the source of the RNA sample. In some embodiments of the disclosed method, the plurality of different RNA molecules comprises a set of RNA molecules representing a catalog of RNA molecules from a source of interest. The disclosed method also may include a plurality of different RNA molecules comprising a set of RNA molecules from one or more of sources of interest. The RNA molecules used in the method can be present in an RNA sample.

B. Circularization Operation

First strand cDNA molecules are circularized using circularization probes. The circularization probe can include a primer complement portion and a cDNA complement portion. The primer complement portion is complementary to the probe complement portion of the cDNA primer. The cDNA complement portion is hybridizes to sequence in the first strand cDNA molecules. In particular, the cDNA complement portion hybridizes to 3' end sequence of first strand cDNA molecules. In this way, the ends of first strand cDNA molecules are brought into proximity so they can be ligated together. The ends can be brought together in any conformation for coupling or ligation. It is particularly useful if the ends of the first strand cDNA molecule each hybridize to a circularization probe such that the 5' and 3' terminal nucleotides of the first strand cDNA molecule are base paired to immediately adjacent nucleotides in the circularizartion probe.

The ends of linear first strand cDNA molecules can be joined or coupled in any manner that produces a cDNA molecule that can be replicated and amplified. Generally this will involve formation of a phosphodiester bond between the end nucleotides. Such a bond can be produced in any suitable manner, such as enzymatically with a ligase. Ligation reactions are well known and any suitable conditions can be used for ligation of first strand cDNA molecules in the disclosed method. The ends can also be joined or coupled via non-phosphate linkages and bonds so long as the resulting cDNA molecule can serve as a template for replication.

The cDNA complement portion of the circularization probes determines which first strand cDNA molecules will be circularized. For example, if the cDNA complement portion of a circularization probe has a random sequence or is made up of nucleotides that can base pair with more than one type of nucleotide (such as universal nucleotides or inosine), then the circularization probe can hybridize to, and mediate circularization of, any first strand cDNA molecule. Such a circularization probe can be referred to as a generic circularization probe. Partially random or degenerate sequences can also be used in cDNA complement portions of circularization probes. This results in circularization probes that generally can mediate circularization of multiple first strand cDNA molecules and sequences but that will not mediate circularization of all first strand cDNA molecules. This effect can be used to limit the first strand cDNA molecules for which a circularization probe can mediate circularization.

If the cDNA complement portion of a circularization probe has a specific sequence, then the circularization probe can hybridize to, and mediate circularization of, specific first strand cDNA molecules. Such a circularization probe can be referred to as a specific circularization probe. Specific circularization probes are useful for circularizing specific first strand cDNA molecules or specific forms of first strand cDNA molecules. It also can be useful to use sets of specific circularization probes together in order to produce circular first strand cDNA molecules from a particular set of linear first strand cDNA molecules of interest. This can be useful, for example, to favor circularization of full length first strand cDNA molecules of particular RNA molecules or circularization of first strand cDNA molecules having a particular 3' end sequence.

Although circularization of first strand cDNA molecules is a goal of most forms of the disclosed method, first strand cDNA molecules can also be manipulated in other ways. In some forms of the disclosed method, first strand cDNA molecules can be ligated together to form concatemers. Circularization probes can mediate such concatemerization, for example, when the primer complement portion of the circularization probe hybridizes to the probe complement portion of one first strand cDNA molecule and the cDNA complement portion of the circularization probe hybridizes to a cDNA sequence of a different first strand cDNA molecule. The circularization operation of the disclosed method, depending on the conditions used, can result in production of one or a combination of the four types of first strand cDNA products: circular first strand cDNA molecules, circular first strand cDNA concatemers, uncircularized first strand cDNA molecules, and uncircularized first strand cDNA concatemers.

First strand cDNA concatemers can be amplified via multiple strand displacement amplification (and/or any other suitable amplification technique). First strand cDNA concatemers that are circularized can be amplified via rolling circle replication. Rolling circle replication of circular first strand cDNA molecules and/or first strand cDNA concatemers can be carried out simultaneously with multiple strand displacement amplification of uncircularized first strand cDNA molecules and/or uncircularized first strand cDNA concatemers. In most forms of the disclosed method, uncircularized first strand cDNA molecules will not be amplified or will not be effectively amplified.

C. Amplification Operation

The basic form of amplification operation in the disclosed method is rolling circle replication of a circular first strand DNA molecule. Rolling circle amplification generally requires use of one or more rolling circle replication primers, which are complementary to the primer complement portions of the first strand cDNA molecules, and a rolling circle DNA polymerase. The DNA polymerase catalyzes primer extension and strand displacement in a processive rolling circle polymerization reaction that proceeds as long as desired, generating a large DNA molecule that contains a large number of tandem copies of a sequence complementary to the first strand cDNA molecule. Some forms of the disclosed method use rolling circle replication primers and secondary DNA strand displacement primers in the amplification reaction.

In multiply-primed RCA, one or more rolling circle replication primers anneal at various places on a first strand cDNA molecule to generate multiple replication forks. As each strand grows, the DNA polymerase encounters an adjacent replicating strand and displaces it from the first strand cDNA molecule. The result is multiple copies of each first strand cDNA molecule being produced simultaneously. Multiply-primed RCA can be performed using a single primer (which hybridizes to multiple sites on the first strand cDNA molecule) or multiple primers (each of which can hybridize to a single site on the first strand cDNA molecule or multiple sites on the first strand cDNA molecule). Multiple priming (as occurs in MPRCA) can increase the yield of amplified product from RCA. Primers anneal to multiple locations on the circular template and a product of extension by polymerase is initiated from each location. In this way, multiple extensions are achieved simultaneously from a single first strand cDNA molecule.

As well as rolling circle replication, the amplification operation can include additional nucleic acid replication or amplification processes. For example, TS-DNA can itself be replicated to form secondary TS-DNA. This process is referred to as secondary DNA strand displacement. The combination of rolling circle replication and secondary DNA strand displacement is a form of linear rolling circle amplification (LRCA). The result is double-stranded tandem sequence DNA. Double-stranded tandem sequence DNA can be used for any purpose, including, for example, detection of sequences, sequencing, cloning, and formation of cDNA libraries.

Secondary TS-DNA can itself be replicated to form tertiary TS-DNA in a process referred to as tertiary DNA strand displacement. Secondary and tertiary DNA strand displacement can be performed sequentially or simultaneously. When performed simultaneously, the result is strand displacement cascade amplification. The combination of rolling circle replication and strand displacement cascade amplification is referred to as exponential rolling circle amplification (ERCA). Secondary TS-DNA, tertiary TS-DNA, or both can be amplified by transcription. Exponential rolling circle amplification is a preferred form of amplification operation.

For amplification of linear first strand cDNA concatemers, multiple strand displacement amplification can be used. Multiple strand displacement amplification involves hybridization of primers to a first strand cDNA molecule and replication of the first strand cDNA molecule primed by the hybridized primers. During replication, the growing replicated strands displace other replicated strands from the first strand cDNA molecule (or from another replicated strand) via strand displacement replication. As used herein, a replicated strand is a nucleic acid strand resulting from elongation of a primer hybridized to a first strand cDNA molecule or to another replicated strand. Strand displacement replication refers to DNA replication where a growing end of a replicated strand encounters and displaces another strand from the template strand (or from another replicated strand). Displacement of replicated strands by other replicated strands is a hallmark of multiple strand displacement amplification.

The tandem sequence DNA produced in the disclosed method can be used for any purpose. Useful purposes include, for example, detecting specific RNA molecules and/or sequences; detecting a population or set of RNA molecules and/or sequences; analyzing or sequencing specific RNA molecules and/or sequences; analyzing or sequencing a population or set of RNA molecules and/or sequences; cataloging a population or set of RNA molecules and/or sequences; using tandem sequence DNA as probes, markers, hybridization probes, primers, or a combination; cloning specific RNA molecules and/or sequences; and cloning a population or set of RNA molecules and/or sequences. Thus, for example, the tandem sequence DNA produced in the disclosed method can be used to identify or analyze the RNA molecules and/or sequences expressed in different cells, tissues, and/or samples, and compare the RNA molecules and/or sequences expressed in different cells, tissues, and/or samples. The tandem sequence DNA can be used in a hybridization assay.

1. Rolling Circle Amplification

The disclosed method involves rolling circle amplification. Rolling circle amplification refers to nucleic acid amplification reactions where a circular nucleic acid template (here, circular first strand cDNA molecules) is replicated in a single long strand with tandem repeats of the sequence of the circular template. This first, directly produced tandem repeat strand is referred to as tandem sequence DNA (TS-DNA) and its production is referred to as rolling circle replication. In the disclosed method, this tandem sequence DNA contains sequence matching sequence in the source RNA molecule. The tandem sequence DNA thus corresponds to the positive strand (analogous to the positive strand of the DNA sequence from which the source RNA molecule was transcribed). Rolling circle amplification refers both to rolling circle replication and to processes involving both rolling circle replication and additional forms of amplification. For example, tandem sequence DNA can be replicated to form complementary strands referred to as secondary tandem sequence DNA. Secondary tandem sequence DNA can, in turn, be replicated, and so on. Tandem sequence DNA can also be transcribed. Rolling circle amplification involving production of only the first tandem sequence DNA (that is, the replicated strand produced by rolling circle replication) can be referred to as of linear rolling circle amplification (where "linear" refers to the general amplification kinetics of the amplification). Production of only the first tandem sequence DNA can also be referred to as positive strand amplification since it results in a positive strand cDNA molecule (the tandem sequence DNA).

When rolling circle amplification is involved, the rolling circle replication primer and the circular template must be associated together. This typically can occur through mixing one or more circular first strand cDNA molecules with the rolling circle replication primers under conditions that promote association of the rolling circle replication primers with the first strand cDNA molecules. To get replication of the first strand cDNA molecules the first strand cDNA molecule and the rolling circle replication primer typically are incubated under conditions that promote replication of the first strand cDNA molecules, wherein replication of the first strand cDNA molecules results in the formation of tandem sequence DNA. There are numerous variations of rolling circle amplification that can be used in the disclosed methods. Some useful variations of rolling circle amplification are described in, for example, U.S. Pat. No. 5,563,912, U.S. Pat. No. 6,143,495, and U.S. Pat. No. 6,316,229. In some embodiments the tandem sequence DNA can itself be replicated or otherwise amplified.

2. DNA Strand Displacement

DNA strand displacement is one way to amplify TS-DNA. Secondary DNA strand displacement is accomplished by hybridizing secondary DNA strand displacement primers to TS-DNA and allowing a DNA polymerase to synthesize DNA from these primed sites (see FIG. 11 in U.S. Pat. No. 6,143,495). Because a complement of the secondary DNA strand displacement primer occurs in each repeat of the TS-DNA, secondary DNA strand displacement can result in a high level of amplification. The product of secondary DNA strand displacement is referred to as secondary tandem sequence DNA or TS-DNA-2. Secondary DNA strand displacement can be accomplished by performing RCA to produce TS-DNA, mixing secondary DNA strand displacement primer with the TS-DNA, and incubating under conditions promoting replication of the tandem sequence DNA.

Secondary DNA strand displacement can also be carried out simultaneously with rolling circle replication. This is accomplished by mixing secondary DNA strand displacement primer with the reaction prior to rolling circle replication. As a secondary DNA strand displacement primer is elongated, the DNA polymerase will run into the 5' end of the next hybridized secondary DNA strand displacement molecule and will displace its 5' end. In this fashion a tandem queue of elongating DNA polymerases is formed on the TS-DNA template. As long as the rolling circle reaction continues, new secondary DNA strand displacement primers and new DNA polymerases are added to TS-DNA at the growing end of the rolling circle. The generation of TS-DNA-2 and its release into solution by strand displacement is shown diagrammatically in FIG. 11 in U.S. Pat. No. 6,143,495. For simultaneous rolling circle replication and secondary DNA strand displacement, it is preferred that the rolling circle DNA polymerase be used for both replications. This allows optimum conditions to be used and results in displacement of other strands being synthesized downstream.

Generally, secondary DNA strand displacement can be performed by, simultaneous with or following RCA, mixing a secondary DNA strand displacement primer with the reaction mixture and incubating under conditions that promote both hybridization between the tandem sequence DNA and the secondary DNA strand displacement primer, and replication of the tandem sequence DNA, where replication of the tandem sequence DNA results in the formation of secondary tandem sequence DNA.

When secondary DNA strand displacement is carried out in the presence of a tertiary DNA strand displacement primer (or an equivalent primer), an exponential amplification of TS-DNA sequences takes place. This special mode of DNA strand displacement is referred to as strand displacement cascade amplification (SDCA) and is a form of exponential rolling circle amplification (ERCA). In SDCA, a secondary DNA strand displacement primer primes replication of TS-DNA to form TS-DNA-2, as described above. The tertiary DNA strand displacement primer strand can then hybridize to, and prime replication of, TS-DNA-2 to form TS-DNA-3. Strand displacement of TS-DNA-3 by the adjacent, growing TS-DNA-3 strands makes TS-DNA-3 available for hybridization with secondary DNA strand displacement primer. This results in another round of replication resulting in TS-DNA-4 (which is equivalent to TS-DNA-2). TS-DNA-4, in turn, becomes a template for DNA replication primed by tertiary DNA strand displacement primer. The cascade continues this manner until the reaction stops or reagents become limiting. This reaction amplifies DNA at an almost exponential rate. In a useful mode of SDCA, the rolling circle replication primers serve as the tertiary DNA strand displacement primer, thus eliminating the need for a separate primer. The additional forms of tandem sequence DNA beyond secondary tandem sequence DNA are collectively referred to herein as higher order tandem sequence DNA. Higher order tandem sequence DNA encompasses TS-DNA-3, TS-DNA-4, and any other tandem sequence DNA produced from replication of secondary tandem sequence DNA or the products of such replication.

For this mode, the rolling circle replication primer should be used at a concentration sufficiently high to obtain rapid priming on the growing TS-DNA-2 strands. To optimize the efficiency of SDCA, it is preferred that a sufficient concentration of secondary DNA strand displacement primer and tertiary DNA strand displacement primer be used to obtain sufficiently rapid priming of the growing TS-DNA strand to out compete TS-DNA for binding to its complementary TS-DNA. Optimization of primer concentrations are described in U.S. Pat. No. 6,143,495 and can be aided by analysis of hybridization kinetics (Young and Anderson, "Quantitative analysis of solution hybridization" in *Nucleic Acid Hybridization: A Practical Approach* (IRL Press, 1985) pages 47–71).

Generally, strand displacement cascade amplification can be performed by, simultaneous with, or following, RCA, mixing a secondary DNA strand displacement primer and a tertiary DNA strand displacement primer with the reaction mixture and incubating under conditions that promote hybridization between the tandem sequence DNA and the secondary DNA strand displacement primer, replication of the tandem sequence DNA—where replication of the tandem sequence DNA results in the formation of secondary tandem sequence DNA—hybridization between the secondary tandem sequence DNA and the tertiary DNA strand displacement primer, and replication of secondary tandem sequence DNA—where replication of the secondary tandem sequence DNA results in formation of tertiary tandem sequence DNA (TS-DNA-3).

Secondary and tertiary DNA strand displacement can also be carried out sequentially. Following a first round of secondary DNA strand displacement, a tertiary DNA strand displacement primer can be mixed with the secondary tandem sequence DNA and incubated under conditions that promote hybridization between the secondary tandem sequence DNA and the tertiary DNA strand displacement primer, and replication of secondary tandem sequence DNA, where replication of the secondary tandem sequence DNA results in formation of tertiary tandem sequence DNA (TS-DNA-3). This round of strand displacement replication can be referred to as tertiary DNA strand displacement. However, all rounds of strand displacement replication following rolling circle replication can also be referred to collectively as DNA strand displacement or secondary DNA strand displacement.

A modified form of secondary DNA strand displacement results in amplification of TS-DNA and is referred to as opposite strand amplification (OSA). OSA is the same as secondary DNA strand displacement except that a special form of rolling circle replication primer is used that prevents it from hybridizing to TS-DNA-2. Opposite strand amplification is described in U.S. Pat. No. 6,143,495.

The DNA generated by DNA strand displacement can be labeled and/or detected using the same labels, labeling methods, and detection methods described for use with TS-DNA. In the disclosed method, detection generally will be during DNA strand displacement and preferably is accomplished through the use of fluorescent changes probes and/or primers. For example, secondary DNA strand displacement primers and/or tertiary DNA strand displacement primers can be fluorescent change primers. Alternatively or in addition, detection probes that are fluorescent change probes can be used.

By using rolling circle replication primers and secondary DNA strand displacement primers where one has a 5' phosphate and the other has a 5' hydroxyl, a single type of cDNA strand, positive or negative, can be produced from DNA strand displacement. Odd generation tandem sequence DNA (for example, TS-DNA-1, TS-DNA-3, TS-DNA-5) has sequence matching sequence in the source RNA molecule for the template first strand cDNA molecule. These all correspond to positive strand cDNA molecules. Even generation tandem sequence DNA (for example, TS-DNA-2, TS-DNA-4, TS-DNA-6) has sequence complementary to sequence in the source RNA molecule for the template first strand cDNA molecule. These all correspond to negative strand cDNA molecules. By selectively degrading one type of tandem sequence DNA, all positive strand or all negative strand amplification product can be obtained.

This selective degradation can be accomplished, for example, by using rolling circle replication primers and secondary DNA strand displacement primers where one has a 5' phosphate and the other has a 5' hydroxyl and then digesting the tandem sequence DNA with a phosphate-dependent exonuclease. Only tandem sequence DNA strands primed by the 5' phosphate-contain primers will be degraded. Thus, if rolling circle replication primers having 5' phosphates are used with secondary DNA strand displacement primer having 5' hydroxyls, only even generation tandem sequence DNA strands will be degraded, leaving negative strand cDNA (that is, the odd generation tandem sequence DNA strands). Similarly, if rolling circle replication primers having 5' hydroxyls are used with secondary DNA strand displacement primer having 5' phosphates, only odd generation tandem sequence DNA strands will be degraded, leaving positive strand cDNA (that is, the even generation tandem sequence DNA strands). If tertiary DNA strand displacement primers are used, they should have the same phosphorlated/unphosphorylated state as the rolling circle replication primers. Similarly, if cDNA primers and/or circularization probes are used as secondary DNA strand displacement primers or rolling circle replication primers, respectively, they should have the same phosphorlated/unphosphorylated state as the respective primers (that is, the same phosphorlated/unphosphorylated state as the secondary DNA strand displacement primers or rolling circle replication primers, respectively) to have the same effect.

3. Geometric Rolling Circle Amplification

RCA reactions can be carried out with either linear or geometric kinetics (Lizardi et al., 1998). Linear rolling circle amplification generally follows linear kinetics. Two useful forms of RCA with geometric kinetics are exponential multiply-primed rolling circle amplification (EMPRCA) and exponential rolling circle amplification (ERCA). In exponential multiply-primed RCA, one or more rolling circle replication primers anneal at various places on the circular first strand cDNA molecule to generate multiple replication forks. As each strand grows, the DNA polymerase encounters an adjacent replicating strand and displaces it from the first strand cDNA molecule. The result is multiple copies of each first strand cDNA molecule being produced simultaneously. The replicated strands are referred to as tandem sequence DNA (TS-DNA). As each TS-DNA strand is displaced from the circular template, secondary DNA strand displacement primers can anneal to, and prime replication of, the TS-DNA. Replication of the TS-DNA forms complementary strands referred to as secondary tandem sequence DNA or TS-DNA-2. As a secondary TS-DNA strand is elongated, the DNA polymerase will run into the 5' end of the next growing strand of secondary TS-DNA and will displace its 5' end. In this fashion a tandem queue of elongating DNA polymerases is formed on the TS-DNA template. As long as the rolling circle reaction continues, new primers and new DNA polymerases are added to TS-DNA at the growing end of the rolling circle.

Random or degenerate primers can be used to perform multiply-primed RCA. Such random or degenerate primers will anneal to multiple sites on the first strand cDNA molecule (resulting in production of tandem sequence DNA), as well as to multiple sites on the tandem sequence DNA (resulting in production of secondary tandem sequence DNA). The random primers can then hybridize to, and prime replication of, TS-DNA-2 to form TS-DNA-3 (which is equivalent to the original TS-DNA). Strand displacement of TS-DNA-3 by the adjacent, growing TS-DNA-3 strands makes TS-DNA-3 available for hybridization with the primers. This can result in another round of replication resulting in TS-DNA-4 (which is equivalent to TS-DNA-2). TS-DNA-4, in turn, becomes a template for DNA replication primed by random primers. The cascade continues this manner until the reaction stops or reagents become limiting. Multiply-primed RCA is particularly useful for amplifying the larger circular templates such as first strand cDNA molecules that are produced in the disclosed method. Multiply-primed RCA is described in Dean et al., Rapid Amplification of Plasmid and Phage DNA Using Phi29 DNA Polymerase and Multiply-Primed Rolling Circle Amplification, Genome Research 11:1095–1099(2001).

Exponential multiply-primed RCA also can be achieved using specific rolling circle replication primers, secondary DNA strand displacement primers and tertiary DNA strand displacement primers. In this form of the disclosed method, rolling circle replication is primed from multiple specific primer complement portions of the circular first strand cDNA molecule. As the strand grows, the DNA polymerase encounters 5' end of the strand and displaces it from the first strand cDNA molecule. A secondary DNA strand displacement primer primes replication of TS-DNA to form a complementary strand referred to as secondary tandem sequence DNA or TS-DNA-2. As a secondary DNA strand displacement primer is elongated, the DNA polymerase will run into the 5' end of the next hybridized secondary DNA strand displacement molecule and will displace its 5', end. In this fashion a tandem queue of elongating DNA polymerases is formed on the TS-DNA template. As long as the rolling circle reaction continues, new secondary DNA strand displacement primers and new DNA polymerases are added to TS-DNA at the growing end of the rolling circle. A tertiary DNA strand displacement primer strand (which is complementary to the TS-DNA-2 strand and which can be the rolling circle replication primer) can then hybridize to, and prime replication of, TS-DNA-2 to form TS-DNA-3 (which is equivalent to the original TS-DNA). Strand displacement of TS-DNA-3 by the adjacent, growing TS-DNA-3 strands makes TS-DNA-3 available for hybridization with secondary DNA strand displacement primer. This results in another round of replication resulting in TS-DNA-4 (which is equivalent to TS-DNA-2). TS-DNA-4, in turn, becomes a template for DNA replication primed by tertiary DNA strand displacement primer. The cascade continues this manner until the reaction stops or reagents become limiting. In one mode of ERCA, the rolling circle replication primer serves as the tertiary DNA strand displacement primer, thus eliminating the need for a separate primer. Circularization probes can be used rolling circle replication primers (and as tertiary DNA strand displacement primers). cDNA primers can be used as secondary DNA strand displacement primers. In this way first strand cDNA production and ERCA can be accomplished with a single pair of primers. Exponential RCA and other useful forms of RCA are described in U.S. Pat. No. 5,854,033, and U.S. Pat. No. 6,143,495.

4. Multiple Strand Displacement Amplification

In another form of the method, multiple strand displacement amplification can be used to amplify first strand cDNA molecules. Generally, multiple strand displacement amplification can be used to amplify first strand cDNA concatemers (including both linear and circular first strand cDNA concatemers). Multiple strand displacement amplification is particularly useful for amplifying concatemers when the primers used are complementary to (or match, as appropriate) primer sequence in the first strand cDNA concatemers. This is because primer complements will be distributed at intervals throughout the concatemer. For this purpose, cDNA primers and/or circularization probes can be used as primers for multiple displacement amplification of first strand cDNA concatemers. Because first strand cDNA concatemers have sequences and components corresponding to first strand cDNA molecules in general, all of the primers useful for amplification of first strand cDNA molecules can be used for amplification in general of first strand cDNA concatemers and multiple strand displacement amplification in particular of first strand cDNA concatemers.

First strand cDNA concatemers can be amplified using a random or partially random set of primers or using specific primers complementary to specific hybridization targets in the first strand cDNA concatemers. Multiple strand displacement amplification of first strand cDNA concatemers provides a means for amplifying all cDNAs in a cell is equal fashion. Because the concatenated cDNA can be amplified up to 5,000-fold, multiple strand displacement amplification permits RNA profiling analysis based on just a few cells. Tandem sequence DNA produced in rolling circle amplification can also be amplified using multiple strand displacement amplification.

D. Double-Stranded Tandem Sequence DNA and Tandem Repeat Units

The tandem sequence DNA also can be made double-stranded. Double-stranded tandem sequence DNA is made up of hybrids of tandem sequence DNA and secondary tandem sequence DNA (or hybrids between other compatible generations of tandem sequence DNA). Double-stranded tandem sequence DNA can be used, for example to produce unit lengths of the cDNA sequence making up the tandem sequence DNA. As discussed elsewhere herein, tandem sequence DNA is made up of multiple tandem repeats of the same sequence representing, or corresponding to, the sequence of a circular first strand cDNA molecule. A single instance of this repeat sequence can be referred to as a single tandem repeat unit (or, more simply, a tandem repeat unit). A tandem repeat unit includes primer sequence (derived from the cDNA primer) and cDNA sequence (derived from the source RNA molecule). A single tandem repeat unit has cDNA sequence derived from a single RNA molecule, the same as a traditional cDNA molecule. Thus, production of tandem repeat units is a useful way to produce amplified analogs of traditional cDNA molecules.

Where the tandem sequence DNA is produced from circular first strand cDNA concatemers, the tandem sequence DNA is made up of multiple mixed tandem repeats of sequence representing, or corresponding to, the sequence of a circular first strand cDNA molecule. That is, the tandem sequence DNA will include different repeat units because the template circle (the first strand cDNA concatemer) includes multiple different cDNA sequences interspersed with primer sequences. A single instance of one of the repeat sequences can be referred to as a single tandem repeat unit (or, more simply, a tandem repeat unit). A tandem repeat unit includes primer sequence (derived from the cDNA primer) and cDNA sequence (derived from the source RNA molecule). A single tandem repeat unit has cDNA sequence derived from a single RNA molecule, the same as a traditional cDNA molecule. Thus, production of tandem repeat units is a useful way to produce amplified analogs of traditional cDNA molecules.

Production of unit length cDNA molecules (that is, tandem repeat units) can be aided by including a cleavage site, such as the recognition site for a restriction enzyme, in the cDNA primer and/or circularization probe. Because the cDNA sequence in tandem sequence DNA can include a variety of sequences (including up to sequence corresponding to all of the RNA sequences in an RNA sample, the cDNA sequence may include a variety of cleavage sites. In order to favor production of tandem repeat units upon cleaving tandem sequence DNA, it is useful to use cleavage sites that occur only rarely, on average, in nucleic acid sequences. In general, the longer the recognition sequence of a cleavage site, the less often the recognition sequence occurs. Put another way, longer recognition sequences generally occur at longer intervals. By using a cleavage site (and cognate restriction endonuclease) having a longer recognition sequence, the number cDNA sequences containing that recognition sequence can be kept to a minimum. As a result, digestion of the tandem sequence DNA will produce the highest yield of single tandem repeat units.

Use of recognition sequences that will occur, on average, only at intervals longer than the average length of cDNA sequence in the first strand cDNA molecules are particularly useful. Thus, for example, an eight nucleotide recognition sequence will occur only once every 65,536 nucleotides, on average. A seven nucleotide recognition sequence will occur only once every 16,384 nucleotides, on average. These intervals are much longer than typical (or even long) transcript length. The average interval at which a given recognition sequence (or any specific sequence) will occur can be calculated with the well known formula $D=4^N$, where N is the length of the sequence and D is the average distance between occurrences of the sequence. The distance is only an approximation based on an even distribution of sites and target sequences having a random sequence. Restriction endonucleases having eight nucleotide recognition sequences include Not I, Asc I, AsiS I, Fse I, Pac I, Pme I, Sbf I, Sfi I, and Swa I. Thus, use of cleavage sites for these restriction endonucleases is preferred. Restriction endonucleases and their use are well known.

The double-stranded tandem sequence DNA and, especially, the unit lengths of cDNA sequence can be cloned using recombinant DNA techniques and materials. Fragments or portions of tandem sequence DNA that is cleaved, digested, or otherwise fragmented can be referred to as tandem sequence DNA fragments. Useful tandem sequence DNA fragments are those produced by cleavage of tandem sequence DNA at cleavage sites. A tandem sequence DNA fragment can include multiple tandem repeat units, a single tandem repeat unit, or a partial tandem repeat unit. The latter, partial tandem repeat units, are not preferred. When tandem sequence DNA is digested to form tandem sequence DNA fragments, the cleavage can result in, for example, at least one of the tandem sequence DNA fragments being a single tandem repeat unit, a plurality of the tandem sequence DNA fragments being single tandem repeat units, a majority of the tandem sequence DNA fragments being single tandem repeat units, or substantially all of the tandem sequence DNA fragments being single tandem repeat units. As used in this context, substantially all refers to greater than 90% of the tandem sequence DNA fragments being single tandem repeat units.

Circular first strand cDNA molecules, and tandem sequence DNA produced from them, are derived from linear first strand cDNA molecules. The linear first strand cDNA molecules are made up of primer sequence (derived from the incorporated cDNA primer) and cDNA sequence (derived from the reverse transcribed RNA). The primer sequence is at the 5' end of the linear first strand cDNA molecules. To make tandem sequence DNA fragments, including tandem repeat units, tandem sequence DNA can be cleaved anywhere in the primer sequences and/or cDNA sequences. By cleaving tandem sequence DNA (and producing tandem repeat units) at a site other than in the primer sequences, the resulting tandem repeat units will have different 5' end sequences than the source linear first strand cDNA molecule. Such a tandem repeat unit is a circular permutation of the linear first strand cDNA molecule. On the other hand, if the tandem sequence DNA is cleaved at a site in the primer sequences, the resulting tandem repeat units will have the same (or nearly the same) 5' end sequences as the source linear first strand cDNA molecule (that is, primer sequence will be at the 5' end of the tandem repeat unit). Such a tandem repeat unit is considered not to be a circular permutation of the linear first strand cDNA molecule. Strictly speaking, a true circular permutation is any tandem repeat unit having a different 5' end from the source linear first strand cDNA molecule by even a single nucleotide. Such true circular permutations are referred to herein as true circular permutations. However, for the purpose of the disclosed method, and as used herein, a tandem repeat unit is referred to as being a circular permutation of a first strand cDNA molecule (as opposed to a true circular permutation) only when cDNA sequence is at the 5' end of the tandem repeat unit. Tandem repeat units that are not circular permutations are preferred.

Circular first strand cDNA molecules, and tandem sequence DNA produced from them, are derived from linear first strand cDNA molecules, which are themselves derived from RNA molecules. When a particular linear or circular first strand cDNA molecule was synthesized from an RNA molecule, the linear or circular first strand cDNA molecule can be said to correspond to that RNA molecule. Similarly, the RNA molecule can be said to correspond to that linear or circular first strand cDNA molecule. When a particular circular first strand cDNA molecule was produced from a linear first strand cDNA molecule, the circular first strand cDNA molecule can be said to correspond to that linear first strand cDNA molecule. Similarly, the linear first strand cDNA molecule can be said to correspond to that circular first strand cDNA molecule. Analogous relationships exist between linear first strand cDNA molecules and first strand cDNA concatemers, both linear and circular.

When a particular tandem sequence DNA molecule was synthesized from a first strand cDNA molecule, the tandem sequence DNA molecule can be said to correspond to that first strand cDNA molecule. Similarly, the first strand cDNA molecule can be said to correspond to that tandem sequence DNA molecule. When a particular tandem sequence DNA fragment was produced from a tandem sequence DNA molecule, the tandem sequence DNA fragment can be said to correspond to that tandem sequence DNA molecule. Similarly, the tandem sequence DNA molecule can be said to correspond to that tandem sequence DNA fragment. When a particular tandem repeat unit was produced from a tandem sequence DNA molecule, the tandem repeat unit can be said to correspond to that tandem sequence DNA molecule. Similarly, the tandem sequence DNA molecule can be said to correspond to that tandem repeat unit.

These relationships also extend through the components of the method. Thus, for example, a tandem repeat unit that corresponds to a tandem sequence DNA molecule also corresponds to the first strand cDNA molecule, linear or circular, to which the tandem sequence DNA molecule corresponds. Similarly, the tandem repeat unit also corresponds to the RNA molecule to which the first strand cDNA molecule, linear or circular, corresponds. A tandem sequence DNA fragment that corresponds to a tandem sequence DNA molecule also corresponds to the first strand cDNA molecule, linear or circular, to which the tandem sequence DNA molecule corresponds. Similarly, the tandem sequence DNA fragment also corresponds to the RNA molecule to which the first strand cDNA molecule, linear or circular, corresponds. A tandem sequence DNA molecule that corresponds to a circular first strand cDNA molecule also corresponds to the linear first strand cDNA molecule to which the circular first strand cDNA molecule corresponds. Similarly, the tandem sequence DNA molecule also corresponds to the RNA molecule to which the first strand cDNA molecule, linear or circular, corresponds.

Tandem sequence DNA fragments can be used for any purpose. For example, tandem sequence DNA fragments can be cloned or otherwise inserted into vectors. Tandem sequence DNA, whether in the form of fragments, tandem repeat units, cloned inserted into vectors, or harbored by viruses or microorganisms, can constitute cDNA libraries.

Prior to use, it can be useful to separate tandem sequence DNA fragments based on size or sequence. For example, it can be useful to select tandem repeat units that are larger than some minimum size, smaller than some maximum size, or both. This can be useful, for example, for eliminating or reducing the number of incomplete (that is, less than full length) cDNA. Exclusion of larger tandem sequence DNA fragments can eliminate or reduce the number of tandem sequence DNA fragments containing multiple tandem repeat units. The selected size or sizes of tandem sequence DNA fragments can be referred to as sizes of interest. Size selection of tandem sequence DNA fragments can also be used in any manner and for any purpose size selection is used for traditional cDNA fragments. Techniques for size selection of nucleic acid molecules are well known and any such technique can be used with the disclosed method and compositions.

Sequence selection of tandem sequence DNA fragments, including tandem repeat units, can be useful for selecting particular cDNA molecules or classes of cDNA molecules derived from particular RNA molecules or classes of RNA molecules. Tandem sequence DNA fragments can be separated or identified based on sequence by using, for example, address probes associated with a solid-state substrate. Particularly useful is the use of arrays of address probes that can, for example, sort and separate tandem sequence DNA fragments, including tandem repeat units, based on sequence and thus catalog the cDNAs present (and thus catalog the source RNA molecules that were present in the RNA sample.

The tandem sequence DNA fragments produced in the disclosed method can be used for any purpose. Useful purposes include, for example, detecting specific RNA molecules and/or sequences; detecting a population or set of RNA molecules and/or sequences; analyzing or sequencing specific RNA molecules and/or sequences; analyzing or sequencing a population or set of RNA molecules and/or sequences; cataloging a population or set of RNA molecules and/or sequences; using tandem sequence DNA fragments, tandem repeat units, or a combination, as probes, markers, hybridization probes, primers, or a combination; cloning specific RNA molecules and/or sequences; and cloning a population or set of RNA molecules and/or sequences. Thus, for example, the tandem sequence DNA fragments produced in the disclosed method can be used to identify or analyze the RNA molecules and/or sequences expressed in different cells, tissues, and/or samples, and compare the RNA molecules and/or sequences expressed in different cells, tissues, and/or samples. The tandem sequence DNA fragments can be used in a hybridization assay.

As used herein, cloning can involve any replication or duplication of the nucleic acid involved (for example, tandem sequence DNA, tandem sequence DNA molecules, tandem sequence DNA fragments, tandem repeat units), including in vitro replication and duplication methods. However, cloning more specifically involves replication and copying of nucleic acids in an organism, often by first inserting the nucleic acid into a vector, such as plasmids. Vectors having inserted nucleic acid can be referred to as recombinant vectors. This can be referred to as conventional cloning. Cloning and cloning techniques are well known.

E. Transcription

Once TS-DNA is generated using RCA, transcripts of the cDNA can be produced. For tandem sequence DNA, long transcripts made up of tandem repeats can be produced. Such transcripts can be referred to as tandem sequence transcripts or as tandem sequence RNA. If the tandem sequence DNA is digested or cleaved to form tandem repeat units, then transcripts of individual cDNAs derived from individual RNA molecules can be produced. Transcripts of single tandem repeat units can be referred to as tandem repeat transcripts. Both tandem sequence transcripts and tandem repeat transcripts are a form of cRNA.

Tandem sequence transcripts can be produced by transcribing the TS-DNA from promoters embedded in the TS-DNA. When transcription of tandem sequence DNA is combined with rolling circle amplification, the combined process can be referred to as rolling circle replication with transcription (RCT) RCT or other production of tandem sequence transcripts and/or tandem repeat transcripts generally requires that the first strand cDNA molecule from which the TS-DNA is made have a promoter portion. The promoter portion is then amplified along with the rest of the first strand cDNA molecule resulting in a promoter embedded in each tandem repeat of the TS-DNA. Because transcription, like rolling circle amplification, is a process that can go on continuously (with re-initiation), multiple transcripts can be produced from each of the multiple promoters present in the TS-DNA. RCT effectively adds another level of amplification of first strand cDNA molecules. RCT is further described in U.S. Pat. No. 6,143,495. First strand cDNA molecules can also be directly transcribed (that is, not in conjunction with rolling circle amplification). The amplified product will be RNA. Transcription of first strand cDNA molecules can produce a long tandem repeat transcript if the first strand cDNA molecule does not have a transcription termination sequence. Production of tandem repeat transcript is useful, for example, for making transcripts that are copies of the source RNA.

The transcripts generated in RCT or direct transcription can be labeled and/or detected using the same labels, labeling methods, and detection methods described for use with TS-DNA. Most of these labels and methods are adaptable for use with nucleic acids in general. A useful method of labeling RCT transcripts is by direct labeling of the transcripts by incorporation of labeled nucleotides, most preferably biotinylated nucleotides, during transcription. RCT transcripts can also be detected in real-time, using, for example, fluorescent change probes.

Transcripts produced from tandem sequence DNA can be translated in vitro to produce the encoded protein, used as probes, or put to any other use. Translation of tandem repeat transcripts and tandem sequence transcripts can be useful for making proteins encoded by the cDNA produced from a given RNA sample (that is, proteins encoded by a cDNA library). The resulting proteins can be screened, analyzed, used as antigens, used as markers, or used for any other purpose. The proteins produced from transcripts of cDNA libraries can constitute a protein library. The proteins produced by translation of tandem repeat transcripts and tandem sequence transcripts can be labeled directly or indirectly, during translation or following translation.

The transcripts produced in the disclosed method can be used for any purpose. Useful purposes include, for example, detecting specific RNA molecules and/or sequences; detecting a population or set of RNA molecules and/or sequences; analyzing or sequencing specific RNA molecules and/or sequences; analyzing or sequencing a population or set of RNA molecules and/or sequences; cataloging a population or set of RNA molecules and/or sequences; using tandem repeat transcripts, tandem sequence transcripts, or a combination, as probes, markers, hybridization probes, primers, or a combination; cloning specific RNA molecules and/or sequences; and cloning a population or set of RNA molecules and/or sequences. Thus, for example, the transcripts produced in the disclosed method can be used to identify or analyze the RNA molecules and/or sequences expressed in different cells, tissues, and/or samples, and compare the RNA molecules and/or sequences expressed in different cells, tissues, and/or samples. The transcripts can be used in a hybridization assay.

F. Detection of Amplification Products

Products of the amplification operation (for example, tandem sequence DNA, DNA produced by multiple strand displacement amplification, tandem sequence transcripts, and tandem repeat transcripts) can be detected using any nucleic acid detection technique. For real-time detection, the amplification products and the progress of amplification are detected during the amplification operation. Real-time detection is usefully accomplished using one or more or one or a combination of fluorescent change probes and fluorescent change primers. Other detection techniques can be used, either alone or in combination with real-timer detection and/or detection involving fluorescent change probes and primers. Many techniques are known for detecting nucleic acids. The nucleotide sequence of the amplified sequences also can be determined using any suitable technique.

1. Primary Labeling

Primary labeling consists of incorporating labeled moieties, such as fluorescent nucleotides, biotinylated nucleotides, digoxygenin-containing nucleotides, or bromodeoxyuridine, during rolling circle replication, during transcription, and/or during multiple strand displacement amplification. For example, fluorescent labels can be incorporated into replicated nucleic acid by using fluorescently labeled primers, such as fluorescent change rolling circle replication primers. In another example, one can incorporate cyanine dye UTP analogs (Yu et al. (1994)) at a frequency of 4 analogs for every 100 nucleotides. A preferred method for detecting nucleic acid amplified in situ is to label the DNA during amplification with BrdUrd, followed by binding of the incorporated BUDR with a biotinylated anti-BUDR antibody (Zymed Labs, San Francisco, Calif.), followed by binding of the biotin moieties with Streptavidin-Peroxidase (Life Sciences, Inc.), and finally development of fluorescence with Fluorescein-tyramide (DuPont de Nemours & Co., Medical Products Dept.).

A useful form of primary labeling is the use of fluorescent change primers in the amplification operation. Fluorescent change primers exhibit a change in fluorescence intensity or wavelength based on a change in the form or conformation of the primer and the amplified nucleic acid. Stem quenched primers are primers that when not hybridized to a complementary sequence form a stem structure (either an intramolecular stem structure or an intermolecular stem structure) that brings a fluorescent label and a quenching moiety into proximity such that fluorescence from the label is quenched. When the primer binds to a complementary sequence, the stem is disrupted, the quenching moiety is no longer in proximity to the fluorescent label and fluorescence increases. In the disclosed method, stem quenched primers can be used as primers for nucleic acid synthesis and thus become incorporated into the synthesized or amplified nucleic acid. Examples of stem quenched primers are peptide nucleic acid quenched primers and hairpin quenched primers.

Peptide nucleic acid quenched primers are primers associated with a peptide nucleic acid quencher or a peptide nucleic acid fluor to form a stem structure. The primer contains a fluorescent label or a quenching moiety and is associated with either a peptide nucleic acid quencher or a peptide nucleic acid fluor, respectively. This puts the fluorescent label in proximity to the quenching moiety. When the primer is replicated, the peptide nucleic acid is displaced, thus allowing the fluorescent label to produce a fluorescent signal.

Hairpin quenched primers are primers that when not hybridized to a complementary sequence form a hairpin structure (and, typically, a loop) that brings a fluorescent label and a quenching moiety into proximity such that fluorescence from the label is quenched. When the primer binds to a complementary sequence, the stem is disrupted, the quenching moiety is no longer in proximity to the fluorescent label and fluorescence increases. Hairpin quenched primers are typically used as primers for nucleic acid synthesis and thus become incorporated into the synthesized or amplified nucleic acid. Examples of hairpin quenched primers are Amplifluor primers and scorpion primers.

Cleavage activated primers are primers where fluorescence is increased by cleavage of the primer. Generally, cleavage activated primers are incorporated into replicated strands and are then subsequently cleaved. Cleavage activated primers can include a fluorescent label and a quenching moiety in proximity such that fluorescence from the label is quenched. When the primer is clipped or digested (typically by the 5'-3' exonuclease activity of a polymerase during amplification), the quenching moiety is no longer in proximity to the fluorescent label and fluorescence increases. Little et al., Clin. Chem. 45:777–784 (1999), describe the use of cleavage activated primers.

2. Secondary Labeling

Secondary labeling consists of using suitable molecular probes, such as detection probes, to detect the amplified nucleic acids. For example, a cDNA primer may be designed to contain several repeats of a known arbitrary sequence, referred to as detection tags. These detection tags are incorporated into first strand cDNA molecules when the cDNA primer is incorporated into the first strand cDNA molecules. Detection probes can then be hybridized to these detection tags. The detection probes may be labeled as described above with, for example, an enzyme, fluorescent moieties, or radioactive isotopes. By using three detection tags per first strand cDNA molecule, and four fluorescent moieties per each detection probe, one may obtain a total of twelve fluorescent signals for every first strand cDNA molecule repeat in the TS-DNA, yielding a total of, for example, 12,000 fluorescent moieties for every first strand cDNA molecule that is amplified by RCA. Detection probes can interact by hybridization or annealing via normal Watson-Crick base-pairing (or related alternatives) or can interact with double-stranded targets to form a triple helix. Such triplex-forming detection probes can be used in the same manner as other detection probes, such as in the form of fluorescent change probes. Detection probes can also be targeted to cDNA sequence (derived from the source RNA molecule) in the first strand cDNA molecules.

A useful form of secondary labeling is the use of fluorescent change probes and primers in or following the amplification operation. Hairpin quenched probes are probes that when not bound to a target sequence form a hairpin structure (and, typically, a loop) that brings a fluorescent label and a quenching moiety into proximity such that fluorescence from the label is quenched. When the probe binds to a target sequence, the stem is disrupted, the quenching moiety is no longer in proximity to the fluorescent label and fluorescence increases. Examples of hairpin quenched probes are molecular beacons, fluorescent triplex oligos, triplex molecular beacons, triplex FRET probes, and QPNA probes.

Cleavage activated probes are probes where fluorescence is increased by cleavage of the probe. Cleavage activated probes can include a fluorescent label and a quenching moiety in proximity such that fluorescence from the label is quenched. When the probe is clipped or digested (typically by the 5'-3' exonuclease activity of a polymerase during or following amplification), the quenching moiety is no longer in proximity to the fluorescent label and fluorescence increases. TaqMan probes are an example of cleavage activated probes.

Cleavage quenched probes are probes where fluorescence is decreased or altered by cleavage of the probe. Cleavage quenched probes can include an acceptor fluorescent label and a donor moiety such that, when the acceptor and donor are in proximity, fluorescence resonance energy transfer from the donor to the acceptor causes the acceptor to fluoresce. The probes are thus fluorescent, for example, when hybridized to a target sequence. When the probe is clipped or digested (typically by the 5'-3' exonuclease activity of a polymerase during or after amplification), the donor moiety is no longer in proximity to the acceptor fluorescent label and fluorescence from the acceptor decreases. If the donor moiety is itself a fluorescent label, it can release energy as fluorescence (typically at a different wavelength than the fluorescence of the acceptor) when not in proximity to an acceptor. The overall effect would then be a reduction of acceptor fluorescence and an increase in donor fluorescence. Donor fluorescence in the case of cleavage quenched probes is equivalent to fluorescence generated by cleavage activated probes with the acceptor being the quenching moiety and the donor being the fluorescent label. Cleavable FRET (fluorescence resonance energy transfer) probes are an example of cleavage quenched probes.

Fluorescent activated probes are probes or pairs of probes where fluorescence is increased or altered by hybridization of the probe to a target sequence. Fluorescent activated probes can include an acceptor fluorescent label and a donor moiety such that, when the acceptor and donor are in proximity (when the probes are hybridized to a target sequence), fluorescence resonance energy transfer from the donor to the acceptor causes the acceptor to fluoresce. Fluorescent activated probes are typically pairs of probes designed to hybridize to adjacent sequences such that the acceptor and donor are brought into proximity. Fluorescent activated probes can also be single probes containing both a donor and acceptor where, when the probe is not hybridized to a target sequence, the donor and acceptor are not in proximity but where the donor and acceptor are brought into proximity when the probe hybridized to a target sequence. This can be accomplished, for example, by placing the donor and acceptor on opposite ends a the probe and placing target complement sequences at each end of the probe where the target complement sequences are complementary to adjacent sequences in a target sequence. If the donor moiety of a fluorescent activated probe is itself a fluorescent label, it can release energy as fluorescence (typically at a different wavelength than the fluorescence of the acceptor) when not in proximity to an acceptor (that is, when the probes are not hybridized to the target sequence). When the probes hybridize to a target sequence, the overall effect would then be a reduction of donor fluorescence and an increase in acceptor fluorescence. FRET probes are an example of fluorescent activated probes. Stem quenched primers (such as peptide nucleic acid quenched primers and hairpin quenched primers) can be used as secondary labels.

3. Combinatorial Multicolor Coding

One form of multiplex detection involves the use of a combination of labels that either fluoresce at different wavelengths or are colored differently. One of the advantages of fluorescence for the detection of hybridization probes is that several targets can be visualized simultaneously in the same sample. Using a combinatorial strategy, many more targets can be discriminated than the number of spectrally resolvable fluorophores. Combinatorial labeling provides the simplest way to label probes in a multiplex fashion since a probe fluor is either completely absent (−) or present in unit amounts (+); image analysis is thus more amenable to automation, and a number of experimental artifacts, such as differential photobleaching of the fluors and the effects of changing excitation source power spectrum, are avoided. Combinatorial labeling can be used with fluorescent change probes and primers.

The combinations of labels establish a code for identifying different detection probes and, by extension, different target molecules to which those detection probes are associated with. This labeling scheme is referred to as Combinatorial Multicolor Coding (CMC). Such coding is described by Speicher et al., *Nature Genetics* 12:368–375 (1996). Use of CMC in connection with rolling circle amplification is described in U.S. Pat. No. 6,143,495. Any number of labels, which when combined can be separately detected, can be used for combinatorial multicolor coding. It is preferred that 2, 3, 4, 5, or 6 labels be used in combination. It is most preferred that 6 labels be used. The number of labels used establishes the number of unique label combinations that can be formed according to the formula $2^N-1$, where N is the number of labels. According to this formula, 2 labels form three label combinations, 3 labels form seven label combinations, 4 labels form 15 label combinations, 5 labels form 31 label combinations, and 6 labels form 63 label combinations.

For combinatorial multicolor coding, a group of different detection probes can be used as a set. Each type of detection probe in the set is labeled with a specific and unique combination of fluorescent labels. For those detection probes assigned multiple labels, the labeling can be accomplished by labeling each detection probe molecule with all of the required labels. Alternatively, pools of detection probes of a given type can each be labeled with one of the required labels. By combining the pools, the detection probes will, as a group, contain the combination of labels required for that type of detection probe. Where each detection probe is labeled with a single label, label combinations can also be generated by using first strand cDNA molecules with coded combinations of detection tags complementary to the different detection probes. In this scheme, the first strand cDNA molecules will contain a combination of detection tags representing the combination of labels required for a specific label code. Further illustrations are described in U.S. Pat. No. 6,143,495. Combinatorial multicolor coding can be used with fluorescent change probes and primers. Use of pools of detection probes (or other probes and primers used in the method), each probe with a single label, is preferred when fluorescent change probes (or primers) are used.

Speicher et al. describes a set of fluors and corresponding optical filters spaced across the spectral interval 350–770 nm that give a high degree of discrimination between all possible fluor pairs. This fluor set, which is preferred for combinatorial multicolor coding, consists of 4'-6-diamidino-2-phenylinodole (DAPI), fluorescein (FITC), and the cyanine dyes Cy3, Cy3.5, Cy5, Cy5.5 and Cy7. Any subset of this preferred set can also be used where fewer combinations are required. The absorption and emission maxima, respectively, for these fluors are: DAPI (350 nm; 456 nm), FITC (490 nm; 520 nm), Cy3 (554 nm; 568 nm), Cy3.5 (581 nm; 588 nm), Cy5 (652 nm; 672 nm), Cy5.5 (682 nm; 703 nm) and Cy7 (755 nm; 778 nm). The excitation and emission spectra, extinction coefficients and quantum yield of these fluors are described by Ernst et al., *Cytometry* 10:3–10 (1989), Mujumdar et al., *Cytometry* 10:11–19 (1989), Yu, *Nucleic Acids Res.* 22:3226–3232 (1994), and Waggoner, *Meth. Enzymology* 246:362–373 (1995). These fluors can all be excited with a 75W Xenon arc.

To attain selectivity, filters with bandwidths in the range of 5 to 16 nm are preferred. To increase signal discrimination, the fluors can be both excited and detected at wavelengths far from their spectral maxima. Emission bandwidths can be made as wide as possible. For low-noise detectors, such as cooled CCD cameras, restricting the excitation bandwidth has little effect on attainable signal to noise ratios. A list of preferred filters for use with the preferred fluor set is listed in Table 1 of Speicher et al. It is important to prevent infra-red light emitted by the arc lamp from reaching the detector; CCD chips are extremely sensitive in this region. For this purpose, appropriate IR blocking filters can be inserted in the image path immediately in front of the CCD window to minimize loss of image quality. Image analysis software can then be used to count and analyze the spectral signatures of fluorescent dots.

G. cDNA Library Analysis

The disclosed method can be used to produce replicated strands that serve as a cDNA library of a nucleic acid sample. Such a cDNA library can be used for any purpose, including, for example, detection of sequences, production of probes, production of nucleic acid arrays or chips, and comparison with nucleic acids in other cDNA libraries. Similarly prepared cDNA libraries of other nucleic acid samples to allow convenient detection of differences between the samples. The cDNA libraries can be used both for detection of related nucleic acid samples and comparison of nucleic acid samples. For example, the presence or identity of specific organisms can be detected by producing a cDNA library of the test organism and comparing the resulting cDNA. library with reference cDNA libraries prepared from known organisms. Changes and differences in gene expression patterns can also be detected by preparing cDNA libraries of mRNA from different cell samples and comparing the cDNA libraries. The replicated strands and/or transcripts can also be used to produce a set of probes or primers that is specific for the source of a nucleic acid sample. The replicated strands and/or transcripts can also be used as a fingerprint of nucleic acid sequences present in a sample. cDNA libraries can be made up of, or derived from, the mRNA of a sample such that the entire relevant mRNA content of the sample is substantially represented.

cDNA libraries can be stored or archived for later use. For example, replicated strands produced in the disclosed method can be physically stored, either in solution, frozen, or attached or adhered to a solid-state substrate such as an array. Storage in an array is useful for providing an archived probe set derived from the nucleic acids in any sample of interest. As another example, informational content of, or derived from, nucleic acid fingerprints can also be stored. Such information can be stored, for example, in or as computer readable media. Examples of informational content of cDNA libraries include nucleic acid sequence information (complete or partial); differential nucleic acid sequence information such as sequences present in one sample but not another; hybridization patterns of replicated strands to, for example, nucleic acid arrays, sets, chips, or other replicated strands. Numerous other data that is or can be derived from cDNA libraries and replicated strands produced in the disclosed method can also be collected, used, saved, stored, and/or archived.

cDNA libraries can also contain or be made up of other information derived from the information generated in the disclosed method, and can be combined with information obtained or generated from any other source. The informational nature of cDNA libraries produced using the disclosed method lends itself to combination and/or analysis using known bioinformatics systems and methods.

cDNA libraries of nucleic acid samples and RNA samples can be compared to a similar cDNA library derived from any other sample to detect similarities and differences in the samples (which is indicative of similarities and differences in the nucleic acids in the samples). For example, a cDNA library of a first RNA sample can be compared to a cDNA library of a sample from the same type of organism as the first RNA sample, a sample from the same type of tissue as the first RNA sample, a sample from the same organism as the first RNA sample, a sample obtained from the same source but at time different from that of the first RNA sample, a sample from an organism different from that of the first RNA sample, a sample from a type of tissue different from that of the first RNA sample, a sample from a strain of organism different from that of the first RNA sample, a sample from a species of organism different from that of the first RNA sample, or a sample from a type of organism different from that of the first RNA sample.

The same type of tissue is tissue of the same type such as liver tissue, muscle tissue, or skin (which may be from the same or a different organism or type of organism). The same organism refers to the same individual, animal, or cell. For example, two samples taken from a patient are from the same organism. The same source is similar but broader, referring to samples from, for example, the same organism, the same tissue from the same organism, the same DNA molecule, or the same DNA library. Samples from the same source that are to be compared can be collected at different times (thus allowing for potential changes over time to be detected). This is especially useful when the effect of a treatment or change in condition is to be assessed. Samples from the same source that have undergone different treatments can also be collected and compared using the disclosed method. A different organism refers to a different individual organism, such as a different patient, a different individual animal. Different organism includes a different organism of the same type or organisms of different types. A different type of organism refers to organisms of different types such as a dog and cat, a human and a mouse, or *E. coli* and Salmonella. A different type of tissue refers to tissues of different types such as liver and kidney, or skin and brain. A different strain or species of organism refers to organisms differing in their species or strain designation as those terms are understood in the art.

DNA in the cDNA library or any form of DNA or RNA produced in the disclosed method (such as tandem sequence DNA, tandem sequence DNA fragments, tandem sequence DNA molecules, tandem repeat units, tandem sequence transcripts, tandem repeat transcripts) can be analyzed by, for example, detecting one or more target sequences in the DNA or RNA. A target sequence is any sequence of interest. Target sequences in nucleic acids produced in the disclosed method are derived from sequence (that is, target sequence) in the source RNA molecules. Such a target sequence in the RNA molecule from which the target sequence in product nucleic acids is derived can be said to correspond to the target sequence in the product nucleic acid. Similarly, the target sequence in a product nucleic acid can be said to correspond to the target sequence in the RNA molecule. A target sequence in a product nucleic acid also can be said to correspond to the RNA molecule in which the target sequence corresponding to the target sequence in the product nucleic acid is found. Detection of the target sequence in the product nucleic acid indicates the presence of the corresponding RNA molecule in the RNA sample. A plurality of detected target sequences can constitute a catalog of sequences derived from the RNA sample.

Target sequences can be chosen for any reason. For example, target sequences that are related to a disease or condition are useful to detect. Sequences that are related to a disease or condition include sequences embodying or indicating a mutation or alteration that is associated with the disease or condition. Many nucleic acid sequences are known that are related to a disease or condition. Target sequences that indicate that a subject is or is not at risk for a disease or condition are useful to detect. Sequences that indicate that a subject is at risk for a disease or condition include sequences embodying or indicating a mutation or alteration that is associated with the disease or condition or a risk of the disease or condition. Many nucleic acid sequences are known that are associated with a risk of a disease or condition. A risk of a disease or condition refers to a chance above the background or average chance that a presently non-existent disease or condition will develop in the future. A subject at risk for a disease or condition has a risk of developing the disease or condition.

Tandem sequence DNA or other nucleic acid product produced in the disclosed method can be detected. The detected tandem sequence DNA (or other nucleic acid product) can constitute a catalog of sequences derived from an RNA sample. It is useful to broadly amplify and detect RNA molecules in an RNA sample. Thus, it is useful if a catalog of sequences comprises a substantial number, a significant number, or a notable number of the RNA molecules in the RNA sample. A substantial number of RNA molecules means 90% or more of the RNA molecules in the RNA sample. A significant number of RNA molecules means 50% or more of the RNA molecules in the RNA sample. A notable number of RNA molecules means 10% or more of the RNA molecules in the RNA sample.

The quality of the amplification products can be assessed in any suitable manner. For example, the amount of amplification, the amplification bias, and/or the relative level of full length cDNA molecules can be assessed. Illustrations of assessing the amount of amplification and amplification bias are in the examples. The relative amount of full length cDNA can be determined, for example, by measuring the abundance sequence from the 3' end of an RNA molecule relative to the abundance of sequence from the 5' end of the RNA molecule.

H. Specific Embodiments

Disclosed is a method of amplifying RNA sequences, the method comprising incubating a cDNA primer and an RNA sample comprising RNA molecules under conditions that promote synthesis of first strand cDNA molecules from the RNA molecules, incubating a circularization probe and the first strand cDNA molecules under conditions that promote circularization of the first strand cDNA molecules, and incubating the circularized first strand cDNA molecules under conditions that promote rolling circle replication of the circularized first strand cDNA molecules, thereby amplifying RNA sequences.

The rolling circle replication can result in formation of tandem sequence DNA, wherein the tandem sequence DNA can be replicated to form secondary tandem sequence DNA, wherein the tandem sequence DNA and the secondary tandem sequence DNA can form double-stranded tandem sequence DNA. Each double-stranded tandem sequence DNA can comprise multiple tandem repeat units of the same sequence, wherein each tandem repeat unit can comprise one or more cleavage sites of interest. The method can further comprise cleaving the double-stranded tandem sequence DNA at a plurality of the cleavage sites resulting in tandem sequence DNA fragments, wherein at least one of the tandem sequence DNA fragments does not comprise a plurality of tandem repeat units.

Each tandem repeat unit can comprise a single cleavage site of interest, wherein the cDNA primer can comprise the cleavage site of interest. The cleavage site can be a cleavage site for a restriction endonuclease, wherein the restriction endonuclease has a recognition sequence comprising at least seven nucleotides. The restriction endonuclease can have a recognition sequence comprising at least eight nucleotides. The restriction endonuclease can be Not I, Asc I, AsiS I, Fse I, Pac I, Pme I, Sbf I, Sfi I, or Swa I. The cleavage site can be a cleavage site for a restriction endonuclease, wherein the restriction endonuclease can have a recognition sequence that occurs once every. 65,536 nucleotides or more on average. Each tandem repeat unit can comprise a single cleavage site of interest, wherein the circularization probe can comprise the cleavage site of interest.

Each tandem repeat unit can comprise a single cleavage site of interest, wherein at least one of the tandem sequence DNA fragments can consist of a single tandem repeat unit. A plurality of the tandem sequence DNA fragments can consist of a single tandem repeat unit. A majority of the tandem sequence DNA fragments can consist of a single tandem repeat unit. Substantially all of the tandem sequence DNA fragments can consist of a single tandem repeat unit. The method can further comprise cloning one or more of the single tandem repeat units. The single tandem repeat units can be separated by size prior to cloning. Single tandem repeat units having sizes of interest can be cloned. Single tandem repeat units having a size the same as or greater than a size of interest can be cloned. The cloned tandem repeat units can constitute a cDNA library.

The sequence of the single tandem repeat unit can correspond to the sequence of one of the circularized first strand cDNA molecules, wherein the sequence of the single tandem repeat unit can be a circular permutation of the sequence of one of the circularized first strand cDNA molecules. The sequence of the single tandem repeat unit can correspond to the sequence of one of the circularized first strand cDNA molecules, wherein the sequence of the single tandem repeat is not a circular permutation of the sequence of one of the circularized first strand cDNA molecules. The single tandem repeat units can constitute a cDNA library.

Rolling circle replication can be primed by a rolling circle replication primer, wherein the rolling circle replication primer can further comprise a promoter portion. The promoter portion can be a promoter for a phage RNA polymerase or a bacterial RNA polymerase. The promoter can be a promoter for T3 RNA polymerase, T7 RNA polymerase, or SP6 RNA polymerase. The method can further comprise transcribing the tandem repeat units, whereby tandem repeat transcripts are produced, wherein the tandem repeat transcripts are transcripts of single tandem repeat units. The tandem repeat transcripts can be used, directly or indirectly, in a hybridization assay. The tandem repeat transcripts can be associated with a solid-state substrate. The tandem repeat transcripts can be translated.

The cDNA primer further can comprise a promoter portion. The promoter portion can be a promoter for a phage RNA polymerase or a bacterial RNA polymerase. The promoter can be a promoter for T3 RNA polymerase, T7 RNA polymerase, or SP6 RNA polymerase. The method can further comprise transcribing the tandem repeat units, whereby tandem repeat transcripts are produced, wherein the tandem repeat transcripts are transcripts of single tandem repeat units. The tandem repeat transcripts can be used, directly or indirectly, in a hybridization assay. The tandem repeat transcripts can be associated with a solid-state substrate. The tandem repeat transcripts can be translated. The tandem repeat units can be used, directly or indirectly, in a hybridization assay. The tandem repeat units can be associated with a solid-state substrate.

The method can further comprise inserting one or more of the tandem sequence DNA fragments into one or more vectors to form one or more recombinant vectors. The tandem sequence DNA fragments can be separated by size prior to insertion into vectors, wherein only tandem sequence DNA fragments having sizes of interest are inserted into vectors. Tandem sequence DNA fragments having a size the same as or greater than a size of interest can be cloned. The recombinant vectors can constitute a cDNA library.

The method can further comprise cloning one or more of the tandem sequence DNA fragments. The tandem sequence DNA fragments can be separated by size prior to cloning, wherein only tandem sequence DNA fragments having sizes of interest are cloned. Tandem sequence DNA fragments having a size the same as or greater than a size of interest can be cloned. The cloned tandem sequence DNA fragments can constitute a cDNA library. The tandem sequence DNA fragments can constitute a cDNA library. At least one of the tandem sequence DNA fragments can comprise a single tandem repeat unit, wherein the method can further comprise cloning one or more of the single tandem repeat units. The single tandem repeat units can be separated by size prior to cloning, wherein only single tandem repeat units having sizes of interest are cloned, Single tandem repeat units having a size the same as or greater than a size of interest can be cloned. The cloned tandem repeats can constitute a cDNA library. The tandem sequence DNA fragments can be used, directly or indirectly, in a hybridization assay. The tandem sequence DNA fragments can be associated with a solid-state substrate.

The cDNA primer can comprise an RNA complement portion, wherein the RNA complement portion hybridizes to one or more of the RNA molecules, wherein the cDNA primer is incorporated into the first strand cDNA molecules during synthesis of the first strand cDNA molecules. The RNA complement portion can comprise poly(dT), wherein the RNA molecules are mRNA molecules. The RNA complement portion can be complementary to sequence in one or more RNA molecules. The RNA complement portion can be complementary to sequence in one of the RNA molecules, wherein the cDNA primer can be specific for the RNA molecule. The cDNA primer can further comprise a cleavage site. The cleavage site can be a cleavage site for a restriction endonuclease, wherein the restriction endonuclease has a recognition sequence comprising at least seven nucleotides. The restriction endonuclease can have a recognition sequence comprising at least eight nucleotides. The restriction endonuclease can be Not I, Asc I, AsiS I, Fse I, Pac I, Pme I, Sbf I, Sfi I, or Swa I. The cleavage site can be a cleavage site for a restriction endonuclease, wherein the restriction endonuclease can have a recognition sequence that occurs once every 65,536 nucleotides or more on average.

The rolling circle replication can result in formation of tandem sequence DNA, wherein the tandem sequence DNA can be replicated to form secondary tandem sequence DNA, wherein the tandem sequence DNA and the secondary tandem sequence DNA can form double-stranded tandem sequence DNA, wherein each double-stranded tandem sequence DNA can comprise multiple tandem repeats of the same sequence, wherein each tandem repeat can comprise the cleavage site. The method can further comprise cleaving the double-stranded tandem sequence DNA at a plurality of the cleavage sites resulting in tandem sequence DNA fragments. The cDNA primer can further comprise a probe complement portion, wherein the probe complement portion can be complementary to sequence in the circularization probe. The cDNA primer can further comprise a primer complement portion, wherein the primer complement portion can be complementary to a rolling circle replication primer.

The cDNA primer can further comprise a primer matching portion, wherein the primer matching portion can match sequence in a secondary DNA strand displacement primer. The cDNA primer can further comprise a promoter portion. The cDNA primer can further comprise a primer matching portion, wherein the primer matching portion can match sequence in a secondary DNA strand displacement primer. The cDNA primer can further comprise a promoter portion. The promoter portion can be a promoter for a phage RNA polymerase or a bacterial RNA polymerase. The promoter can be a promoter for T3 RNA polymerase, T7 RNA polymerase, or SP6 RNA polymerase. The cDNA primer can comprise nucleotides, wherein one or more of the nucleotides are ribonucleotides. From about 10% to about 50% of the nucleotides can be ribonucleotides. About 50% or more of the nucleotides can be ribonucleotides. All of the nucleotides can be ribonucleotides.

The cDNA primer can comprise nucleotides, wherein one or more of the nucleotides are 2'-O-methyl ribonucleotides. From about 10% to about 50% of the nucleotides can be 2'-O-methyl ribonucleotides. About 50% or more of the nucleotides can be 2'-O-methyl ribonucleotides. All of the nucleotides can be 2'-O-methyl ribonucleotides. The cDNA primer can comprise nucleotides, wherein the nucleotides can be a mixture of ribonucleotides and 2'-O-methyl ribonucleotides. The cDNA primer can comprise nucleotides, wherein the nucleotides can be a mixture of deoxyribonucleotides and 2'-O-methyl ribonucleotides.

The cDNA primer is incorporated into the first strand cDNA molecules during synthesis of the first strand cDNA molecules, wherein the circularization probe can comprise a cDNA complement portion and a primer complement portion, wherein the cDNA complement portion can hybridize to one or more of the first strand cDNA molecules, wherein the primer complement portion can hybridize to the cDNA primer incorporated into the first strand cDNA molecules, wherein hybridization of the cDNA complement portion to the first strand cDNA molecules and hybridization of the primer complement portion to the cDNA primer brings the ends of the first strand cDNA molecules into proximity thereby mediating circularization of the first strand cDNA molecules.

The cDNA complement portion can comprise a random or partially random sequence. The cDNA complement portion can comprise nucleotides, wherein one or more of the nucleotides can comprise a universal base. The universal base can be 5-nitroindole or 3-nitropyrrole. The cDNA complement portion can comprise nucleotides, wherein one or more of the nucleotides can base pair with more than one type of nucleotide. The nucleotide that can base pair with more than one type of nucleotide can be inosine or a nucleotide comprising a universal base. The universal base can be 5-nitroindole or 3-nitropyrrole. The circularization probe can further comprise a cleavage site, wherein the primer complement portion can comprise the cleavage site.

The cleavage site can be a cleavage site for a restriction endonuclease, wherein the restriction endonuclease can have a recognition sequence comprising at least seven nucleotides. The restriction endonuclease can have a recognition sequence comprising at least eight nucleotides. The restriction endonuclease cna be Not I, Asc I, AsiS I, Fse I, Pac I, Pme I, Sbf I, Sfi I, or Swa I. The cleavage site can be a cleavage site for a restriction endonuclease, wherein the restriction endonuclease can have a recognition sequence that occurs once every 65,536 nucleotides or more on average.

The rolling circle replication can result in formation of tandem sequence DNA, wherein the tandem sequence DNA can be replicated to form secondary tandem sequence DNA, wherein the tandem sequence DNA and the secondary tandem sequence DNA can form double-stranded tandem sequence DNA, wherein each double-stranded tandem sequence DNA can comprise multiple tandem repeats of the same sequence, wherein each tandem repeat can comprise the cleavage site. The method can further comprise cleaving the double-stranded tandem sequence DNA at a plurality of the cleavage sites resulting in tandem sequence DNA fragments.

The primer complement portion can be complementary to sequence in the cDNA primer. The circularization probe further comprises a second primer complement portion, wherein the second primer complement portion can be complementary to a secondary DNA strand displacement primer. The circularization probe can further comprises primer matching portion, wherein the primer matching portion can match sequence in a rolling circle replication primer. The circularization probe can further comprise a promoter portion. The circularization probe can further comprise a primer matching portion, wherein the primer matching portion can match sequence in a secondary DNA strand displacement primer.

The circularization probe can further comprise a promoter portion. The promoter portion can be a promoter for a phage RNA polymerase or a bacterial RNA polymerase. The promoter can be a promoter for T3 RNA polymerase, T7 RNA polymerase, or SP6 RNA polymerase. The circularization probe can comprise nucleotides, wherein one or more of the nucleotides are ribonucleotides. From about 10% to about 50% of the nucleotides can be ribonucleotides. About 50% or more of the nucleotides can be ribonucleotides. All of the nucleotides can be ribonucleotides.

The circularization probe can comprise nucleotides, wherein one or more of the nucleotides can be 2'-O-methyl ribonucleotides. From about I0% to about 50% of the nucleotides can be 2'-O-methyl ribonucleotides. About 50% or more of the nucleotides are 2'-O-methyl ribonucleotides. All of the nucleotides can be 2'-O-methyl ribonucleotides. The circularization probe can comprise nucleotides, wherein the nucleotides can be a mixture of ribonucleotides and 2'-O-methyl ribonucleotides. The circularization probe can comprise nucleotides, wherein the nucleotides can be a mixture of deoxyribonucleotides and 2'-O-methyl ribonucleotides.

Rolling circle replication can be primed by a rolling circle replication primer, wherein the rolling circle replication primer can have a random sequence, wherein the rolling circle replication can be primed from a plurality of locations on the circularized first strand cDNA molecules. The rolling circle replication can result in formation of tandem sequence DNA, wherein the tandem sequence DNA can be replicated to form secondary tandem sequence DNA, wherein replication of the tandem sequence DNA can be primed by the rolling circle replication primer. The circularized first strand cDNA molecules can be amplified via exponential rolling circle amplification.

Rolling circle replication can be primed by a plurality of rolling circle replication primers, wherein the rolling circle replication can be primed from a plurality of locations on the circularized first strand cDNA molecules. The rolling circle replication can result in formation of tandem sequence DNA, wherein the tandem sequence DNA can be replicated to form secondary tandem sequence DNA, wherein replication of the tandem sequence DNA can be primed by one or more secondary DNA strand displacement primers. The circularized first strand cDNA molecules can be amplified via exponential rolling circle amplification.

Rolling circle replication can be primed by one or more rolling circle replication primers, wherein the rolling circle replication can result in formation of tandem sequence DNA, wherein the tandem sequence DNA is not replicated, wherein the tandem sequence DNA can comprise sequence matching sequence in the RNA molecules. The tandem sequence DNA can be used, directly or indirectly, in a hybridization assay. The tandem sequence DNA can be associated with a solid-state substrate.

Rolling circle replication can be primed by the circularization probe, wherein the rolling circle replication can result in formation of tandem sequence DNA, wherein the tandem sequence DNA is not replicated, wherein the tandem sequence DNA can comprise sequence matching sequence in the RNA molecules. The tandem sequence DNA can be used, directly or indirectly, in a hybridization assay. The tandem sequence DNA can be associated with a solid-state substrate.

Rolling circle replication can be primed by one or more rolling circle replication primers, wherein the rolling circle replication can result in formation of tandem sequence DNA, wherein the tandem sequence DNA can be replicated to form secondary tandem sequence DNA, wherein replication of the tandem sequence DNA can be primed by one or more secondary DNA strand displacement primers. The rolling circle replication primers can have 5' phosphates, wherein the secondary DNA strand displacement primers can have 5' hydroxyls, wherein the tandem sequence DNA can have 5' phosphates, wherein the secondary tandem sequence DNA has 5' hydroxyls. The method can further comprise incubating the tandem sequence DNA and secondary tandem sequence DNA in the presence of a phosphate-dependent exonuclease, whereby the tandem sequence DNA is degraded and the secondary tandem sequence DNA remains.

The phosphate-dependent exonuclease can be lambda exonuclease. The secondary tandem sequence DNA can comprise sequence complementary to sequence in the RNA molecules, wherein the secondary tandem sequence DNA can be used, directly or indirectly, in a hybridization assay. The secondary tandem sequence DNA can comprise sequence complementary to sequence in the RNA molecules, wherein the secondary tandem sequence DNA can be associated with a solid-state substrate.

Rolling circle replication can be primed by one or more rolling circle replication primers, wherein the rolling circle replication can result in formation of tandem sequence DNA, wherein the tandem sequence DNA can be replicated to form secondary tandem sequence DNA, wherein replication of the tandem sequence DNA can be primed by one or more secondary DNA strand displacement primers. The rolling circle replication primers can have 5' hydroxyls, wherein the secondary DNA strand displacement primers can have 5' phosphates, wherein the tandem sequence DNA can have 5' hydroxyls, wherein the secondary tandem sequence DNA can have 5' phosphates. The method can further comprise incubating the tandem sequence DNA and secondary tandem sequence DNA in the presence of a phosphate-dependent exonuclease, whereby the secondary tandem sequence DNA is degraded and the tandem sequence DNA remains. The phosphate-dependent exonuclease can be lambda exonuclease. The tandem sequence DNA can comprise sequence matching sequence in the RNA molecules, wherein the tandem sequence DNA can be used, directly or indirectly, in a hybridization assay. The tandem sequence DNA can comprise sequence matching sequence in the RNA molecules, wherein the tandem sequence DNA can be associated with a solid-state substrate.

Rolling circle replication can be primed by the circularization probe, wherein the rolling circle replication can result in formation of tandem sequence DNA, wherein the tandem sequence DNA can be replicated to form secondary tandem sequence DNA, wherein replication of the tandem sequence DNA can be primed by one or more secondary DNA strand displacement primers. The circularization probe can have a 5' phosphate, wherein the secondary DNA strand displacement primers can have 5' hydroxyls, wherein the tandem sequence DNA can have 5' phosphates, wherein the secondary tandem sequence DNA can have 5' hydroxyls. The method can further comprise incubating the tandem sequence DNA and secondary tandem sequence DNA in the presence of a phosphate-dependent exonuclease, whereby the tandem sequence DNA can be degraded and the secondary tandem sequence DNA remains. The phosphate-dependent exonuclease can be lambda exonuclease. The secondary tandem sequence DNA can comprise sequence complementary to sequence in the RNA molecules, wherein the secondary tandem sequence DNA can be used, directly or indirectly, in a hybridization assay. The secondary tandem sequence DNA can comprise sequence complementary to sequence in the RNA molecules, wherein the secondary tandem sequence DNA can be associated with a solid-state substrate.

Rolling circle replication can be primed by the circularization probe, wherein the rolling circle replication can result in formation of tandem sequence DNA, wherein the tandem sequence DNA can be replicated to form secondary tandem sequence DNA, wherein replication of the tandem sequence DNA can be primed by one or more secondary DNA strand displacement primers. The circularization probe can have a 5' hydroxyl, wherein the secondary DNA strand displacement primers can have 5' phosphates, wherein the tandem sequence DNA can have 5' hydroxyls, wherein the secondary tandem sequence DNA can have 5' phosphates. The method can further comprise incubating the tandem sequence DNA and secondary tandem sequence DNA in the presence of a phosphate-dependent exonuclease, whereby the secondary tandem sequence DNA is degraded and the tandem sequence DNA remains. The phosphate-dependent exonuclease can be lambda exonuclease. The tandem sequence DNA can comprise sequence matching sequence in the RNA molecules, wherein the tandem sequence DNA can be used, directly or indirectly, in a hybridization assay. The tandem sequence DNA can comprise sequence matching sequence in the RNA molecules, wherein the tandem sequence DNA can be associated with a solid-state substrate.

Rolling circle replication can be primed by a rolling circle replication primer, wherein the rolling circle replication primer can further comprise a promoter portion, wherein the rolling circle replication can result in formation of tandem sequence DNA. The promoter portion can be a promoter for a phage RNA polymerase or a bacterial RNA polymerase. The promoter can be a promoter for T3 RNA polymerase, T7 RNA polymerase, or SP6 RNA polymerase. The method can further comprise transcribing the tandem sequence DNA, whereby tandem sequence transcripts are produced. The tandem sequence transcripts can be used, directly or indirectly, in a hybridization assay. The tandem sequence transcripts can be associated with a solid-state substrate. The tandem sequence transcripts can be translated.

The cDNA primer can further comprise a promoter portion, wherein the rolling circle replication can result in formation of tandem sequence DNA. The promoter portion can be a promoter for a phage RNA polymerase or a bacterial RNA polymerase. The promoter can be a promoter for T3 RNA polymerase, T7 RNA polymerase, or SP6 RNA polymerase. The method can further comprise transcribing the tandem sequence DNA, whereby tandem sequence transcripts are produced. The tandem sequence transcripts can be used, directly or indirectly, in a hybridization assay. The tandem sequence transcripts can be associated with a solid-state substrate. The tandem sequence transcripts can be translated.

Rolling circle replication can result in formation of tandem sequence DNA, wherein the method can further comprise detecting one or more target sequences in the tandem sequence DNA. The one or more target sequences can correspond to target sequences in the RNA molecules, wherein detection of the one or more target sequences can indicate the presence of the corresponding RNA molecules in the RNA sample. The RNA sample can be derived from a subject, wherein one or more of the target sequences can be related to a disease or condition, wherein detection of the one or more target sequences related to a disease or condition can indicate that the subject from which the RNA sample is derived is or is not at risk for the related disease or condition.

A plurality of first strand cDNA molecules can be synthesized from a plurality of RNA molecules, wherein a plurality of tandem sequence DNAs can be formed, wherein the plurality of tandem sequence DNAs can correspond to the plurality of RNA molecules, wherein a plurality of target sequences can be detected, wherein the plurality of target sequences detected can constitute a catalog of sequences derived from the RNA sample. The method can further comprise comparing the catalog of sequences to another catalog of sequences produced in the same way from a different RNA sample. The presence and absence of sequences of interest in the catalog of sequences can indicate that the subject from which the RNA sample is derived is or is not at risk for a disease or condition. The rolling circle replication can result in formation of tandem sequence DNA, wherein a plurality of first strand cDNA molecules can be synthesized from a plurality of RNA molecules, wherein a plurality of tandem sequence DNAs can be formed, wherein the plurality of tandem sequence DNAs can correspond to the plurality of RNA molecules, wherein the plurality of tandem sequence DNAs can constitute a catalog of sequences derived from the RNA sample. The catalog of sequences can comprise tandem sequence DNA corresponding to a significant number of the RNA molecules in the RNA sample. The catalog of sequences can comprise tandem sequence DNA corresponding to a substantial number of the RNA molecules in the RNA sample.

Rolling circle replication can result in formation of tandem sequence DNA, wherein the method can further comprise sequencing one or more target sequences in the tandem sequence DNA. The one or more target sequences can correspond to target sequences in the RNA molecules, wherein the sequence of the one or more target sequences can correspond to sequence of the corresponding RNA molecules in the RNA sample.

The rolling circle replication can result in formation of tandem sequence DNA, wherein the method can further comprise, following the rolling circle replication, incubating the tandem sequence DNA under conditions that promote replication of the tandem sequence DNA, wherein during replication of the tandem sequence DNA at least one of the replicated strands can be displaced from the tandem sequence DNA by strand displacement replication of another replicated strand. The rolling circle replication can result in formation of tandem sequence DNA, wherein the tandem sequence DNA can be replicated to form secondary tandem sequence DNA during the rolling circle replication, wherein the method can further comprise, following the rolling circle replication, incubating the tandem sequence DNA and the secondary tandem sequence DNA under conditions that promote replication of the tandem sequence DNA and the secondary tandem sequence DNA, wherein during replication of the tandem sequence DNA and the secondary tandem sequence DNA at least one of the replicated strands can be displaced from the tandem sequence DNA or the secondary tandem sequence DNA by strand displacement replication of another replicated strand.

At least one of the first strand cDNA molecules can be ligated to at least one other first strand cDNA molecule to form one or more first strand cDNA concatemers. At least one of the first strand cDNA concatemers is not circularized, wherein the uncircularized first stand cDNA concatemer can be replicated by strand displacement replication. At least one of the first strand cDNA concatemers can be circularized, wherein the circularized first strand cDNA concatemer can be replicated by rolling circle replication. At least one of the first strand cDNA concatemers is not circularized, wherein the uncircularized first stand cDNA concatemer can be replicated by strand displacement replication, wherein at least one of the first strand cDNA concatemers can be circularized, wherein the circularized first strand cDNA concatemer is replicated by rolling circle replication.

The conditions that promote synthesis of first strand cDNA molecules can comprise incubating the cDNA primer and the RNA sample in the presence of a reverse transcriptase, wherein the conditions that promote circularization of the first strand cDNA molecules can comprise incubating the circularization probe and the first strand cDNA molecules in the presence of ligase, wherein the conditions that promote rolling circle replication of the circularized first cDNA molecules can comprise incubating the circularized first strand cDNA molecules in the presence of a DNA polymerase.

The RNA molecules can be mRNA molecules, wherein the cDNA primer can be 5'-GTGCGGCCGCTTTTTTTTTTTTTTTTTTTT-3' (SEQ ID NO:1), wherein the circularization probe can be 5'-AAAAGCGGCCGCACNNNNNNN-3' (SEQ ID NO:2), wherein the reverse transcriptase can be Superscript II reverse transcriptase, wherein the ligase can be T4 DNA ligase, wherein the DNA polymerase can be φ29 DNA polymerase. The method can further comprise, following synthesis of first strand cDNA molecules and before circularization of the first strand cDNA molecules, incubating the first strand cDNA molecules in the presence of an RNAse H activity, incubating the first strand cDNA molecules under alkaline conditions, neutralizing the first strand cDNA molecules, and purifying the first strand cDNA molecules. The RNAse H activity can be provided by an RNAse H+ reverse transcriptase, wherein the alkaline conditions can be produced by adding 0.1 M NaOH, wherein the first strand cDNA molecules can be neutralized by adding 0.1 M HCl.

Also disclosed is a method of amplifying RNA sequences, the method comprising incubating a cDNA primer and an RNA sample comprising RNA molecules under conditions that promote synthesis of first strand cDNA molecules from the RNA molecules, wherein the conditions that promote synthesis of first strand cDNA molecules comprise incubating the cDNA primer and the RNA sample in the presence of a reverse transcriptase; incubating the first strand cDNA molecules in the presence of an RNAse H activity; incubating the first strand cDNA molecules under alkaline conditions; neutralizing the first strand cDNA molecules; purifying the first strand cDNA molecules; incubating a circularization probe and the first strand cDNA molecules under conditions that promote circularization of the first strand cDNA molecules, wherein the conditions that promote circularization of the first strand cDNA molecules comprise incubating the circularization probe and the first strand cDNA molecules in the presence of ligase; and incubating the circularized first strand cDNA molecules under conditions that promote rolling circle replication of the circularized first strand cDNA molecules, thereby amplifying RNA sequences, wherein the conditions that promote rolling circle replication of the circularized first cDNA molecules comprise incubating the circularized first strand cDNA molecules in the presence of a DNA polymerase.

The RNA molecules can be mRNA molecules, wherein the cDNA primer can be 5'-GTGCGGCCGCTTTTTTTTTTTTTTTTTTTT-3' (SEQ ID NO: 1), wherein the circularization probe can be 5'-AAAAGCGGCCGCACNNNNNNN-3' (SEQ ID NO:2), wherein the reverse transcriptase can be Superscript II reverse transcriptase, wherein the RNAse H activity can be provided by an RNAse H+ reverse transcriptase, wherein the alkaline conditions can be produced by adding 0.1 M NaOH, wherein the first strand cDNA molecules can be neutralized by adding 0.1 M HCl, wherein the ligase can be T4 DNA ligase, and wherein the DNA polymerase can be φ29 DNA polymerase.

Also disclosed is a method of amplifying RNA sequences, the method comprising incubating a cDNA primer and an RNA sample comprising RNA molecules under conditions that promote synthesis of first strand cDNA molecules from the RNA molecules; incubating a circularization probe and the first strand cDNA molecules under conditions that promote ligation of the first strand cDNA molecules to each other to form first strand cDNA concatemers; and incubating the first strand cDNA concatemers under conditions that promote strand displacement replication of the first strand cDNA concatemers, thereby amplifying RNA sequences. At least one of the first strand cDNA concatemers can be circularized, wherein the circularized first strand cDNA concatemer can be replicated by rolling circle replication.

At least one of the first strand cDNA molecules can be circularized, wherein the circularized first strand cDNA molecule can be replicated by rolling circle replication. At least one of the first strand cDNA concatemers can be circularized, wherein the circularized first strand cDNA concatemer can be replicated by rolling circle replication, wherein at least one of the first strand cDNA molecules can be circularized, wherein the circularized first strand cDNA molecule can be replicated by rolling circle replication.

EXAMPLES

A. Example 1

Circularization-Dependent Amplification of Human RNA

This example demonstrates a basic form of the disclosed method by amplifying polyadenylated RNA from a human adenorectal carcinoma. Control reactions indicate that amplification was dependent on circularization of first strand cDNA molecules.

First strand cDNA was synthesized from 1 μg poly $A^+$ mRNA (human adenorectal carcinoma, SV-480) using a 5'-P-Not-1-(dT)$_{20}$ cDNA primer (SEQ ID NO: 1) and Superscript II reverse transcriptase. RNAse H+ reverse transcriptase was added to digest RNA templates. 0.1 M NaOH was then added and the mixture was incubated for minutes. The reaction was then neutralized by adding 0.1 M HCl. The first strand cDNA molecules were purified using a Qiagen column to remove dNTPs and the primer. The first strand cDNA molecules were then circularized using T4 DNA ligase and a generic circularization probe (5'-AAAAGCGGCCGCACNNNNNN-3'; SEQ ID NO:2). The NNN segment of this circularization probe anneals to the 3' end of all cDNAs, while the AAAAGCGGCCGCAC (nucleotides 1–14 of SEQ ID NO:2) segment anneals to the 5' end of the cDNAs incorporating the cDNA primer used for the cDNA synthesis.

Part of the circularized first strand cDNA molecule mixture (2 μl or 10 μl) was used for multiprimed RCA using exo-resistant p(dN)$_6$ primers, Phi-29 DNA polymerase, and dNTPs ($^{32}$P dCTP as a tracer). Part of amplification product (5 μl) was removed at different time intervals to monitor the amplification of the first strand cDNA molecules. The results indicated that amplification of the first strand cDNA molecules was dependent upon the circularization of first strand cDNA molecules.

B. Example 2

Analysis of Amplification Products

Following the design concept (FIG. 1), first strand cDNA molecules were synthesized from 1 μg poly $A^+$ mRNA from Adenocarcinoma cells (Clontech) using a 5'-phosphorylated cDNA primer as shown in FIG. 1 (oligo–dT at the 3'-end and Not I endonuclease sequence on its 5'-phosphorylated end) using Superscript II reverse transcriptase (Invitrogen) at 42° C. for 1 hr followed by AMV reverse transcriptase (Invitrogen) at 37° C. for 1 hr. The first strand cDNA was isolated from the reaction mixture using Qiagen PCR product purification kit. First strand cDNA representing 100 ng mRNA (1/10$^{th}$ reaction product) was annealed to an excess of bridge oligonucleotide (circularization probe) (1 μg) in 20 μl×T4 DNA ligase buffer (heating to 80° C. followed by slow cooling to 30° C.) followed by the addition of 40U T4 DNA ligase for 12 hrs at 30° C. A fraction of the ligated cDNA reaction mixture, representing 5 ng mRNA, was then used for 100 μl amplification reaction using exonuclease-resistant p(dN)$_6$ primers and Φ29 DNA polymerase at 30° C. for 12 hrs. Quantification of amplification product using picogreen assay indicated the formation of 100 μl of amplified DNA.

The amplification reaction was also carried out in the presence of [α$^{32}$P] dCTP to evaluate the amplification profile and to evaluate the presence of the Not I site in the amplified product. The radioactively labeled amplified product was digested with Not I and electrophoresed on a 0.8% agarose gel followed by auto-radiographic analysis. This experiment indicated that a very high molecular weight product was synthesized upon amplification of ligated cDNA. The digestion of amplification product using Not I endonuclease gave a mixture of long and short cDNA molecules demonstrating that the amplification product was originated from the ligated first strand cDNA molecules.

In order to determine fold amplification of a specific transcript within the amplification product, Taqman assays were carried out using both amplified and non-amplified cDNA samples. A Taqman probe that detects a region of the Epidermal Growth Factor Receptor (EGFR) transcript, about 2.4 kb upstream from its 3'-end, was used for this purpose. The Ct values reflect the respective abundance (copy number) of cDNA target molecules. For calculations, a difference of about 3 Ct units reflects about 10-fold difference in the abundance. The Ct value for unamplified cDNA representing 40 ng mRNA was 21.2 cycles. Whereas the Ct value for amplified cDNA representing 150 pg mRNA was 16 cycles. Thus a difference of 5 Ct units between cDNA representing 40 ng mRNA and amplified cDNA representing 150 pg mRNA suggests the presence of approximately a 70-fold abundant targets in the amplified cDNA. Taking into account that they reflect different mRNA quantities, this represents about a 20,000-fold amplification of the EGFR transcript. Since a constant amount of amplified product is obtained, irrespective of the input template, higher fold amplification of transcripts is expected if using lower amounts of ligated cDNA for amplification reactions.

C. Example 3

Analysis of Amplification Bias of Amplification Products

In order to determine the bias generated by amplification of a specific transcript from two different RNA samples, first strand cDNA synthesis was carried out from poly-A$^+$ mRNA derived from human adult brain and fetal brain (Clontech). The first strand cDNA was ligated at 4 ng/μl concentration in the presence of a circularization probe. 10 ng of ligated first strand cDNA molecules were used for transcript amplification in a 30 μl reaction volume using Φ29 DNA polymerse and exonuclease-resistant p(dN)$_6$ primers. To determine the relative abundance of DNA damage-inducible transcript (D1e3) targets per ng of the sample, Taqman assays were carried out using amplified and unamplified cDNA molecules representing adult and fetal brain mRNA. Transcript abundance in these samples was calculated by utilizing Taqman assay standard curve using varying amounts of genomic DNA (333 copies per ng genomic DNA). This procedure determined the sample variability of the amplification process. The amplification procedure was reproducible as measured by 27–30% CV (resulting from duplicate first strand cDNA synthesis and triplicate amplification reactions). The reaction also maintains the relative abundance of D1 e3 transcripts in the mRNA samples following amplification (2.2 vs. 1.7) representing 30% amplification bias after three steps.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a rolling circle replication primer" includes a plurality of such rolling circle replication primers, reference to "the first strand cDNA molecules" is a reference to one or more first strand cDNA molecules and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are specifically incorporated by reference. Nothing herein is to be construed as an admission that the present invention is not entitled to antedate such disclosure by virtue of prior invention.

Those skilled in the art will recognize, or be able to ascertain using no more than routine experimentation, many equivalents to the specific embodiments of the method and compositions described herein. Such equivalents are intended to be encompassed by the following claims.

We claim:

1. A method of amplifying RNA sequences, the method comprising
   incubating a cDNA primer and an RNA sample comprising RNA molecules under conditions that promote synthesis of first strand cDNA molecules from the RNA molecules,
   incubating a circularization probe and the first strand cDNA molecules under conditions that promote circularization of the first strand cDNA molecules, and
   incubating the circularized first strand cDNA molecules under conditions that promote rolling circle replication of the circularized first strand cDNA molecules, thereby amplifying RNA sequences.

2. The method of claim 1 wherein the rolling circle replication results in formation of tandem sequence DNA, wherein the tandem sequence DNA is replicated to form secondary tandem sequence DNA, wherein the tandem sequence DNA and the secondary tandem sequence DNA form double-stranded tandem sequence DNA.

3. The method of claim 2 wherein each double-stranded tandem sequence DNA comprises multiple tandem repeat units of the same sequence, wherein each tandem repeat unit comprises one or more cleavage sites of interest, wherein the method further comprises
   cleaving the double-stranded tandem sequence DNA at a plurality of the cleavage sites resulting in tandem sequence DNA fragments, wherein at least one of the tandem sequence DNA fragments does not comprise a plurality of tandem repeat units.

4. The method of claim 3 wherein each tandem repeat unit comprises a single cleavage site of interest, wherein the cDNA primer comprises the cleavage site of interest.

5. The method of claim 4 wherein the cleavage site is a cleavage site for a restriction endonuclease, wherein the restriction endonuclease has a recognition sequence comprising at least seven nucleotides.

6. The method of claim 5 wherein the restriction endonuclease has a recognition sequence comprising at least eight nucleotides.

7. The method of claim 6 wherein the restriction endonuclease is Not I, Asc I, AsiS I, Fse I, Pac I, Pme I, Sbf I, Sfi I, or Swa I.

8. The method of claim 4 wherein the cleavage site is a cleavage site for a restriction endonuclease, wherein the restriction endonuclease has a recognition sequence that occurs once every 65,536 nucleotides or more on average.

9. The method of claim 3 wherein each tandem repeat unit comprises a single cleavage site of interest, wherein the circularization probe comprises the cleavage site of interest.

10. The method of claim 3 wherein each tandem repeat unit comprises a single cleavage site of interest, wherein at least one of the tandem sequence DNA fragments consists of a single tandem repeat unit.

11. The method of claim 10 wherein a plurality of the tandem sequence DNA fragments consists of a single tandem repeat unit.

12. The method of claim 11 wherein a majority of the tandem sequence DNA fragments consists of a single tandem repeat unit.

13. The method of claim 12 wherein substantially all of the tandem sequence DNA fragments consists of a single tandem repeat unit.

14. The method of claim 13 further comprising cloning one or more of the single tandem repeat units.

15. The method of claim 14 wherein the single tandem repeat units are separated by size prior to cloning, wherein only single tandem repeat units having sizes of interest are cloned.

16. The method of claim 15 wherein only single tandem repeat units having a size the same as or greater than a size of interest are cloned.

17. The method of claim 14 wherein the cloned tandem repeat units constitute a cDNA library.

18. The method of claim 10 wherein the sequence of the single tandem repeat unit corresponds to the sequence of one of the circularized first strand cDNA molecules, wherein the sequence of the single tandem repeat unit is a circular permutation of the sequence of one of the circularized first strand cDNA molecules.

19. The method of claim 10 wherein the sequence of the single tandem repeat unit corresponds to the sequence of one of the circularized first strand cDNA molecules, wherein the sequence of the single tandem repeat is not a circular permutation of the sequence of one of the circularized first strand cDNA molecules.

20. The method of claim 10 wherein the single tandem repeat units constitute a cDNA library.

21. The method of claim 10 wherein rolling circle replication is primed by a rolling circle replication primer, wherein the rolling circle replication primer further comprises a promoter portion.

22. The method of claim 21 wherein the promoter portion is a promoter for a phage RNA polymerase or a bacterial RNA polymerase.

23. The method of claim 22 wherein the promoter is a promoter for T3 RNA polymerase, T7 RNA polymerase, or SP6 RNA polymerase.

24. The method of claim 21 further comprising transcribing the tandem repeat units, whereby tandem repeat transcripts are produced, wherein the tandem repeat transcripts are transcripts of single tandem repeat units.

25. The method of claim 24 wherein the tandem repeat transcripts are used, directly or indirectly, in a hybridization assay.

26. The method of claim 24 wherein the tandem repeat transcripts are associated with a solid-state substrate.

27. The method of claim 24 wherein the tandem repeat transcripts are translated.

28. The method of claim 10 wherein the cDNA primer further comprises a promoter portion.

29. The method of claim 28 wherein the promoter portion is a promoter for a phage RNA polymerase or a bacterial RNA polymerase.

30. The method of claim 29 wherein the promoter is a promoter for T3 RNA polymerase, T7 RNA polymerase, or SP6 RNA polymerase.

31. The method of claim 28 further comprising transcribing the tandem repeat units, whereby tandem repeat transcripts are produced, wherein the tandem repeat transcripts are transcripts of single tandem repeat units.

32. The method of claim 31 wherein the tandem repeat transcripts are used, directly or indirectly, in a hybridization assay.

33. The method of claim 31 wherein the tandem repeat transcripts are associated with a solid-state substrate.

34. The method of claim 31 wherein the tandem repeat transcripts are translated.

35. The method of claim 10 wherein the tandem repeat units are used, directly or indirectly, in a hybridization assay.

36. The method of claim 10 wherein the tandem repeat units are associated with a solid-state substrate.

37. The method of claim 3 further comprising inserting one or more of the tandem sequence DNA fragments into one or more vectors to form one or more recombinant vectors.

38. The method of claim 37 wherein the tandem sequence DNA fragments are separated by size prior to insertion into vectors, wherein only tandem sequence DNA fragments having sizes of interest are inserted into vectors.

39. The method of claim 38 wherein only tandem sequence DNA fragments having a size the same as or greater than a size of interest are cloned.

40. The method of claim 37 wherein the recombinant vectors constitute a cDNA library.

41. The method of claim 3 further comprising cloning one or more of the tandem sequence DNA fragments.

42. The method of claim 41 wherein the tandem sequence DNA fragments are separated by size prior to cloning, wherein only tandem sequence DNA fragments having sizes of interest are cloned.

43. The method of claim 42 wherein only tandem sequence DNA fragments having a size the same as or greater than a size of interest are cloned.

44. The method of claim 41 wherein the cloned tandem sequence DNA fragments constitute a cDNA library.

45. The method of claim 3 wherein the tandem sequence DNA fragments constitute a cDNA library.

46. The method of claim 3 wherein at least one of the tandem sequence DNA fragments comprises a single tandem repeat unit, wherein the method further comprises cloning one or more of the single tandem repeat units.

47. The method of claim 46 wherein the single tandem repeat units are separated by size prior to cloning, wherein only single tandem repeat units having sizes of interest are cloned.

48. The method of claim 47 wherein only single tandem repeat units having a size the same as or greater than a size of interest are cloned.

49. The method of claim 46 wherein the cloned tandem repeats constitute a cDNA library.

50. The method of claim 3 wherein the tandem sequence DNA fragments are used, directly or indirectly, in a hybridization assay.

51. The method of claim 3 wherein the tandem sequence DNA fragments are associated with a solid-state substrate.

52. The method of claim 1 wherein the cDNA primer comprises an RNA complement portion, wherein the RNA complement portion hybridizes to one or more of the RNA molecules, wherein the cDNA primer is incorporated into the first strand cDNA molecules during synthesis of the first strand cDNA molecules.

53. The method of claim 52 wherein the RNA complement portion comprises poly(dT), wherein the RNA molecules are mRNA molecules.

54. The method of claim 52 wherein the RNA complement portion is complementary to sequence in one or more RNA molecules.

55. The method of claim 54 wherein the RNA complement portion is complementary to sequence in one of the RNA molecules, wherein the cDNA primer is specific for the RNA molecule.

56. The method of claim 52 wherein the cDNA primer further comprises a cleavage site.

57. The method of claim 56 wherein the cleavage site is a cleavage site for a restriction endonuclease, wherein the restriction endonuclease has a recognition sequence comprising at least seven nucleotides.

58. The method of claim 57 wherein the restriction endonuclease has a recognition sequence comprising at least eight nucleotides.

59. The method of claim 58 wherein the restriction endonuclease is Not I, Asc I, AsiS I, Fse I, Pac I, Pme I, Sbf I, Sfi I, or Swa I.

60. The method of claim 56 wherein the cleavage site is a cleavage site for a restriction endonuclease, wherein the restriction endonuclease has a recognition sequence that occurs once every 65,536 nucleotides or more on average.

61. The method of claim 56 wherein the rolling circle replication results in formation of tandem sequence DNA, wherein the tandem sequence DNA is replicated to form secondary tandem sequence DNA, wherein the tandem sequence DNA and the secondary tandem sequence DNA form double-stranded tandem sequence DNA, wherein each double-stranded tandem sequence DNA comprises multiple tandem repeats of the same sequence, wherein each tandem repeat comprises the cleavage site, wherein the method further comprises cleaving the double-stranded tandem sequence DNA at a plurality of the cleavage sites resulting in tandem sequence DNA fragments.

62. The method of claim 52 wherein the cDNA primer further comprises a probe complement portion, wherein the probe complement portion is complementary to sequence in the circularization probe.

63. The method of claim 52 wherein the cDNA primer further comprises a primer complement portion, wherein the primer complement portion is complementary to a rolling circle replication primer.

64. The method of claim 63 wherein the cDNA primer further comprises a primer matching portion, wherein the primer matching portion matches sequence in a secondary DNA strand displacement primer.

65. The method of claim 64 wherein the cDNA primer further comprises a promoter portion.

66. The method of claim 52 wherein the cDNA primer further comprises a primer matching portion, wherein the primer matching portion matches sequence in a secondary DNA strand displacement primer.

67. The method of claim 52 wherein the cDNA primer further comprises a promoter portion.

68. The method of claim 67 wherein the promoter portion is a promoter for a phage RNA polymerase or a bacterial RNA polymerase.

69. The method of claim 68 wherein the promoter is a promoter for T3 RNA polymerase, T7 RNA polymerase, or SP6 RNA polymerase.

70. The method of claim 52 wherein the cDNA primer comprises nucleotides, wherein one or more of the nucleotides are ribonucleotides.

71. The method of claim 70 wherein from about 10% to about 50% of the nucleotides are ribonucleotides.

72. The method of claim 70 wherein about 50% or more of the nucleotides are ribonucleotides.

73. The method of claim 70 wherein all of the nucleotides are ribonucleotides.

74. The method of claim 52 wherein the cDNA primer comprises nucleotides, wherein one or more of the nucleotides are 2'-O-methyl ribonucleotides.

75. The method of claim 74 wherein from about 10% to about 50% of the nucleotides are 2'-O-methyl ribonucleotides.

76. The method of claim 74 wherein about 50% or more of the nucleotides are 2'-O-methyl ribonucleotides.

77. The method of claim 74 wherein all of the nucleotides are 2'-O-methyl ribonucleotides.

78. The method of claim 52 wherein the cDNA primer comprises nucleotides, wherein the nucleotides are a mixture of ribonucleotides and 2'-O-methyl ribonucleotides.

79. The method of claim 52 wherein the cDNA primer comprises nucleotides, wherein the nucleotides are a mixture of deoxyribonucleotides and 2'-O-methyl ribonucleotides.

80. The method of claim 1 wherein the cDNA primer is incorporated into the first strand cDNA molecules during synthesis of the first strand cDNA molecules, wherein the circularization probe comprises a cDNA complement portion and a primer complement portion, wherein the cDNA complement portion hybridizes to one or more of the first strand cDNA molecules, wherein the primer complement portion hybridizes to the cDNA primer incorporated into the first strand cDNA molecules, wherein hybridization of the cDNA complement portion to the first strand cDNA molecules and hybridization of the primer complement portion to the cDNA primer brings the ends of the first strand cDNA molecules into proximity thereby mediating circularization of the first strand cDNA molecules.

81. The method of claim 80 wherein the cDNA complement portion comprises a random or partially random sequence.

82. The method of claim 80 wherein the cDNA complement portion comprises nucleotides, wherein one or more of the nucleotides comprise a universal base.

83. The method of claim 82 wherein the universal base is 5-nitroindole or 3-nitropyrrole.

84. The method of claim 80 wherein the cDNA complement portion comprises nucleotides, wherein one or more of the nucleotides can base pair with more than one type of nucleotide.

85. The method of claim 84 wherein the nucleotide that can base pair with more than one type of nucleotide is inosine or a nucleotide comprising a universal base.

86. The method of claim 85 wherein the universal base is 5-nitroindole or 3-nitropyrrole.

87. The method of claim 80 wherein the circularization probe further comprises a cleavage site, wherein the primer complement portion comprises the cleavage site.

88. The method of claim 87 wherein the cleavage site is a cleavage site for a restriction endonuclease, wherein the restriction endonuclease has a recognition sequence comprising at least seven nucleotides.

89. The method of claim 88 wherein the restriction endonuclease has a recognition sequence comprising at least eight nucleotides.

90. The method of claim 89 wherein the restriction endonuclease is Not I, Asc I, AsiS I, Fse I, Pac I, Pme I, Sbf I, Sfi I, or Swa I.

91. The method of claim 87 wherein the cleavage site is a cleavage site for a, restriction endonuclease, wherein the restriction endonuclease has a recognition sequence that occurs once every 65,536 nucleotides or more on average.

92. The method of claim 87 wherein the rolling circle replication results in formation of tandem sequence DNA, wherein the tandem sequence DNA is replicated to form secondary tandem sequence DNA, wherein the tandem sequence DNA and the secondary tandem sequence DNA form double-stranded tandem sequence DNA, wherein each double-stranded tandem sequence DNA comprises multiple tandem repeats of the same sequence, wherein each tandem repeat comprises the cleavage site, wherein the method further comprises
cleaving the double-stranded tandem sequence DNA at a plurality of the cleavage sites resulting in tandem sequence DNA fragments.

93. The method of claim 80 wherein the primer complement portion is complementary to sequence in the cDNA primer.

94. The method of claim 80 wherein the circularization probe further comprises a second primer complement portion, wherein the second primer complement portion is complementary to a secondary DNA strand displacement primer.

95. The method of claim 94 wherein the circularization probe further comprises primer matching portion, wherein the primer matching portion matches sequence in a rolling circle replication primer.

96. The method of claim 95 wherein the circularization probe further comprises a promoter portion.

97. The method of claim 80 wherein the circularization probe further comprises a primer matching portion, wherein the primer matching portion matches sequence in a secondary DNA strand displacement primer.

98. The method of claim 80 wherein the circularization probe further comprises a promoter portion.

99. The method of claim 98 wherein the promoter portion is a promoter for a phage RNA polymerase or a bacterial RNA polymerase.

100. The method of claim 99 wherein the promoter is a promoter for T3 RNA polymerase, T7 RNA polymerase, or SP6 RNA polymerase.

101. The method of claim 80 wherein the circularization probe comprises nucleotides, wherein one or more of the nucleotides are ribonucleotides.

102. The method of claim 101 wherein from about 10% to about 50% of the nucleotides are ribonucleotides.

103. The method of claim 101 wherein about 50% or more of the nucleotides are ribonucleotides.

104. The method of claim 101 wherein all of the nucleotides are ribonucleotides.

105. The method of claim 80 wherein the circularization probe comprises nucleotides, wherein one or more of the nucleotides are 2'-O-methyl ribonucleotides.

106. The method of claim 105 wherein from about 10% to about 50% of the nucleotides are 2'-O-methyl ribonucleotides.

107. The method of claim 105 wherein about 50% or more of the nucleotides are 2'-O-methyl ribonucleotides.

108. The method of claim 105 wherein all of the nucleotides are 2'-O-methyl ribonucleotides.

109. The method of claim 80 wherein the circularization probe comprises nucleotides, wherein the nucleotides are a mixture of ribonucleotides and 2'-O-methyl ribonucleotides.

110. The method of claim 80 wherein the circularization probe comprises nucleotides, wherein the nucleotides are a mixture of deoxyribonucleotides and 2'-O-methyl ribonucleotides.

111. The method of claim 1 wherein rolling circle replication is primed by a rolling circle replication primer, wherein the rolling circle replication primer has a random sequence, wherein the rolling circle replication is primed from a plurality of locations on the circularized first strand cDNA molecules.

112. The method of claim 111 wherein the rolling circle replication results in formation of tandem sequence DNA, wherein the tandem sequence DNA is replicated to form secondary tandem sequence DNA, wherein replication of the tandem sequence DNA is primed by the rolling circle replication primer.

113. The method of claim 111 wherein the circularized first strand cDNA molecules are amplified via exponential rolling circle amplification.

114. The method of claim 1 wherein rolling circle replication is primed by a plurality of rolling circle replication primers, wherein the rolling circle replication is primed from a plurality of locations on the circularized first strand cDNA molecules.

115. The method of claim 114 wherein the rolling circle replication results in formation of tandem sequence DNA, wherein the tandem sequence DNA is replicated to form secondary tandem sequence DNA, wherein replication of the tandem sequence DNA is primed by one or more secondary DNA strand displacement primers.

116. The method of claim 114 wherein the circularized first strand cDNA molecules are amplified via exponential rolling circle amplification.

117. The method of claim 1 wherein rolling circle replication is primed by one or more rolling circle replication primers, wherein the rolling circle replication results in formation of tandem sequence DNA, wherein the tandem sequence DNA is not replicated, wherein the tandem sequence DNA comprises sequence matching sequence in the RNA molecules.

118. The method of claim 117 wherein the tandem sequence DNA is used, directly or indirectly, in a hybridization assay.

119. The method of claim 117 wherein the tandem sequence DNA is associated with a solid-state substrate.

120. The method of claim 1 wherein rolling circle replication is primed by the circularization probe, wherein the rolling circle replication results in formation of tandem sequence DNA, wherein the tandem sequence DNA is not replicated, wherein the tandem sequence DNA comprises sequence matching sequence in the RNA molecules.

121. The method of claim 120 wherein the tandem sequence DNA is used, directly or indirectly, in a hybridization assay.

122. The method of claim 120 wherein the tandem sequence DNA is associated with a solid-state substrate.

123. The method of claim 1 wherein rolling circle replication is primed by one or more rolling circle replication primers, wherein the rolling circle replication results in formation of tandem sequence DNA, wherein the tandem sequence DNA is replicated to form secondary tandem sequence DNA, wherein replication of the tandem sequence DNA is primed by one or more secondary DNA strand displacement primers, wherein the rolling circle replication primers have 5' phosphates, wherein the secondary DNA strand displacement primers have 5' hydroxyls, wherein the tandem sequence DNA has 5' phosphates, wherein the secondary tandem sequence DNA has 5' hydroxyls, wherein the method further comprises incubating the tandem sequence DNA and secondary tandem sequence DNA in the presence of a phosphate-dependent exonuclease, whereby the tandem sequence DNA is degraded and the secondary tandem sequence DNA remains.

124. The method of claim 123 wherein the phosphate-dependent exonuclease is lambda exonuclease.

125. The method of claim 123 wherein the secondary tandem sequence DNA comprises sequence complementary to sequence in the RNA molecules, wherein the secondary tandem sequence DNA is used, directly or indirectly, in a hybridization assay.

126. The method of claim 123 wherein the secondary tandem sequence DNA comprises sequence complementary to sequence in the RNA molecules, wherein the secondary tandem sequence DNA is associated with a solid-state substrate.

127. The method of claim 1 wherein rolling circle replication is primed by one or more rolling circle replication primers, wherein the rolling circle replication results in formation of tandem sequence DNA, wherein the tandem sequence DNA is replicated to form secondary tandem sequence DNA, wherein replication of the tandem sequence DNA is primed by one or more secondary DNA strand displacement primers, wherein the rolling circle replication primers have 5' hydroxyls, wherein the secondary DNA strand displacement primers have 5' phosphates, wherein the tandem sequence DNA has 5' hydroxyls, wherein the secondary tandem sequence DNA has 5' phosphates, wherein the method further comprises incubating the tandem sequence DNA and secondary tandem sequence DNA in the presence of a phosphate-dependent exonuclease, whereby the secondary tandem sequence DNA is degraded and the tandem sequence DNA remains.

128. The method of claim 127 wherein the phosphate-dependent exonuclease is lambda exonuclease.

129. The method of claim 127 wherein the tandem sequence DNA comprises sequence matching sequence in the RNA molecules, wherein the tandem sequence DNA is used, directly or indirectly, in a hybridization assay.

130. The method of claim 127 wherein the tandem sequence DNA comprises sequence matching sequence in the RNA molecules, wherein the tandem sequence DNA is associated with a solid-state substrate.

131. The method of claim 1 wherein rolling circle replication is primed by the circularization probe, wherein the rolling circle replication results in formation of tandem sequence DNA, wherein the tandem sequence DNA is replicated to form secondary tandem sequence DNA, wherein replication of the tandem sequence DNA is primed by one or more secondary DNA strand displacement primers, wherein the circularization probe has a 5' phosphate, wherein the secondary DNA strand displacement primers have 5' hydroxyls, wherein the tandem sequence DNA has 5' phosphates, wherein the secondary tandem sequence DNA has 5' hydroxyls, wherein the method further comprises incubating the tandem sequence DNA and secondary tandem sequence DNA in the presence of a phosphate-dependent exonuclease, whereby the tandem sequence DNA is degraded and the secondary tandem sequence DNA remains.

132. The method of claim 131 wherein the phosphate-dependent exonuclease is lambda exonuclease.

133. The method of claim 131 wherein the secondary tandem sequence DNA comprises sequence complementary to sequence in the RNA molecules, wherein the secondary tandem sequence DNA is used, directly or indirectly, in a hybridization assay.

134. The method of claim 131 wherein the secondary tandem sequence DNA comprises sequence complementary to sequence in the RNA molecules, wherein the secondary tandem sequence DNA is associated with a solid-state substrate.

135. The method of claim 1 wherein rolling circle replication is primed by the circularization probe, wherein the rolling circle replication results in formation of tandem sequence DNA, wherein the tandem sequence DNA is replicated to form secondary tandem sequence DNA, wherein replication of the tandem sequence DNA is primed by one or more secondary DNA strand displacement primers, wherein the circularization probe has a 5' hydroxyl, wherein the secondary DNA strand displacement primers have 5' phosphates, wherein the tandem sequence DNA has 5' hydroxyls, wherein the secondary tandem sequence DNA has 5' phosphates, wherein the method further comprises incubating the tandem sequence DNA and secondary tandem sequence DNA in the presence of a phosphate-dependent exonuclease, whereby the secondary tandem sequence DNA is degraded and the tandem sequence DNA remains.

136. The method of claim 135 wherein the phosphate-dependent exonuclease is lambda exonuclease.

137. The method of claim 135 wherein the tandem sequence DNA comprises sequence matching sequence in the RNA molecules, wherein the tandem sequence DNA is used, directly or indirectly, in a hybridization assay.

138. The method of claim 135 wherein the tandem sequence DNA comprises sequence matching sequence in the RNA molecules, wherein the tandem sequence DNA is associated with a solid-state substrate.

139. The method of claim 1 wherein rolling circle replication is primed by a rolling circle replication primer, wherein the rolling circle replication primer further comprises a promoter portion, wherein the rolling circle replication results in formation of tandem sequence DNA.

140. The method of claim 139 wherein the promoter portion is a promoter for a phage RNA polymerase or a bacterial RNA polymerase.

141. The method of claim 140 wherein the promoter is a promoter for T3 RNA polymerase, T7 RNA polymerase, or SP6 RNA polymerase.

142. The method of claim 139 further comprising transcribing the tandem sequence DNA, whereby tandem sequence transcripts are produced.

143. The method of claim 142 wherein the tandem sequence transcripts are used, directly or indirectly, in a hybridization assay.

144. The method of claim 142 wherein the tandem sequence transcripts are associated with a solid-state substrate.

145. The method of claim 142 wherein the tandem sequence transcripts are translated.

146. The method of claim 1 wherein the cDNA primer further comprises a promoter portion, wherein the rolling circle replication results in formation of tandem sequence DNA.

147. The method of claim 146 wherein the promoter portion is a promoter for a phage RNA polymerase or a bacterial RNA polymerase.

148. The method of claim 147 wherein the promoter is a promoter for T3 RNA polymerase, T7 RNA polymerase, or SP6 RNA polymerase.

149. The method of claim 146 further comprising transcribing the tandem sequence DNA, whereby tandem sequence transcripts are produced.

150. The method of claim 149 wherein the tandem sequence transcripts are used, directly or indirectly, in a hybridization assay.

151. The method of claim 149 wherein the tandem sequence transcripts are associated with a solid-state substrate.

152. The method of claim 149 wherein the tandem sequence transcripts are translated.

153. The method of claim 1 wherein the rolling circle replication results in formation of tandem sequence DNA, wherein the method further comprises
detecting one or more target sequences in the tandem sequence DNA.

154. The method of claim 153 wherein the one or more target sequences correspond to target sequences in the RNA molecules, wherein detection of the one or more target sequences indicates the presence of the corresponding RNA molecules in the RNA sample.

155. The method of claim 153 wherein the RNA sample is derived from a subject, wherein one or more of the target sequences is related to a disease or condition, wherein detection of the one or more target sequences related to a disease or condition indicates that the subject from which the RNA sample is derived is or is not at risk for the related disease or condition.

156. The method of claim 153 wherein a plurality of first strand cDNA molecules are synthesized from a plurality of RNA molecules, wherein a plurality of tandem sequence DNAs are formed, wherein the plurality of tandem sequence DNAs correspond to the plurality of RNA molecules, wherein a plurality of target sequences are detected, wherein the plurality of target sequences detected constitute a catalog of sequences derived from the RNA sample.

157. The method of claim 156 wherein the method further comprises comparing the catalog of sequences to another catalog of sequences produced in the same way from a different RNA sample.

158. The method of claim 153 wherein the presence and absence of sequences of interest in the catalog of sequences indicates that the subject from which the RNA sample is derived is or is not at risk for a disease or condition.

159. The method of claim 1 wherein the rolling circle replication results in formation of tandem sequence DNA, wherein a plurality of first strand cDNA molecules are synthesized from a plurality of RNA molecules, wherein a plurality of tandem sequence DNAs are formed, wherein the plurality of tandem sequence DNAs correspond to the plurality of RNA molecules, wherein the plurality of tandem sequence DNAs constitute a catalog of sequences derived from the RNA sample.

160. The method of claim 159 wherein the catalog of sequences comprises tandem sequence DNA corresponding to a significant number of the RNA molecules in the RNA sample.

161. The method of claim 160 wherein the catalog of sequences comprises tandem sequence DNA corresponding to a substantial number of the RNA molecules in the RNA sample.

162. The method of claim 1 wherein the rolling circle replication results in formation of tandem sequence DNA, wherein the method further comprises
sequencing one or more target sequences in the tandem sequence DNA.

163. The method of claim 162 wherein the one or more target sequences correspond to target sequences in the RNA molecules, wherein the sequence of the one or more target sequences corresponds to sequence of the corresponding RNA molecules in the RNA sample.

164. The method of claim 1 wherein the rolling circle replication results in formation of tandem sequence DNA, wherein the method further comprises, following the rolling circle replication,
incubating the tandem sequence DNA under conditions that promote replication of the tandem sequence DNA, wherein during replication of the tandem sequence DNA at least one of the replicated strands is displaced from the tandem sequence DNA by strand displacement replication of another replicated strand.

165. The method of claim 1 wherein the rolling circle replication results in formation of tandem sequence DNA, wherein the tandem sequence DNA is replicated to form secondary tandem sequence DNA during the rolling circle replication, wherein the method further comprises, following the rolling circle replication,
incubating the tandem sequence DNA and the secondary tandem sequence DNA under conditions that promote replication of the tandem sequence DNA and the secondary tandem sequence DNA, wherein during replication of the tandem sequence DNA and the secondary tandem sequence DNA at least one of the replicated strands is displaced from the tandem sequence DNA or the secondary tandem sequence DNA by strand displacement replication of another replicated strand.

166. The method of claim 1 wherein at least one of the first strand cDNA molecules is ligated to at least one other first strand cDNA molecule to form one or more first strand cDNA concatemers.

167. The method of claim 166 wherein at least one of the first strand cDNA. concatemers is not circularized, wherein the uncircularized first stand cDNA concatemer is replicated by strand displacement replication.

168. The method of claim 166 wherein at least one of the first strand cDNA concatemers is circularized, wherein the circularized first strand cDNA concatemer is replicated by rolling circle replication.

169. The method of claim 166 wherein at least one of the first strand cDNA concatemers is not circularized, wherein the uncircularized first stand cDNA concatemer is replicated by strand displacement replication, wherein at least one of the first strand cDNA concatemers is circularized, wherein the circularized first strand cDNA concatemer is replicated by rolling circle replication.

170. The method of claim 1 wherein the conditions that promote synthesis of first strand cDNA molecules comprise incubating the cDNA primer and the RNA sample in the presence of a reverse transcriptase, wherein the conditions that promote circularization of the first strand cDNA molecules comprise incubating the circularization probe and the first strand cDNA molecules in the presence of ligase, wherein the conditions that promote rolling circle replication of the circularized first cDNA molecules comprise incubating the circularized first strand cDNA molecules in the presence of a DNA polymerase.

171. The method of claim 170 wherein the RNA molecules are mRNA molecules, wherein the cDNA primer is 5'-GTGCGGCCGCTTTTTTTTTTTTTTTTTTTT-3' (SEQ ID NO:1), wherein the circularization probe is 5'-AAAAGCGGCCGCACNNNNNNN-3' (SEQ ID NO:2), wherein the reverse transcriptase is Superscript II reverse transcriptase, wherein the ligase is T4 DNA ligase, wherein the DNA polymerase is φ29 DNA polymerase.

172. The method of claim 170 wherein the method further comprises, following synthesis of first strand cDNA molecules and before circularization of the first strand cDNA molecules incubating the first strand cDNA molecules in the presence of an RNAse H activity, incubating the first strand cDNA molecules under alkaline conditions, neutralizing the first strand cDNA molecules, and purifying the first strand cDNA molecules.

173. The method of claim 172 wherein the RNAse H activity is provided by an RNAse H+ reverse transcriptase, wherein the alkaline conditions are produced by adding 0.1 M NaOH, wherein the first strand cDNA molecules are neutralized by adding 0.1 M HCl.

174. A method of amplifying RNA sequences, the method comprising incubating a cDNA primer and an RNA sample comprising RNA molecules under conditions that promote synthesis of first strand cDNA molecules from the RNA molecules, wherein the conditions that promote synthesis of first strand cDNA molecules comprise incubating the cDNA primer and the RNA sample in the presence of a reverse transcriptase, incubating the first strand cDNA molecules in the presence of an RNAse H activity, incubating the first strand cDNA molecules under alkaline conditions, neutralizing the first strand cDNA molecules, purifying the first strand cDNA molecules, incubating a circularization probe and the first strand cDNA molecules under conditions that promote circularization of the first strand cDNA molecules, wherein the conditions that promote circularization of the first strand cDNA molecules comprise incubating the circularization probe and the first strand cDNA molecules in the presence of ligase, incubating the circularized first strand cDNA molecules under conditions that promote rolling circle replication of the circularized first strand cDNA molecules, thereby amplifying RNA sequences, wherein the conditions that promote rolling circle replication of the circularized first strand cDNA molecules comprise incubating the circularized first strand cDNA molecules in the presence of a DNA polymerase.

175. The method of claim 174 wherein the RNA molecules are mRNA molecules, wherein the cDNA primer is 5'-GTGCGGCCGCTTTTTTTTTTTTTTTTTTTT-3' (SEQ ID NO:1), wherein the circularization probe is 5'-AAAAGCGGCCGCACNNNNNNN-3' (SEQ ID NO:2), wherein the reverse transcriptase is Superscript II reverse transcriptase, wherein the RNAse H activity is provided by an RNAse H+ reverse transcriptase, wherein the alkaline conditions are produced by adding 0.1 M NaOH, wherein the first strand cDNA molecules are neutralized by adding 0.1 M HCl, wherein the ligase is T4 DNA ligase, wherein the DNA polymerase is φ29 DNA polymerase.

176. A method of amplifying RNA sequences, the method comprising incubating a cDNA primer and an RNA sample comprising RNA molecules under conditions that promote synthesis of first strand cDNA molecules from the RNA molecules, incubating a circularization probe and the first strand cDNA molecules under conditions that promote ligation of the first strand cDNA molecules to each other to form first strand cDNA concatemers, and incubating the first strand cDNA concatemers under conditions that promote strand displacement replication of the first strand cDNA concatemers, thereby amplifying RNA sequences.

177. The method of claim 176 wherein at least one of the first strand cDNA concatemers is circularized, wherein the circularized first strand cDNA concatemer is replicated by rolling circle replication.

178. The method of claim 176 wherein at least one of the first strand cDNA molecules is circularized, wherein the circularized first strand cDNA molecule is replicated by rolling circle replication.

179. The method of claim 176 wherein at least one of the first strand cDNA concatemers is circularized, wherein the circularized first strand cDNA concatemer is replicated by rolling circle replication, wherein at least one of the first strand cDNA molecules is circularized, wherein the circularized first strand cDNA molecule is replicated by rolling circle replication.

\* \* \* \* \*